US007259009B2

(12) United States Patent
Seed et al.

(10) Patent No.: US 7,259,009 B2
(45) Date of Patent: Aug. 21, 2007

(54) SELF-REARRANGING DNA VECTORS

(75) Inventors: Brian Seed, Derry, NH (US); Mason Wright Freeman, Lincoln, MA (US); Alexander Kovtun, Maynard, MA (US); Masahiro Murakawa, Fukuoka (JP); Eun-Chung Park, Baltimore, MD (US); Xinzhong Wang, Framingham, MA (US)

(73) Assignee: The General Hospital Corporation, Boston, MA (US)

( * ) Notice: Subject to any disclaimer, the term of this patent is extended or adjusted under 35 U.S.C. 154(b) by 404 days.

(21) Appl. No.: 10/384,136

(22) Filed: Mar. 7, 2003

(65) Prior Publication Data

US 2004/0028653 A1 Feb. 12, 2004

Related U.S. Application Data

(63) Continuation of application No. PCT/US01/27682, filed on Sep. 7, 2001.

(60) Provisional application No. 60/246,904, filed on Nov. 8, 2000, provisional application No. 60/231,053, filed on Sep. 8, 2000.

(51) Int. Cl.
*C12N 15/00* (2006.01)
*C07H 21/04* (2006.01)

(52) U.S. Cl. ................. 435/320.1; 536/23.2; 536/23.5; 536/24.1

(58) Field of Classification Search ..................... None
See application file for complete search history.

(56) References Cited

U.S. PATENT DOCUMENTS 5,919,676 A 7/1999 Graham et al.
6,080,576 A 6/2000 Zambrowicz et al.
6,630,322 B1 * 10/2003 Perricaudet et al. ....... 435/69.1

FOREIGN PATENT DOCUMENTS

WO WO97/47757 * 12/1997
WO WO99/43843 A1 9/1999

OTHER PUBLICATIONS

Agah et al.,"Gene Recombination in Postmitotic Cells," *J. Clin. Invest.* 100:169-179 (1997).

Pavlakis, George N., "Gene Expression Using DNA Viral Vectors", *Current Opinion in Biotechnology,* 1:48-54 (1990).

Wang et al, "Episomal Segregation of the Adenovirus Enhancer Sequence by Conditional Genome Rearrangement Abrogates Late Viral Gene Expression", *Journal of Virology,* 74:11296-11303 (2000).

Supplementary Partial European Search Report (EP 01 96 8599) completed Apr. 19, 2005.

Castro-Peralta et al., "The Use of Oligonucleotide Directed Cleavage of DNA and Homologous Recombination in the Production of Large Recombinant Adenoviral Vectors," Gene Ther., 7:583-586 (2000).

Chen et al., "Production and Characterization of Human 293 Cell Lines Expressing the Site-Specific Recombinase Cre," Somat. Cell Mol. Genet., 22:477-488 (1996).

Mizuguchi et al., "Efficient Construction of a Recombinant Adenovirus Vector by an Improved *In Vitro* Ligation Method," Hum. Gene Ther., 9:2577-2583 (1998).

Ng et al., "A High-Efficiency Cre/*LoxP*-Based System for Construction of Adenoviral Vectors," Hum. Gene Ther., 10:2667-2672 (1999).

Ng et al., "Yeast Recombinase FLP Functions Effectively in Human Cells for Construction of Adenovirus Vectors," Biotechniques, 29:524-528 (2000).

Supplementary Partial European Search Report, dated Jul. 19, 2005, (EP 01 968599).

* cited by examiner

*Primary Examiner*—Richard Schnizer
(74) *Attorney, Agent, or Firm*—Clark & Elbing LLP

(57) ABSTRACT

Disclosed are replicatable viral DNA vectors encoding a site-specific DNA-altering enzyme and a DNA target recognized by the enzyme, the enzyme selectively converting, in a cell expressing the enzyme, the DNA vector to a rearranged form. The invention further relates to methods for assembling recombinant adenoviral DNAs. These methods include the steps of: (a) providing a first linearized DNA vector including a restriction site and a cos site and a second linearized DNA vector including the restriction site, an adenoviral nucleic acid molecule, and a cos site; and (b) ligating the first and second linearized DNA vectors, the ligation assembling a recombinant adenoviral DNA.

14 Claims, 40 Drawing Sheets
(8 of 40 Drawing Sheet(s) Filed in Color)

| Ad DNA forms | | Digestion | CPEs | Time (days) |
|---|---|---|---|---|
| 1. Circular Ad DNA |  | pIAd2B | 0.17 | -- |
| 2. Linearized cosmid DNA |  | pIAd2B / I-CeuI | 8.5 | 10 |
| |  | pIAd2B / BsaBI | 8.5 | 10 |
| 3. Liberated AdV DNA from cosmid |  | pIAd2B / I-CeuI +BsaBI | 76 | 6 |

Human primary hepatocytes

FIG. 8B

| | # of TPL mRNA / $10^6$ AdV DNA |
|---|---|
| Ad2HCRGFP | $1.15 \pm 0.28 \times 10^4$ |
| Ad2HCRGFP/EBV | Non-detectable |

0 μM Est.

2 μM Est.

SEQUENCE LISTING

```
<160> NUMBER OF SEQ ID NOS: 10

<210> SEQ ID NO 1
<211> LENGTH: 2341
<212> TYPE: DNA
<213> ORGANISM: Artificial Sequence
<220> FEATURE:
<223> OTHER INFORMATION: derived from Adenovirus

<400> SEQUENCE: 1

gaatcggcca gcgcgaattc gattatcatc atcataatat accttatttt ggattgaagc     60

caatatgata atgagggggt ggagtttgtg acgtggcgcg gggcgtggga acggggcggg    120

tgacgtaggt tttagggcgg agtaacttgc atgtattggg aattgtagtt tttttaaaat    180

gggaagttac gtacgcggca tcgatgcgcg ggatatcgcg gcggctagcg acatgaggtt    240

gccccgtatt cagtgtcgct gatttgtatt gtctgaagtt gtttttacgt taagttgatg    300

cagatcaatt aatacgatac ctgcgtcata attgattatt tgacgtggtt tgatggcctc    360

cacgcacgtt gtgatatgta gatgataatc attatcactt tacgggtcct ttccggtgat    420

ccgacaggtt acggggcggc gacctcgcgg gttttcgcta tttatgaaaa ttttccggtt    480

taaggcgttt ccgttcttct tcgtcataac ttaatgtttt tatttaaaat accctctgaa    540

aagaaaggaa acgacaggtg ctgaaagcga ggctttttgg cctctgtcgt ttcctttctc    600

tgtttttgtc cgtggaatga acaatggaag ttaacggatc caggccgcga gcaaaaggcc    660

agcaaaaggc caggaaccgt aaaaaggccg cgttgctggc gtttttccat aggctccgcc    720

cccctgacga gcatcacaaa aatcaacgct caagtcagag gtggcgaaac ccgacaggac    780

tataaagata ccaggcgttt ccccctggaa gctccctcgt gcgctctcct gttccgaccc    840

tgccgcttac cggatacctg tccgcctttc tcccttcggg aagcgtggcg ctttctcata    900

gctcacgctg taggtatctc agttcggtgt aggtcgttcg ctccaagctg ggctgtgtgc    960

acgaaccccc cgttcagccc gaccgctgcg ccttatccgg taactatcgt cttgagtcca   1020

acccggtaag acacgactta tcgccactgg cagcagccac tggtaacagg attagcagag   1080

cgaggtatgt aggcggtgct acagagttct tgaagtggtg gcctaactac ggctacacta   1140

gaagaacagt atttggtatc tgcgctctgc caaagccagt taccttcgga aaaagagttg   1200

gtagctcttg atccggcaaa caaaccaccg ctggtagcgg tggttttttt gtttgcaagc   1260

agcagattac gcgcagaaaa aaaggatctc aagaagatcc tttgatcttt tctacggggt   1320

ctgacgctca gtggaacgaa aactcacgtt aagggatttt ggtcatcaga ttatcaaaaa   1380

ggatcttcac ctagatcctt ttaaattaaa aatgaagttt taaatcaatc taaagtatat   1440

atgagtaaac ttggtctgac agttaccaat gcttaatcag tgaggcacct atctcagcga   1500

tctgtctatt tcgttcatcc atagttgcct gactccccgt agtgtagata actacgatac   1560

gggagggctt accatccggc cccagtgctg caatgatacc gcgtgaccca cgctcaccgg   1620

ctcctgattt atcagcaata aaccagccag ccggaagtgc cgagcgcaga agtggtcctg   1680
```

-continued caactttatc cgcctccatc cagtctatta gttgttgccg ggaagctaga gtaagtagtt 1740
cgccagttaa tagttttcgc aacgttgttg ccattgctac aggcatcgtg gtgtcacgct 1800
cgtcgtttgg tatggcttca ttcagctccg gttcccaacg atcaaggcga gttacatgat 1860
cccccatgtt gtgcaaaaaa gcggttagct ccttcggtcc tccgatagtt gtcagaagta 1920
agttggccgc agtgttatca ctcatggtta tggcagcact gcataattct cttactgtca 1980
tgccatccgt aagatgcttt tctgtgactg gtgagtattc aaccaagaat acgggataat 2040
accgcgccac atagcagaac tttaaaagtg ctcatcattg gaaaacgttc ttcggggcga 2100
aaactctcaa ggatcttacc gctgttgaga tccagttcga tgtaacccac tcgcgcaccc 2160
aagtgatctt ctgcatcttt tactttcacc agcgtttctg ggtgagcaaa aacaggaagg 2220
caaaatgccg caaaaaaggg aataagggcg acacggaaat gttgaatact catactcttc 2280
ctttttcaat attattgaag catttatcag ggttattgtc tcatgagcgg atacatattt 2340
g 2341

<210> SEQ ID NO 2
<211> LENGTH: 34616
<212> TYPE: DNA
<213> ORGANISM: Artificial Sequence
<220> FEATURE:
<223> OTHER INFORMATION: derived from Adenovirus

<400> SEQUENCE: 2
gaatcggcca gcgcgaatta actataacgg tcctaaggta gcgtcatcat cataatatac 60
cttattttgg attgaagcca atatgataat gaggggtgg agtttgtgac gtggcgcggg 120
gcgtgggaac ggggcgggtg acgtaggttt tagggcggag taacttgcat gtattgggaa 180
ttgtagtttt tttaaaatgg gaagttacgt atcgtgggaa aacggaagtg aagatttgag 240
gaagttgtgg gtttttggc tttcgtttct gggcgtaggt tcgcgtgcgg ttttctgggt 300 gtttttgtg gactttaacc gttacgtcat tttttagtcc tatatatact cgctctgtac 360
ttggcccttt ttacactgtg actgattgag ctggtgccgt gtcgagtggt gttttttaat 420 aggtttttt actggtaagg ctgactgtta tggctgccgc tgtggaagcg ctgtatgttg 480
ttctggagcg ggagggtgct attttgccta ggcaggaggg tttttcaggt gtttatgtgt 540
ttttctctcc tattaatttt gttatacctc ctatgggggc tgtaatgttg tctctacgcc 600
tgcgggtatg tattcccccg ggctatttcg gtcgcttttt agcactgacc gatgttaacc 660
aacctgatgt gtttaccgag tcttacatta tgactccgga catgaccgag gaactgtcgg 720
tggtgctttt taatcacggt gaccagtttt tttacggtca cgccggcatg gccgtagtcc 780
gtcttatgct tataagggtt gtttttcctg ttgtaagaca ggcttctaat gtttaaatgt 840
ttttttttgt tattttattt tgtgtttaat gcaggaaccc gcagacatgt ttgagagaaa 900
aatggtgtct ttttctgtgg tggttccgga acttacctgc ctttatctgc atgagcatga 960
ctacgatgtg cttgcttttt tgcgcgaggc tttgcctgat tttttgagca gcaccttgca 1020
ttttatatcg ccgcccatgc aacaagctta catagggggct acgctggtta gcatagctcc 1080
gagtatgcgt gtcataatca gtgtgggttc ttttgtcatg gttcctggcg gggaagtggc 1140
cgcgctggtc cgtgcagacc tgcacgatta tgttcagctg gccctgcgaa gggacctacg 1200
ggatcgcggt atttttgtta atgttccgct tttgaatctt atacaggtct gtgaggaacc 1260
tgaatttttg caatcatgat tcgctgcttg aggctgaagg tggagggcgc tctggagcag 1320
atttttacaa tggccggact taatattcgg gatttgctta gagacatatt gataaggtgg 1380

-continued

```
cgagatgaaa attatttggg catggttgaa ggtgctggaa tgtttataga ggagattcac   1440
cctgaagggt ttagccttta cgtccacttg gacgtgaggg cagtttgcct tttggaagcc   1500
attgtgcaac atcttacaaa tgccattatc tgttctttgg ctgtagagtt tgaccacgcc   1560
accggagggg agcgcgttca cttaatagat cttcattttg aggttttgga taatcttttg   1620
gaataaaaaa aaaaaaaaca tggttcttcc agctcttccc gctcctcccg tgtgtgactc   1680
gcagaacgaa tgtgtaggtt ggctgggtgt ggcttattct gcggtggtgg atgttatcag   1740
ggcagcggcg catgaaggag tttacataga acccgaagcc agggggcgcc tggatgcttt   1800
gagagagtgg atatactaca actactacac agagcgagct aagcgacgag accggagacg   1860
cagatctgtt tgtcacgccc gcacctggtt ttgcttcagg aaatatgact acgtccggcg   1920
ttccatttgg catgacacta cgaccaacac gatctcggtt gtctcggcgc actccgtaca   1980
gtagggatcg cctacctcct tttgagacag agacccgcgc taccatactg gaggatcatc   2040
cgctgctgcc cgaatgtaac actttgacaa tgcacaacgt gagttacgtg cgaggtcttc   2100
cctgcagtgt gggatttacg ctgattcagg aatgggttgt tccctgggat atggttctga   2160
cgcgggagga gcttgtaatc ctgaggaagt gtatgcacgt gtgcctgtgt tgtgccaaca   2220
ttgatatcat gacgagcatg atgatccatg gttacgagtc ctgggctctc cactgtcatt   2280
gttccagtcc cggttccctg cagtgcatag ccggcgggca ggttttggcc agctggttta   2340
ggatggtggt ggatggcgcc atgtttaatc agaggtttat atggtaccgg gaggtggtga   2400
attacaacat gccaaaagag gtaatgttta tgtccagcgt gtttatgagg ggtcgccact   2460
taatctacct gcgcttgtgg tatgatggcc acgtgggttc tgtggtcccc gccatgagct   2520
ttggatacag cgccttgcac tgtgggattt tgaacaatat tgtggtgctg tgctgcagtt   2580
actgtgctga tttaagtgag atcagggtgc gctgctgtgc ccggaggaca aggcgtctca   2640
tgctgcgggc ggtgcgaatc atcgctgagg agaccactgc catgttgtat tcctgcagga   2700
cggagcggcg gcggcagcag tttattcgcg cgctgctgca gcaccaccgc cctatcctga   2760
tgcacgatta tgactctacc cccatgtagg cgtggacttc cccttcgccg cccgttgagc   2820
aaccgcaagt tggacagcag cctgtggctc agcagctgga cagcgacatg aacttaagcg   2880
agctgcccgg ggagtttatt aatatcactg atgagcgttt ggctcgacag gaaaccgtgt   2940
ggaatataac acctaagaat atgtctgtta cccatgatat gatgcttttt aaggccagcc   3000
ggggagaaag gactgtgtac tctgtgtgtt gggagggagg tggcaggttg aatactaggg   3060
ttctgtgagt ttgattaagg tacggtgatc aatataagct atgtggtggt ggggctatac   3120
tactgaatga aaaatgactt gaaattttct gcaattgaaa aataaacacg ttgaaacata   3180
acatgcaaca ggttcacgat tctttattcc tgggcaatgt aggagaaggt gtaagagttg   3240
gtagcaaaag tttcagtggt gtattttcca ctttcccagg accatgtaaa agacatagag   3300
taagtgctta cctcgctagt ttctgtggat tcactagtgc cattaagtgt aatggtaagt   3360
atcataggtt tagttttatc accatgcaag taaacttgac tgacaatgtt atttttagca   3420
gtttgacttt gggtttttgg ataggctaga aggttaggca taaatccaac tgcatttgtg   3480
tatggatttg cattagttga gttcccattt ctaaagttcc agtaatgttt tttaagtgag   3540
gagttctcca ttagaacacc gttttggtca aatctaagga atatactaac acttgcaacg   3600
gtgcctgtca tggatgaaag atctccagat acagccaaag cagctacagt agctagtact   3660
tgactcccac attttgtaag aaccaaagta aatttgcagt cattatctga atgaattctg   3720
cagttaggag atgggtctgg ggttgtccac agggtaagtt tgtcatcatt tttgtttcct   3780
```

-continued

```
attgtaatgg cccctgagtt gtcaaagctt aaacccgctc caagtttagt aatcatggca   3840
ccgttttcat tgtaatcaat gccagagcca attttagttt ttattgggtt gatatctgga   3900
gactcagatg tgtttgtatc aaactccaga ccctttcctg catttatagc tatggcagta   3960
ttatcaaagt ttagtccact ggattttttt atgctaactt ccagtttttt agtattgttt   4020
gatgcattaa aaaggtatag gcctctgtta tagtttatgt ccaagttatg agatgcatta   4080
atatacaggg gtccctgccc cagtttaaga cgtagttttg tttgagcatc aaatgggtaa   4140
tccacatcta gaattaacaa gttgttattt atacgcatgc caccgcccgt tttaatttcc   4200
atgttgtttg atgaatcata accaatagct cctgcaactt tggttctaag ggagttttgt   4260
tcaacggtga cacctggtcc agtaactact gttagtgtat cggagttttg tgctacttgc   4320
aaaggaccgc ttattttaat tcctattttt ccattattta cataaatagg atcttccatg   4380
ttaatgccca agctacccgt ggcagtagtt agcgggggtg atgcagttac agtaagggtg   4440
tcgctgtcac tgccagagag gggggctgat gtttgcaggg ctagctttcc atctgacact   4500
gtaatgggcc ctttagtagc aatgcttagt ttggagtctt gcacggtcag tggggcttgt   4560
gactgtacgc taagagcgcc gctagtaact atcagaggag cggtggttgc cactgttagg   4620
gcgcctgagg taattgtaag tggtgcggag gtgtccaaac ttatgtttga ctttgttttt   4680
ttaagtggct gagtaacagt ggttacattt tgggaggtga ggtttccggc cttgtctagg   4740
gtaagaccgc tgcccatttt aagcgcaagc atgccgtggg aggtgtccaa aggttcggag   4800
acgcgtagag agagaactcc aggggggactt tcttggaaac cattgggtga aacaaatgga   4860
ggggtaagaa agggcacagt tggaggcccg gtttctgtgt catatggata cacggggttg   4920
aaggtgtctt cagacggtct ggcgcgtttc atctgcaaca atatgaagat agtgggtgcg   4980
gagggacaag aacatgagga atttgacatc ccatttaaac tttggagaaa gtttgcagct   5040
aaaaggcggc tgagatacca gagttgggag gaaggaaagg aggtgatgct gaataagctg   5100
gacaaagatt tgctgactga ttttaagtaa gtaatttatt gtgtgtttat gttagttgaa   5160
tggaataaga tctctaatac cacacatggt tttaataaga gtgcagaggt cctctggacc   5220
ctgatagggg aagtgcaggc agccctctgt ttctgccgag tgctgggtga cggtgatagg   5280
tttttctccc accataagca ccagtttttg gcgctgggtg ggtagcttgt agctgaggcg   5340
gttgccggta gtggtttttt cgtaggtaag tttggcctgc ttgaccacac aaaagatacc   5400
tcttttacac tggtgtaggt taaccatgtc ttcaacttct tgttttaggc gttctcgctc   5460
ggacgccgcc ttgcgccttt ctagtaggcg ctgttcggtg ttaattccat ccaattctag   5520
atctagagat tcagtcatct ccacctgtca aattaaagta gctaatctca gtgggggtgg   5580
gagaaggggg gcgaggctga ttgattgggg caataacctg ttgcagtggt atgacagcgg   5640
gcactgggaa agtagggtgg ttcatggcat ctatggcatt ccagccaatg tcaaggtatg   5700
gatatatggc tagggcaaaa atggtactgc aaaaaaccat gacagagatg atggcgtata   5760
accaggcttc tgacaaatcg ctctgtttgt tgtagcagct gggaatgttc catatttgag   5820
tgaatctgca ggaaatatgt cttttgggag gcgctgaggt ttgggagcaa agcacaggta   5880
gggcgcaaaa aatcagcaaa acaaaaatga cactccgttt cataattaaa gaattctgag   5940
aagatcagct atagtcctgt ctctgtattg cggatggtgc ctgaggtacg caatgcgcac   6000
acaaacccag tcaatgaact gaatgaaggc gatgactaca gtgacgaggc tgcagatgag   6060
gataagggtg acaaatccgt aaagcaggta aactgtgaaa ggtgggatgc aatctacttc   6120
gatgtgagcg accgcggcca atgtagagca cgcacagaaa agcgcaacaa gggtcaataa   6180
```

-continued

```
tataagaact cgaggaatca tgtctcattt aatcatactg taaaagaaga gaacatggtt   6240
tcagaccgtc caatctatga attttttcat tgtgtgggtt gagcacaatg ataggcctat   6300
agatgggggg tctggcgcgt ctgcgcttta ggcaacaaat aagccacata ataataaggc   6360
aaacaaacat aagcgctatg gaaaaccacc acatgtccaa gctcgcccag tcattgacaa   6420
aggcatgaac ttggggtaaa tttagggcag atgttagtcc ggtagcagtg gtgttgcgat   6480
agtccgttgt gggcgcgatg gttgagccgg tcatctctgg agcaggcaag ctgaagctgg   6540
gtttgatcaa atttgcagtg caggcgctgg cagaaatcag gcgctaacgt ccaggaaagt   6600
ttgatttgaa ggttgtgggt ataatcttgc ccgcctggag catatcccac atagagtaaa   6660
ttgtccaggg gaatacaagc aagcggaaaa tcaaggcatt ttcttttcat caataaaact   6720
gcgtctgctt ttgtatttga gataaagtaa ggtacatacc aaagcaagcg ctgtaataag   6780
cagagcggtg gaacaaaagg tgccagtgtt ctctaaacac ttttgtgggg gccacaactt   6840
gtactgtttg ctcatgtaca tggtaatatc gcacatttca taaaatggaa atttatacat   6900
aaaagtttta cgattttcac cttggaagac tgtgacatta tagtcgttag tgtcacctgg   6960
ctgccaaata gcatatacag catacttgcc aattttgtct ttgtggcgaa taataagctt   7020
ttcatgttct gtggtgcatt ttataagagt agtgcattca ttagcttctg atttaaatgt   7080
aacattgcaa gctggttcct taaactcaac ctttttggca gcgctgcaga ctgccgcaag   7140
ggcgagcaag cctaaaatca tgtacctcat cttggatgtt gcccccagcg tttaaaaagc   7200
tgacaatagg tacaaacgtg cgtgcagcag gcggcaaccc taaggcacag aagtgctagt   7260
ataagaataa acagaattac aagagtaagg ataaccccga ccccaattcc agaaaaatta   7320
gacaagcttg tagagttact tgaattgctc atatacttaa ttaaaaaatc ccagcacccc   7380
gcaaaatgct tttttgacct gagttccggg agttgagctc acctcctgtt ttggaaaaat   7440
gggagtaatg tctggttacg ctcaggctgt aggtgtgggc gcagcaaccg gtgacgcact   7500
cgtacgttcc cggcaggtga ggagggtggt ggtggtggtg tttttcttga cggtgtagtt   7560
gaagccgaga aggttgtgtg gcaaacttac ttcgtctcgc tggaaactgt tgtaaattac   7620
aaatgaagag ccgttaaagt accaggtaag gtacttattg gcccgcttgt gcaaaccgga   7680
ggtgaggttt gctttggtct gctttgggtg ggtaaaaacg gtggcgttca caggatggcg   7740
acaggagccc cagtagattc taatttctgt atttattata ctcagcacag agatgacaac   7800
aaagatcttg atgtaatcca gggttaggac agttgcaaac cacggtcaga acacagggac   7860
cccgctcccg ctccactagc agggggcgct tggtaaactc ccgaatcagg ctacgtgtaa   7920
gctctacctg ggtggtgagc cggacgccgt gcgccgggcc ctcgatatgc tcttcgggca   7980
attcaaagta acaaaactca ccggagccgc gggcaaagca cttgtggcgg cggcagtggt   8040
cgaggtgtgt caggcgcagt cgctctgcct ctccactggt cattcagtcg tagccgtccg   8100
ccgagtcttt caccgcgtca aagttgggaa taaactggtc cgggtagtgg ccgggaggtc   8160
cagaaaaggg gttgaagtaa accgaaggca cgaactcctc aataaattgt agagttccaa   8220
tgcctccgga gcgcggctcc gaggacgagg tctgcagagt taggatcgcc tgacggggcg   8280
taaatgaaga gcggccagcg ccgccgatct gaaatgtccc gtccggacgg agaccaagag   8340
aggagctcac cgactcgtcg ttgagctgaa tacctcgccc tctgattttc aggtgagtta   8400
taccctgccc gggcgaccgc accctgtgac gaaagccgcc cgcaagctgc gcccctgagt   8460
tagtcatctg aacttcggcc tgggcgtctc tgggaagtac cacagtggtg ggagcgggac   8520
tttcctggta caccagggca gcgggccaac tacggggatt aaggttatta cgaggtgtgg   8580
```

-continued

```
tggtaatagc cgcctgttcg aggagaattc ggtttcggtg ggcgcggatt ccgttgaccc   8640
gggatatcat gtggggtccc gcgctcatgt agtttattcg ggttgagtag tcttgggcag   8700
ctccagccgc aagtcccatt tgtggctggt aactccacat gtagggcgtg ggaatttcct   8760
tgctcataat ggcgctgacg acaggtgctg gcgccgggtg tggccgctgg agatgacgta   8820
gttttcgcgc ttaaatttga gaaagggcgc gaaactagtc cttaagagtc agcgcgcagt   8880
atttgctgaa gagagcctcc gcgtcttcca gcgtgcgccg aagctgatct tcgcttttgt   8940
gatacaggca gctgcgggtg agggagcgca gagacctgtt ttttattttc agctcttgtt   9000
cttggcccct gctttgttga aatatagcat acagagtggg aaaaatccta tttctaagct   9060
cgcgggtcga tacgggttcg ttgggcgcca gacgcagcgc tcctcctcct gctgctgccg   9120
ccgctgtgga tttcttgggc tttgtcagag tcttgctatc cggtcgcctt tgcttctgtg   9180
tgaccgctgc tgttgctgcc gctgccgctg ccgccggtgc agtaggggct gtagagatga   9240
cggtagtaat gcaggatgtt acgggggaag gccacgccgt gatggtagag aagaaagcgg   9300
cgggcgaagg agatgttgcc cccacagtct tgcaagcaag caactatggc gttcttgtgc   9360
ccgcgccacg agcggtagcc ttggcgctgt tgttgctctt gggctaacgg cggcggctgc   9420
ttagacttac cggccctggt tccagtggtg tcccatctac ggttgggtcg gcgaacaggc   9480
agtgccggcg gcgcctgagg agcggaggtt gtagcgatgc tgggaacggt tgccaatttc   9540
tggggcgccg gcgaggggaa tgcgaccgag ggtgacggtg tttcgtctga cacctcttcg   9600
gcctcggaag cttcgtctag gctgtcccag tcttccatca tctcctcctc ctcgtccaaa   9660
acctcctctg cctgactgtc ccagtattcc tcctcgtccg tgggtggcgg cggcggcagc   9720
tgcagcttct ttttgggtgc catcctggga agcaagggcc cgcggctgct gatagggctg   9780
cggcggcggg ggattgggt tgagctcctc gccggactgg gggtccaggt aaacccccg    9840
tccctttcgt agcagaaact cttggcgggc tttgttgatg gcttgcaatt ggccaaggat   9900
gtggccctgg gtaatgacgc aggcggtaag ctccgcattt ggcgggcggg attggtcttc   9960
gtagaaccta atctcgtggg cgtggtagtc ctcaggtaca aatttgcgaa ggtaagccga  10020
cgtccacagc cccggagtga gtttcaaccc cggagccgcg gacttttcgt caggcgaggg  10080
accctgcagc tcaaaggtac cgataatttg actttcgcta agcagttgcg aattgcagac  10140
cagggagcgg tgcggggtgc ataggttgca gcgacagtga cactccagta ggccgtcacc  10200
gctcacgtct tccatgatgt cggagtggta ggcaaggtag ttggctagct gcagaaggta  10260
gcagtgaccc caaagcggcg gagggcattc acggtactta atgggcacaa agtcgctagg  10320
aagcgcacag caggtggcgg gcagaattcc tgaacgctct aggataaagt tcctaaagtt  10380
ttgcaacatg ctttgactgg tgaagtctgg cagaccctgt tgcagggttt taagcaggcg  10440
ttcggggaag ataatgtccg ccaggtgcgc ggccacggag cgctcgttga aggccgtcca  10500
taggtccttc aagttttgct ttagcagctt ctgcagctcc tttaggttgc gctcctccag  10560
gcattgctgc cacacgccca tggccgtttg ccaggtgtag cacagaaata agtaaacgca  10620
gtcgcggacg tagtcgcggc gcgcctcgcc cttgagcgtg gaatgaagca cgttttgccc  10680
gaggcggttt tcgtgcaaaa ttccaaggta ggagaccagg ttgcagagct ccacgttgga  10740
aattttgcag gcctggcgca cgtagccctg gcgaaaggtg tagtgcaacg tttcctctag  10800
cttgcgctgc atctccgggt cagcaaagaa ccgctgcatg cactcaagct ccacggtaac  10860
aagcactgcg gccatcatta gcttgcgtcg ctcctccaag tcggcaggct cgcgcgtctc  10920
aagccagcgc gccagctgct catcgccaac tgcgggtagg ccctcctcgg tttgttcttg  10980
```

-continued caagtttgca tccctctcca ggggtcgtgc acggcgcacg atcagctcgc tcatgactgt 11040
gctcataacc ttgggggggta ggttaagtgc cgggtaggca aagtgggtga cctcgatgct 11100
gcgtttcagc acggctaggc gcgcgttgtc accctcaagt tccaccagca ctccacagtg 11160
actttcattt tcgctgtttt cttgttgcag agcgtttgcc gcgcgtttct cgtcgcgtcc 11220
aagaccctca aagatttttg gcacttcgtc gagcgaggcg atatcaggta tgacagcgcc 11280
ctgccgcaag gccagctgct tgtccgctcg gctgcggttg gcacggcagg ataggggtat 11340
cttgcagttt tggaaaaaga tgtgataggt ggcaagcacc tctggcacgg caaatacggg 11400
gtagaagttg aggcgcgggt tgggctcgca tgtgccgttt tcttggcgtt tggggggtac 11460
gcgcggtgag aacaggtggc gttcgtaggc aaggctgaca tccgctatgg cgaggggcac 11520
atcgctgcgc tcttgcaacg cgtcgcagat aatggcgcac tggcgctgca gatgcttcaa 11580
cagcacgtcg tctcccacat ctaggtagtc gccatgcctt tggtcccccc gcccgacttg 11640
ttcctcgttt gcctctgcgt cgtcctggtc ttgcttttta tcctctgttg gtactgagcg 11700
atcctcgtcg tcttcgctta caaaacctgg gtcctgctcg ataatcactt cctcctcctc 11760
aagcgggggt gcctcgacgg ggaaggtggt aggcgcgttg gcggcatcgg tggaggcggt 11820
ggtggcgaac tcaaaggggg cggttaggct gtcctccttc tcgactgact ccatgatctt 11880
tttctgccta taggagaagg aaatggccag tcgggaagag gagcagcgcg aaaccacccc 11940
cgagcgcgga cgcggtgcgg cgcgacgtcc accaaccatg gaggacgtgt cgtccccgtc 12000
gccgtcgccg ccgcctcccc gcgcgccccc aaaaaagcgg ctgaggcggc gtctcgagtc 12060
cgaggacgaa gaagactcgt cacaagatgc gctggtgccg cgcacaccca gcccgcggcc 12120
atcgacctcg acggcggatt tggccattgc gtccaaaaag aaaaagaagc gcccctctcc 12180
caagcccgag cgcccgccat ccccagaggt gatcgtggac agcgaggaag aaagagaaga 12240
tgtggcgcta caaatggtgg gtttcagcaa cccaccggtg ctaatcaagc acggcaaggg 12300
aggtaagcgc acggtgcggc ggctgaatga agacgaccca gtggcgcggg gtatgcggac 12360
gcaagaggaa aaggaagagt ccagtgaagc ggaaagtgaa agcacggtga taaacccgct 12420
gagcctgccg atcgtgtctg cgtgggagaa gggcatggag gctgcgcgcg cgttgatgga 12480
caagtaccac gtggataacg atctaaaggc aaacttcaag ctactgcctg accaagtgga 12540
agctctggcg gccgtatgca agacctggct aaacgaggag caccgcgggt tgcagctgac 12600
cttcaccagc aacaagacct ttgtgacgat gatggggcga ttcctgcagg cgtacctgca 12660
gtcgtttgca gaggtaacct acaagcacca cgagcccacg ggctgcgcgt tgtggctgca 12720
ccgctgcgct gagatcgaag gcgagcttaa gtgtctacac gggagcatta tgataaataa 12780
ggagcacgtg attgaaatgg atgtgacgag cgaaaacggg cagcgcgcgc tgaaggagca 12840
gtctagcaag gccaagatcg tgaagaaccg gtggggccga aatgtggtgc agatctccaa 12900
caccgacgca aggtgctgcg tgcatgacgc ggcctgtccg gccaatcagt tttccggcaa 12960
gtcttgcggc atgttcttct ctgaaggcgc aaaggctcag gtggctttta agcagatcaa 13020
ggctttcatg caggcgctgt atcctaacgc ccagaccggg cacggtcacc ttctgatgcc 13080
actacggtgc gagtgcaact caaagcctgg gcatgcaccc tttttgggaa ggcagctacc 13140
aaagttgact ccgttcgccc tgagcaacgc ggaggacctg gacgcggatc tgatctccga 13200
caagagcgtg ctggccagcg tgcaccaccc ggcgctgata gtgttccagt gctgcaaccc 13260
tgtgtatcgc aactcgcgcg cgcagggcgg aggccccaac tgcgacttca agatatcggc 13320
gcccgacctg ctaaacgcgt tggtgatggt gcgcagcctg tggagtgaaa acttcaccga 13380

-continued

```
gctgccgcgg atggttgtgc ctgagtttaa gtggagcact aaacaccagt atcgcaacgt  13440
gtccctgcca gtggcgcata gcgatgcgcg gcagaacccc tttgattttt aaacggcgca  13500
gacggcaagg gtggggggta aataatcacc cgagagtgta caaataaaaa catttgcctt  13560
tattgaaagt gtctcctagt acattatttt tacatgtttt tcaagtgaca aaaagaagtg  13620
gcgctcctaa tctgcgcact gtggctgcgg aagtagggcg agtggcgctc caggaagctg  13680
tagagctgtt cctggttgcg acgcagggtg ggctgtacct ggggactgtt aagcatggag  13740
ttgggtaccc cggtaataag gttcatggtg gggttgtgat ccatgggagt ttggggccag  13800
ttggcaaagg cgtggagaaa catgcagcag aatagtccac aggcggccga gttgggcccc  13860
tgcacgcttt gggtggactt ttccagcgtt atacagcggt cgggggaaga agcaatggcg  13920
ctacggcgca ggagtgactc gtactcaaac tggtaaacct gcttgagtcg ttggtcagaa  13980
aagccaaagg gctcaaagag gtagcatgtt tttgagcgcg ggttccaggc aaaggccatc  14040
cagtgtacgc cccccagtctc gcgaccggcc gtattgacta tggcgcaggc gagcttgtgt  14100
ggagaaacaa agcctggaaa gcgcttgtca taggtgccca aaaaatatgg cccacaacca  14160
agatctttga caatggcttt cagttcctgc tcactggagc ccatggcggc agctgttgtt  14220
gatgttgctt gcttctttta tgttgtggcg ttgccggccg agaagggcgt gcgcaggtac  14280
acggtctcga tgacgccgcg gtgcggctgg tgcacacgga ccacgtcaaa gacttcaaac  14340
aaaacataaa gaagggtggg ctcgtccatg ggatccacct caaaagtcat gtctagcgcg  14400
tgggcggagt tggcgtagag aaggttttgg cccaggtctg tgagtgcgcc catggacata  14460
aagttactgg agaatgggat gcgccaaagg gtgcgatcgc aaagaaactt tttctgggta  14520
atactgtcaa ccgcggtttt gcctattagt gggtagggca cgttggcggg gtaagcctgt  14580
ccctcgcgca tggtgggagc gaggtagcct acgaatcctg agttgttatg ctggtgaaga  14640
attccaacct gctgatactc cttgtattta gtatcgtcaa ccacttgccg gctcatgggc  14700
tggaagtttc tgaagaacga gtacatgcgg tccttgtagc tttctggaat gtagaagccc  14760
tggtagccaa tattgtagtt ggccaacatc tgcaccagga accagtcctt ggtcatgttg  14820
cactgagcta cgttgtagcc ctccccgtca actgagcgtt taatctcaaa ctcattggga  14880
gtaagcaggc ggtcgttgcc cggccagcta acagaagagt caaaggtaat ggccaccttc  14940
ttaaaggtgt gattaagata gaaggttccg tcaaggtatg gtatggagcc agagtaggtg  15000
tagtaagggt cgtagcctga tcccagggaa ggggtttcct ttgtcttcaa gcgtgtgaag  15060
gcccaaccgc gaaatgctgc ccagttgcgc gatgggatgg agatgggcac gttggtggcg  15120
ttggcgggta tggggtatag catgttggcg gcggaaaggt agtcattaaa ggactggtcg  15180
ttggtgtcat ttctgagcat ggcttccagc gtggaggccg tgttgtgggc catggggaag  15240
aaggtggcgt aaagacaaat gctgtcaaac ttaatgctag ccccgtcaac tctaagatcg  15300
tttcccagag agctctgcag aaccatgtta acatccttcc tgaagttcca ttcatatgta  15360
tatgagcctg gcaggaggag gaggttttta atggcaaaaa acttttgggg cacctgaatg  15420
tgaaagggca cgtagcggcc gtttcccaac aacatggagc gataacggag gcccgcattg  15480
cggtggtggt taaagggatt aacgttgtcc atgtagtcca gagaccagcg cgccccaagg  15540
ttaatgtagc agtctacaag cccgggagcc accactcgct tgttcatgta gtcgtaggtg  15600
ttggggttgt cagatatttc cacattggtg gggttgtatt ttagcttgtc tggcaggtac  15660
agcgcaatat tggagtaaag gaaatttctc cataggttgg catttaggtt aatttccatg  15720
gcaaagttgt tacccactcc tatttcatta cgtgttgcaa aagtttcatc ttttgtccat  15780
```

-continued

```
gtagtatctc cattatcgcc tgagccattg ccattagcct taatagcttg ataggtgtca  15840
gttaccccaa tacccccaag aggaaaacaa taatttggca attcatcctc agttccatgg  15900
ttttcaatga ttctaacatc tggatcatag ctgtctacag cctgattcca catagaaaaa  15960
tatctggttc tatcacctat ggaatcaagc aagagttgat aggacagctc tgtgtttctg  16020
tcttgcaaat ctaccacggc atttagctgc gatgcctgac cagcaagaac acccatgttg  16080
ccagtgctgt tataatacat taggccaata aaattgtccc tgaaagcaat gtaattgggt  16140
ctgtttggca tagattgttg acccaacata gctttagaat tttcatcacc ttttccaggt  16200
ttgtaagaca gatgtgtgtc tggggtttcc atatttacat cttcactgta caaaaccact  16260
tttggtttag tagcattgcc ttgccggtcg ttcaaagagg tagtatttga gaagaattgc  16320
aagtcaacct ttggaagagg cacccctttt tcatccggaa ccagaacgga ttgaccacca  16380
aaaggatttg taggcctggc ataagatcca tagcatggtt tcatgggagt tgttttttta  16440
agcactctcc ctcctgccgc attagcatca gcttcgttcc actgagattc gccaatttga  16500
ggttctggtt gataggaagg atctgcgtat acaggtttag cttgtgtttc tgcattgtct  16560
gatcctattt gtagcccgct ttttgtaatt gtttctccag acaaaggagc ctgggcatag  16620
acatgtgttt tcttagtagc ctgatctcga gcgttttgct cttcttcttc ctcttcttca  16680
tcttcatctt cctcttcttc atcctcggca actgcccggc cgctatcttc ggtttgttcc  16740
cactcacagg agttaggagc gcccttggga gctagagcgt tgtaggcagt gccggagtag  16800
ggcttaaaag taggcccct gtccagcacg ccgcggatgt caaagtacgt ggaagccata  16860
tcaagcacac ggttgtcacc cacagccagg gtgaaccgcg ctttgtacga gtacgcggta  16920
tcctcgcggt ccacagggat gaaccgcagc gtcaaacgct gggaccggtc tgtggttacg  16980
tcgtgcgtag gtgccaccgt ggggtttcta aacttgttat tcaggctgaa gtacgtctcg  17040
gtggcgcggg caaactgcac cagcccgggg ctcaggtact ccgaggcgtc ctggcccgag  17100
atgtgcatgt aagaccactg cggcatcatc gaaggggtag ccatcttgga aagcgggcgc  17160
acggcggctc agcagctcct ctggcggcga catggacgca tacatgacac atacgacacg  17220
ttagctattt agaagcatcg tcggcgcttc agggattgca cccccagacc cacgatgctg  17280
ttcagtgtgc tttgccagtt gccactggct acgggccgca tcgatcgcgg accgctggcg  17340
gcacggcgca gggacgcgcg gctagggcgg gttacaacaa cggcggacgg ccctggcagc  17400
acaggtttct gctgggtgtc agcgggggga ggcaggtcca gcgttacagg tgtgtgctgg  17460
cccagcactc cggtagccat gggcgcgatg ggacgggtgg tgggcaggcc ttgctttagt  17520
gcctcctcgt acgagggagg ctcatctatt tgcgtcacca gagtttcttc cctgtcgggc  17580
cgcggacgct tttcgccacg cccctctgga gacactgtct ccacggccgg tggaggctcc  17640
tctacgggag ggcggggatc aagcttactg ttaatcttat tttgcactgc ctggttggcc  17700
aggtccacca ccccgctaat gccagaggcc aggccatcta ccaccttttg ttggaaattt  17760
tgctctttca acttgtccct cagcatctgg cctgtgctgc tgttccaggc cttgctgcca  17820
tagttcttaa tggtggaacc gaaattttta atgccgctcc acagcgagcc ccagctgaag  17880
gcgccaccgc tcatattgct ggtgccgata tcttgccagt ttcccatgaa cgggcgcgag  17940
ccgtgtcgcg gggccagaga cgcaaagttg atgtcttcca ttctacaaaa tagttacagg  18000
accaagcgag cgtgagactc cagacttttt attttgattt ttccacatgc aacttgtttt  18060
taatcagtgt ctctgcgcct gcaaggccac ggatgcaatt ccgggcacgg cgccaatcgc  18120
cgcggcgatc agtggaataa ggaggggcag gataccgccg cgcatgcgac ggtgcgacgc  18180
```

-continued

```
gcgccgccgc cggtggtgcg cacgacgcat gccgcccgtc aggccgtggc cggccatgcc  18240
cctcctacgg tgcattcttc ctcggaatcc cggcaccggg aaacggaggc ggcaggtgag  18300
ggccatatct gcaagaacca caaagaccgg cttttaaacg atgctggggt ggtagcgcgc  18360
tgttggcagc accagggtcc tgcctccttc gcgagccacc ctgcgcacgg aaatcggggc  18420
cagcacgggc tggcgacggc gacggcggcg gcgggttcca gtggtggttc ggcgtcgggt  18480
agtcgctcgt cttctggggc ggtaggtgta gccacgatag ccgggggtag gcgcgatgga  18540
aggatgtagg gcatattcgg gcagtagtgc gctggcggtg ccgtacttcc tggaacggcg  18600
cgggcgccgg ggggctgaaa cgcgaaacat ccacgggtcc gtttgcacct ccgtagaggt  18660
tttggacgcg gccgcagcgg ccgcctgcac cgcggcatct gccaccgccg aggcaaccgg  18720
ggacgtttgt gtctccatgc cctctgtggc agtggcaata ctagtgctac tggtggtggg  18780
tatctgaacg tccacggtct gcacgcccag tcccggtgcc acctgcttga ttggccgcac  18840
gcggacctcg ggctccagcc caggctccac ggtcattttt tccaagacat cttccagtcg  18900
ctggcgcttg ggtaccatca gctgcacggt gggtgccaag tcaccagact cgcgctttag  18960
gccgcgcttt tcttcggacg gtgcaagcgt gggcagcacc tgctgcagtg tcacgggctt  19020
taggctaggt gttgggttgc cctcgtccag cggcaacgcc aacatgtcct tatgccgctt  19080
tccgtaggca aactccccga ggcgctcgtt ggcctgctca agcaggtcct cgtcgccgta  19140
cacctcatca tacacgcgct tgtaggtgcg ggtggagcgc tcaccgggcg taaaaactac  19200
ggtggtgccg ggtcgcaaaa cacgtcttac gcgtcgacct ttccactgta cccgccgcct  19260
gggcgcggtt gcgtgcagca gttccacctc gtcgtcaagt tcatcatcat catcatcttt  19320
ctttttcttt ttgacccgct ttagctttcg gggcttgtaa tcctgctctt ccttcttcgg  19380
ggggccatag atctccggcg cgatgacctg gagcatctct tctttgattt tgcgcttgga  19440
catagcttcg ttgcgcgccg ccgccgctgg atacatacaa cagtacgagt ctaagtagtt  19500
ttttcttgca atctagttgc gcggggggcg ggtgcgcacg ggcacgcgca ggccgctaac  19560
cgagtcgcgc acccagtaca cgttgcccct gcgaccctga gtcatagcac taatggccgc  19620
ggctgctgcg gcggccgctc gtcgcctgga cctgggggc acagtgacaa tacccgcggc  19680
cagccttcga gcggcccgca tggccgcccg tcggccggtg cgacgtgcgc ggttaagcag  19740
ggccgccgcc gcgcgttggg cggcagtgcc gggtcggcgg cggtggcgac gtgctacgcg  19800
cctccgccgt ctcttcattt tagcataacg ccgggctccg cgcaccacgg tctgaatggc  19860
cgcgtccact gtggacactg gtggcggcgt gggcgtgtag ttgcgcgcct cctccaccac  19920
cgcgtcaatg gcgtcatcga cggtggtgcg cccagtgcgg ccgcgtttgt gcgcgcccca  19980
gggcgcgcgg tagtgcccgc gcacgcgcac tgggtgttgg tcggagcgct tctttgcccc  20040
gccaaacatc ttgcttggga agcgcaggcc ccagcctgtg ttattgctgg gcgatataag  20100
gatggacatg tttgctcaaa aagtgcggct cgataggacg cgcggcgaga ctatgcccag  20160
ggccttgtaa acgtaggggc aggtgcggcg tctggcgtca gtaatggtca ctcgctggac  20220
tcctccgatg ctgttgcgca gcggtagcgt cccgtgatct gtgagagcag gaacgttttc  20280
actgacggtg gtgatggtgg gggctggcgg gcgcgccaaa atctggttct cgggaaagcg  20340
attgaacacg tgggtcagag aggtaaactg gcggatgagc tgggagtaga cggcctggtc  20400
gttgtagaag ctcttggagt gcacgggcaa cagctcggcg cccaccaccg gaaagttgct  20460
gatctggctc gtggagcgga aggtcacggg gtcttgcatc atgtctggca acgaccagta  20520
gacctgctcc gagccgcagg ttacgtcagg agtgcaaagg agggtccatg agcggatccc  20580
```

-continued

```
ggtctgaggg tcgccgtagt tgtatgcaag gtaccagctg cggtactggg tgaaggtgct  20640
gtcattgctt attaggttgt aactgcgttt cttgctgtcc tctgtcaggg gtttgatcac  20700
cggtttcttc tgaggcttct cgacctcggg ttgcgcagcg ggggcggcag cttctgccgc  20760
tgcctcggcc tcagcgcgct tctcctccgc ccgtgtggca aaggtgtcgc cgcgaatggc  20820
atgatcgttc atgtcctcca ccggctgcat tgccgcggct gccgcgttgg agttctcttc  20880
cgcgccgctg ccactgttgt tgccgccgcc tgcgccatcc ccgccctgtt cggtgtcatc  20940
ttttaagctt gcctggtagg cgtccacatc caacagtgcg ggaatgttac caccctccag  21000
gtcatcgtag gtgatcctaa agccctcctg gaagggttgc cgcttgcgga tgcccaacaa  21060
gttgctcagg cggctgtggg tgaagtccac cccgcatcct ggcagcaaaa tgatgtctgg  21120
atggaaggct tcgtttgtat ataccccagg catgacaaga ccagtgactg ggtcaaaccc  21180
cagtctgaag ttgcgggtgt caaactttac cccgatgtcg ctttccagaa ccccgttctg  21240
cctgcccact ttcaagtagt gctccacgat cgcgttgttc ataaggtcta tggtcatggt  21300
ctcggagtag ttgccctcgg gcagcgtgaa ctccacccac tcatatttca gctccacctg  21360
tttgtcctta gtaagcgagc gcgacaccat cacccgcgcc ttaaacttat tggtaaacat  21420
gaactcgttc acatttggca tgttggtatg caggatggtt ttcaggtcgc cgccccagtg  21480
cgaacggtcg tcaagattga tggtctgtgt gcttgcctcc cccgggctgt agtcattgtt  21540
ttgaatgacc gtggttagaa agttgctgtg gtcgttctgg tagttcaggg atgccacatc  21600
cgttgacttg ttgtccacaa ggtacacacg ggtggtgtcg aataggggtg ccaactcaga  21660
gtaacggatg ctgtttctcc ccccggtagg ccgcaggtac cgcggaggca caaacggcgg  21720
gtccagggga gcatcgaagg gggaacccag cgccgccgcc actggcgccg cgctcaccac  21780
gctctcgtag gagggaggag gaccttcctc atacatcgcc gcgcgctgca tactaagggg  21840
aatacaagaa aaccaacgct cggtgccatg gccttggtga gtttttttatt ttgcatcatg  21900
cttttttttt tttttttaa aacattctcc ccagcctggg gcgaaggtgc gcaaacgggt  21960
tgccactccc tcccaaatcc aggacgctgc tgtcgtctgc cgagtcatcg tcctcccaca  22020
ccagaccccg ctgacggtcg tgcctttgac gacgggtggg cgggcgcggg ccgggcacat  22080
ccctgtgctc ctgcgcatac gtcttccatc tactcatctt gtccactagg ctctctatcc  22140
cgttgttggg aaatgccgga ggcaggttct tttcgcgctg cggctgcagc agcgagttgt  22200
ttaggtactc ctcctcgccc agcaggcgcg ggcgggtggt gcgagtgctg gtaaaagacc  22260
ctatcaagct tggaaatggg ctactcgcat ctgaccgcgg ggccgcagcg cctagatcgg  22320
acaagctgct tggcctgcgg aagctttcct ttcgcagcgc cgcctctgcc tgctcgcgct  22380
gttgcaactc tagcagggtc tgcggttgcg gggaaaacac gctgtcgtct atgtcgtccc  22440
agaggaatcc atcgttaccc tcgggcacct caaatccccc ggtgtagaaa ccagggggcg  22500
gtagccagtg cgggttcaag atggcattgg tgaaatactc ggggttcacg gcggccgcgc  22560
gatgcaagta gtccattagg cgattgataa acggccggtt tgaggcatac atgcccggtt  22620
ccatgttgcg cgcggtcatg tccagcgcca cgctgggcgt taccccgtcg cgcatcaggt  22680
taaggctcac gctctgctgc acatagcgca agatgcgctc ctcctcgctg tttaaactgt  22740
gcaacgaggg gatcttctgc cgccggttgg tcagcaggta gttcagggtt gcctccaggc  22800
tgcccgtgtc ctcctgcccc agcgcgcggc tgacacttgt aatctcctgg aaagtatgct  22860
cgtccacatg cgcctgacct atggcctcgc ggtacagtgt cagcaagtga cctaggtatg  22920
tgtcccggga cacgctgcca ctgtccgtga agggcgctat tagcagcagc aacaggcgcg  22980
```

-continued

```
agttgggcgt cagcaagcta gacacggtcg cgcggtcgcc tgtgggagcc cgcacccccc  23040
acagcccctg caagttcttg aaagcctggc tcaggtttac ggtctgcagg ccttgtctac  23100
tggtctggaa aaaatagtct ggcccggact ggtacacctc actttgcggt gtctcagtca  23160
ccattagccg cagtgcgctc acaaagttgg tgtagtcctc ctgtccccgc ggcacgttgg  23220
cgggctgtgt actcaggaag gcgtttagtg caaccatgga gcccaggttg ccctgctgct  23280
gcgcgcgctc acgctgcgcc acggcctcgc gcacatcccc caccagccgg tccaggttgg  23340
tctgcacgtt gccgctgttg taacgagcca cgcgctgaag cagcgcgtcg tagaccaggc  23400
cggcctcatc gggccggatg gccctgtttt cggccagcgc gtttacgatc gccagcacct  23460
tctcgtgcgt ggggtttgcg cgcgccggga ccaccgcttc cagaattgcg gagagccggt  23520
tggcctgcgg ctgctgccgg aacgcgtcag ggttacgcgc agtcagcgac atgatgcggt  23580
ccatgacctg gcgccagtcg tccgtggagt taaggccgga cggctggctc tgcagcgccg  23640
cccgcaccgc cgggtccgtt gcgtcttgca tcatctgatc agaaacatca ccgcttagta  23700
ctcgccgtcc tctggctcgt actcatcgtc ctcgtcatat tcctccacgc cgccgacgtt  23760
gccagcgcgc gcgggtgcca ccgccagccc aggtccggcc ccagctgcct ccagggcgcg  23820
tcggcttggg gcccagcgca ggtcagcgcc cgcgtcaaag taggactcgg cctctctatc  23880
gccgctgccc gtgccagcca gggccctttg caggctgtgc atcagctcgc ggtcgctgag  23940
ctcgcgccgc cggctcacgc tcacggcctt gtggatgcgc tcgttgcgat aaacgcccag  24000
gtcgtcgctc aaggtaagca ccttcaacgc catgcgcatg tagaacccct cgatctttac  24060
ctccttgtct atgggaacgt aaggggtatg gtatatcttg cgggcgtaaa acttgcccag  24120
actgagcatg gaatagttaa tggcggccac cttgtcagcc aggctcaagc tgcgctcctg  24180
caccactatg ctctgcagaa tgtttatcaa atcgagcagc cagcggccct cgggctctac  24240
tatgtttagc agcgcatccc tgaatgcctc gttgtccctg ctgtgctgca ctataaggaa  24300
cagctgcgcc atgagcggct tgctatttgg gttttgctcc agcgcgctta caaagtccca  24360
cagatgcatc agtcctatag ccacctcctc gcgcgccaca agcgtgcgca cgtggttgtt  24420
aaagcttttt tgaaagttaa tctcctggtt caccgtctgc tcgtacgcgg ttaccaggtc  24480
ggcggccgcc acgtgtgcgc gcgcgggact aatcccggtc cgcgcgtcgg gctcaaagtc  24540
ctcctcgcgc agcaaccgct cgcggttcag gccatgccgc aactcgcgcc ctgcgtggaa  24600
ctttcgatcc cgcatctcct cgggctcctc tccctcgcgg tcgcgaaaca ggttctgccg  24660
cggcacgtac gcctcgcgcg tgtcacgctt cagctgcacc cttgggtgtc gctcaggaga  24720
gggcgctcct agccgcgcca ggccctcgcc ctcctccaag tccaggtagt gccgggcccg  24780
gcgccgcggg ggttcgtaat caccatctgc cgccgcgtca gccgcggatg ttgcccctcc  24840
tgacgcggta ggagaagggg agggtgccct gcatgtctgc cgctgctctt gctcttgccg  24900
ctgctgagga gggggcgca tctgccgcag caccggatgc atctgggaaa agcaaaaaag  24960
gggctcgtcc ctgtttccgg aggaatttgc aagcggggtc ttgcatgacg gggaggcaaa  25020
cccccgttcg ccgcagtccg gccggcccga gactcgaacc gggggtcctg cgactcaacc  25080
cttggaaaat aaccctccgg ctacagggag cgagccactt aatgctttcg ctttccagcc  25140
taaccgctta cgccgcgcgc ggccagtggc caaaaaagct agcgcagcag ccgccgcgcc  25200
tggaaggaag ccaaaaggag cgctcccccg ttgtctgacg tcgcacacct gggttcgaca  25260
cgcgggcggt aaccgcatgg atcacggcgg acggccggat ccggggttcg aaccccggtc  25320
gtccgccatg ataccttgc gaatttatcc accagaccac ggaagagtgc ccgcttacag  25380
```

-continued

```
gctctccttt tgcacggtct agagcgtcaa cgactgcgca cgcctcaccg gccagagcgt  25440
cccgaccatg gagcactttt tgccgctgcg caacatctgg aaccgcgtcc gcgactttcc  25500
gcgcgcctcc accaccgccg ccggcatcac ctggatgtcc aggtacatct acggatatca  25560
tcgccttatg ttggaagacc tcgccccccgg agccccggcc accctacgct ggcccctcta  25620
ccgccagccg ccgccgcact ttttggtggg atatcagtac ctggtgcgga cttgcaacga  25680
ctacgtcttt gactcaaggg cttactcgcg tctcaggtac accgagctct cgcagccggg  25740
tcaccagacc gttaactggt ccgttatggc caactgcact tacaccatca acacgggcgc  25800
ataccaccgc tttgtggaca tggatgactt ccagtctacc ctcacgcagg tgcagcaggc  25860
catattagcc gagcgcgttg tcgccgacct ggccctgctt cagccgatga ggggcttcgg  25920
ggtcacacgc atgggaggaa gagggcgcca cctacggcca aactccgccg ccgccgtagc  25980
gatagatgca agagatgcag gacaagagga aggagaagaa gaagtgccgg tagaaaggct  26040
catgcaagac tactacaaag acctgcgccg atgtcaaaac gaagcctggg gcatggccga  26100
ccgcctgcgc attcagcagg ccggacccaa ggacatggtg cttctgtcga ccatccgccg  26160
tctcaagacc gcctacttta attacatcat cagcagcacc tccgccagaa acaaccccga  26220
ccgccacccg ctgccgcccg ccacggtgct cagcctacct tgcgactgtg actggttaga  26280
cgcctttctc gagaggtttt ccgatccggt cgatgcggac tcgctcaggt ccctcggtgg  26340
cggagtacct acacaacaat tgttgagatg catcgttagc gccgtatccc tgccgcacgg  26400
cagccccccg ccaacccata accgggacat gacgggcggc gtcttccaac tgcgcccccg  26460
cgagaacggc cgcgccgtca ccgagaccat gcgccgtcgc cgcggggaga tgatcgagcg  26520
ctttgtcgac cgcctcccgg tgcgccgtcg tcgccgccgt gtcccccctc ccccaccgcc  26580
gccagaagaa gaagaagaag gggaggccct tatggaagag gagattgaag aagaagaggc  26640
ccctgtagcc tttgagcgcg aggtgcgcga cactgtcgcc gagctcatcc gtcttctgga  26700
ggaggagtta accgtgtcgg cgcgcaactc ccagtttttc aacttcgccg tggacttcta  26760
cgaggccatg gagcgccttg aggccttggg ggatatcaac gaatccacgt tgcgacgctg  26820
ggttatgtac ttcttcgtgg cagaacacac cgccaccacc ctcaactacc tctttcagcg  26880
cctgcgaaac tacgccgtct tcgcccggca cgtggagctc aatctcgcgc aggtggtcat  26940
gcgcgcccgc gatgccgaag gggcgtggt ctacagccgc gtctggaacg agggaggcct  27000
caacgccttc tcgcagctca tggcccgcat ctccaacgac ctcgccgcca ccgtggagcg  27060
agccggacgc ggagatctcc aggaggaaga gatcgagcag ttcatggccg aaatcgccta  27120
tcaagacaac tcaggagacg tgcaggagat tttgcgccag gccgccgtca acgacaccga  27180
aattgattct gtcgaactct ctttcaggtt caagctcacc gggcccgtcg tcttcacgca  27240
gaggcgccag attcaggaga tcaaccgccg cgtcgtcgcg ttcgccagca acctccgcgc  27300
gcagcaccag ctcctgcccg cgcgcggcgc cgacgtgccc ctgcccccctc tcccggcggg  27360
tcccgagccc cccctacctc cgggggcccg cccgcgtcac cgcttttaga tgcatcatcc  27420
aaggacaccc ccgcggccca ccgcccgccg cgcggtaccg tagtcgcgcc gcggggatgc  27480
ggcctcttgc aagtcatcga cgccgccacc aaccagcccc tggaaatcag gtatcacctg  27540
gacctagccc gcgccctgac ccggctatgc gaggtaaacc tgcaggagct cccgcctgac  27600
ctgtcgccgc gggagctcca gaccatggac agctcccatc tgcgcgatgt tgtcatcaag  27660
ctccgaccgc cgcgcgcgga catctggact ttgggctcgc gcggcgtggt ggtccgatcc  27720
accataactc ccctcgagca gccagacggt caaggacaag cagccgaagt agaagaccac  27780
```

-continued

```
cagccaaacc cgccaggcga ggggctcaaa ttcccactct gcttccttgt gcgcggtcgt  27840
caggtcaacc tcgtgcagga tgtacagccc gtgcaccgct gccagtactg cgcacgtttt  27900
tacaaaagcc agcacgagtg ttcggcccgt cgcagggact tctactttca ccacatcaac  27960
agccactcct ccaactggtg gcgggagatc cagttcttcc cgatcggctc gcatcctcgc  28020
accgagcgtc tctttgtcac ctacgatgta gagacctata cttggatggg ggcctttggg  28080
aagcagctcg tgcccttcat gctggttatg aagttcggcg gagatgagcc tctggtgacc  28140
gccgcgcgag acctagccgt ggaccttgga tgggaccgct gggaacaaga cccgcttacc  28200
ttctactgca tcaccccaga aaaaatggcc ataggtcgcc agtttaggac ctttcgcgac  28260
cacctgcaaa tgctaatggc ccgtgacctg tggagctcat tcgtcgcttc caaccctcat  28320
cttgcagact gggccctgtc agaacacggg ctcagctccc ctgaggagct cacctacgag  28380
gaacttaaaa aattgccctc catcaagggc accccgcgct tcttggaact ttacatcgtg  28440
ggccacaaca tcaacggctt cgacgagatc gtgctcgccg cccaggtaat taacaaccgt  28500
tccgaggtgc cgggaccctt ccgcatcaca cgcaacttta tgcctcgcgc gggaaagata  28560
cttttcaacg atgtcacctt cgccctgcca aacccgcgtt ccaaaaagcg cacggacttt  28620
ttgctctggg agcagggcgg atgcgacgac actgacttca aataccagta cctcaaagtc  28680
atggttaggg acacctttgc gctcacccac acctcgctcc ggaaggccgc gcaggcatac  28740
gcgctacccg tagaaaaggg atgctgcgcc taccaggccg tcaaccagtt ctacatgcta  28800
ggctcttacc gttcggaggc cgacgggttt ccgatccaag agtactggaa agaccgcgaa  28860
gagtttgtcc tcaaccgcga gctgtggaaa aaaaagggac aggataagta tgacatcatc  28920
aaggaaaccc tggactactg cgccctagac gtgcaggtca ccgccgagct ggtcaacaag  28980
ctgcgcgact cctacgcctc cttcgtgcgt gacgcggtag gtctcacaga cgccagcttc  29040
aacgtcttcc agcgtccaac catatcatcc aactcacatg ccatcttcag gcagatagtc  29100
ttccgagcag agcagcccgc ccgtagcaac ctcggtcccg acctcctcgc tccctcgcac  29160
gaactatacg attacgtgcg cgccagcatc cgcggtggaa gatgctaccc tacatatctt  29220
ggaatactca gagagcccct ctacgtttac gacatttgcg gcatgtacgc ctccgcgctc  29280
acccacccca tgccatgggg tcccccactc aacccatacg agcgcgcgct tgccgcccgc  29340
gcatggcagc aggcgctaga cttgcaagga tgcaagatag actacttcga cgcgcgcctg  29400
ctgcccgggg tctttaccgt ggacgcagac cccccggacg agacgcagct agacccacta  29460
ccgccattct gttcgcgcaa gggcggccgc ctctgctgga ccaacgagcg cctacgcgga  29520
gaggtagcca ccagcgttga ccttgtcacc ctgcacaacc gcggttggcg cgtgcacctg  29580
gtgcccgacg agcgcaccac cgtctttccc gaatggcggt gcgttgcgcg cgaatacgtg  29640
cagctaaaca tcgcggccaa ggagcgcgcc gatcgcgaca aaaaccaaac cctgcgctcc  29700
atcgccaagt tgctgtccaa cgccctctac gggtcgtttg ccaccaagct tgacaacaaa  29760
aagattgtct tttctgacca gatggacgcg gccaccctca aaggcatcac cgcgggccag  29820
gtgaatatca aatcctcctc gtttttggaa actgacaatc ttagcgcaga agtcatgccc  29880
gcttttgaga gggagtactc accccaacag ctggccctcg cagacagcga tgcggaagag  29940
agtgaggacg aacgcgcccc cacccccttt tatagccccc cttcaggaac acccggtcac  30000
gtggcctaca cctataaacc aatcaccttc cttgatgccg aagagggcga catgtgtctt  30060
cacaccctgg agcgagtgga ccccctagtg gacaacgacc gctacccctc ccacttagcc  30120
tccttcgtgc tggcctggac gcgagccttc gtctcagagt ggtccgagtt tctatacgag  30180
```

-continued

```
gaggaccgcg gaacaccgct cgaggacagg cctctcaagt ctgtatacgg ggacacggac  30240
agccttttcg tcaccgagcg tggacaccgg ctcatggaaa ccagaggtaa gaaacgcatc  30300
aaaaagcatg ggggaaacct ggtttttgac cccgaacggc cagagctcac ctggctcgtg  30360
gaatgcgaga ccgtctgcgg ggcctgcggc gcggatgcct actccccgga atcggtattt  30420
ctcgcgccca agctctacgc ccttaaaagt ctgcactgcc cctcgtgcgg cgcctcctcc  30480
aagggcaagc tgcgcgccaa gggccacgcc gcggaggggc tggactatga caccatggtc  30540
aaatgctacc tggccgacgc gcagggcgaa gaccggcagc gcttcagcac cagcaggacc  30600
agcctcaagc gcaccctggc cagcgcgcag cccggagcgc accccttcac cgtgacccag  30660
actacgctga cgaggaccct gcgcccgtgg aaagacatga ccctggcccg tctggacgag  30720
caccgactac tgccgtacag cgaaagccgc cccaacccgc gaaacgagga gatatgctgg  30780
atcgagatgc cgtagagcac gtgaccgagc tgtgggaccg cctggaactg cttggtcaaa  30840
cgctcaaaag catgcctacg gcggacggcc tcaaaccgtt gaaaaacttt gcttccttgc  30900
aagaactgct atcgctgggc ggcgagcgcc ttctggcgca tttggtcagg gaaaacatgc  30960
aagtcaggga catgcttaac gaagtggccc ccctgctcag ggatgacggc agctgcagct  31020
ctcttaacta ccagttgcag ccggtaatag gtgtgattta cgggcccacc ggctgcggta  31080
agtcgcagct gctcaggaac ctgctttctt cccagctgat ctcccctacc ccggaaacgg  31140
ttttcttcat cgccccgcag gtagacatga tcccccccatc tgaactcaaa gcgtgggaaa  31200
tgcaaatctg tgagggtaac tacgcccctg ggccggatgg aaccattata ccgcagtctg  31260
gcaccctccg cccgcgcttt gtaaaaatgg cctatgacga tctcatcctg gaacacaact  31320
atgacgttag tgatcccaga aatatcttcg cccaggccgc cgcccgtggg cccattgcca  31380
tcattatgga cgaatgcatg gaaaatctcg gaggtcacaa gggcgtctcc aagttcttcc  31440
acgcatttcc ttctaagcta catgacaaat ttcccaagtg caccggatac actgtgctgg  31500
tggttctgca caacatgaat ccccggaggg atatggctgg gaacatagcc aacctaaaaa  31560
tacagtccaa gatgcatctc atatccccac gtatgcaccc atcccagctt aaccgctttg  31620
taaacactta caccaagggc ctgcccctgg caatcagctt gctactgaaa gacattttta  31680
ggcaccacgc ccagcgctcc tgctacgact ggatcatcta caacaccacc ccgcagcatg  31740
aagctctgca gtggtgctac ctccacccca gagacgggct tatgcccatg tatctgaaca  31800
tccagagtca cctttaccac gtcctggaaa aaatacacag gaccctcaac gaccgagacc  31860
gctggtcccg ggcctaccgc gcgcgcaaaa cccctaaata aagacagcaa gacacttgct  31920
tgatcaaaat ccaaacagag tctggttttt atttatgttt taaaccgcat tgggagggga  31980
ggaagccttc agggcagaaa cctgctggcg cagatccaac agctgctgag aaacgacatt  32040
aagttcccgg gtcaaagaat ccaattgtgc caaaagagcc gtcaacttgt catcgcgggc  32100
ggatgaacgg gaagctgcac tgcttgcaag cgggctcagg aaagcaaagt cagtcacaat  32160
cccgcgggcg gtggctgcag cggctgaagc ggcggcggag gctgcagtct ccaacggcgt  32220
tccagacacg gtctcgtagg tcaaggtagt agagtttgcg ggcaggacgg ggcgaccatc  32280
aatgctggag cccatcacat tctgacgcac ccccggccat gggggcatgc gcgttgtcaa  32340
atatgagctc acaatgcttc catcaaacga gttggcgctc atggcggcgg ctgctgcaaa  32400
acagatacaa aactacatga gacccccacc ttatatattc tttcccaccc ttaagccccg  32460
cccatcgatg gcaaacagct attatgggta ttatgggtgc tagcgacatg aggttgcccc  32520
gtattcagtg tcgctgattt gtattgtctg aagttgtttt tacgttaagt tgatgcagat  32580
```

-continued

```
caattaatac gatacctgcg tcataattga ttatttgacg tggtttgatg gcctccacgc  32640

acgttgtgat atgtagatga taatcattat cactttacgg gtcctttccg gtgatccgac  32700

aggttacggg gcggcgacct cgcgggtttt cgctatttat gaaaattttc cggtttaagg  32760

cgtttccgtt cttcttcgtc ataacttaat gtttttattt aaaataccct ctgaaaagaa  32820

aggaaacgac aggtgctgaa agcgaggctt tttggcctct gtcgtttcct ttctctgttt  32880

ttgtccgtgg aatgaacaat ggaagttaac ggatccaggc cgcgagcaaa aggccagcaa  32940

aaggccagga accgtaaaaa ggccgcgttg ctggcgtttt tccataggct ccgcccccct  33000

gacgagcatc acaaaaatca acgctcaagt cagaggtggc gaaacccgac aggactataa  33060

agataccagg cgtttccccc tggaagctcc ctcgtgcgct ctcctgttcc gaccctgccg  33120

cttaccggat acctgtccgc ctttctccct tcgggaagcg tggcgctttc tcatagctca  33180

cgctgtaggt atctcagttc ggtgtaggtc gttcgctcca agctgggctg tgtgcacgaa  33240

ccccccgttc agcccgaccg ctgcgcctta tccggtaact atcgtcttga gtccaacccg  33300

gtaagacacg acttatcgcc actggcagca gccactggta acaggattag cagagcgagg  33360

tatgtaggcg gtgctacaga gttcttgaag tggtggccta actacggcta cactagaaga  33420

acagtatttg gtatctgcgc tctgccaaag ccagttacct tcggaaaaag agttggtagc  33480

tcttgatccg gcaaacaaac caccgctggt agcggtggtt tttttgtttg caagcagcag  33540

attacgcgca gaaaaaaagg atctcaagaa gatcctttga tcttttctac ggggtctgac  33600

gctcagtgga acgaaaactc acgttaaggg attttggtca tcagattatc aaaaaggatc  33660

ttcacctaga tccttttaaa ttaaaaatga agttttaaat caatctaaag tatatatgag  33720

taaacttggt ctgacagtta ccaatgctta atcagtgagg cacctatctc agcgatctgt  33780

ctatttcgtt catccatagt tgcctgactc cccgtagtgt agataactac gatacgggag  33840

ggcttaccat ccggccccag tgctgcaatg ataccgcgtg acccacgctc accggctcct  33900

gatttatcag caataaacca gccagccgga agtgccgagc gcagaagtgg tcctgcaact  33960

ttatccgcct ccatccagtc tattagttgt tgccgggaag ctagagtaag tagttcgcca  34020

gttaatagtt ttcgcaacgt tgttgccatt gctacaggca tcgtggtgtc acgctcgtcg  34080

tttggtatgg cttcattcag ctccggttcc caacgatcaa ggcgagttac atgatccccc  34140

atgttgtgca aaaaagcggt tagctccttc ggtcctccga tagttgtcag aagtaagttg  34200

gccgcagtgt tatcactcat ggttatggca gcactgcata attctcttac tgtcatgcca  34260

tccgtaagat gcttttctgt gactggtgag tattcaacca agaatacggg ataataccgc  34320

gccacatagc agaactttaa aagtgctcat cattgggaaa cgttcttcgg ggcgaaaact  34380

ctcaaggatc ttaccgctgt tgagatccag ttcgatgtaa cccactcgcg cacccaagtg  34440

atcttctgca tcttttactt tcaccagcgt ttctgggtga gcaaaaacag gaaggcaaaa  34500

tgccgcaaaa aagggaataa gggcgacacg gaaatgttga atactcatac ttttcctttt  34560

tcaatattat tgaagcattt atcagggtta ttgtctcatc agcggataca tatttg      34616
```

<210> SEQ ID NO 3
<211> LENGTH: 31672
<212> TYPE: DNA
<213> ORGANISM: Artificial Sequence
<220> FEATURE:
<223> OTHER INFORMATION: derived from Adenovirus

<400> SEQUENCE: 3

```
gaatcggcca gcgcgaatta actataacgg tcctaaggta gcgtcatcat cataatatac     60
```

-continued

```
cttattttgg attgaagcca atatgataat gagggggtgg agtttgtgac gtggcgcggg    120
gcgtgggaac ggggcgggtg acgtaggttt tagggcggag taacttgcat gtattgggaa    180
ttgtagtttt tttaaaatgg gaagttacgt atcgtgggaa aacggaagtg aagatttgag    240
gaagttgtgg gtttttggc tttcgtttct gggcgtaggt tcgcgtgcgg ttttctgggt    300
gtttttgtg gactttaacc gttacgtcat tttttagtcc tatatatact cgctctgtac    360
ttggcccttt ttacactgtg actgattgag ctggtgccgt gtcgagtggt gtttttaat    420
aggtttttt actggtaagg ctgactgtta tggctgccgc tgtggaagcg ctgtatgttg    480
ttctggagcg ggagggtgct attttgccta ggcaggaggg tttttcaggt gtttatgtgt    540
ttttctctcc tattaatttt gttatacctc ctatgggggc tgtaatgttg tctctacgcc    600
tgcgggtatg tattcccccg ggctatttcg gtcgcttttt agcactgacc gatgttaacc    660
aacctgatgt gtttaccgag tcttacatta tgactccgga catgaccgag gaactgtcgg    720
tggtgctttt taatcacggt gaccagtttt tttacggtca cgccggcatg gccgtagtcc    780
gtcttatgct tataagggtt gtttttcctg ttgtaagaca ggcttctaat gtttaaatgt    840
ttttttttgt tattttattt tgtgtttaat gcaggaaccc gcagacatgt ttgagagaaa    900
aatggtgtct ttttctgtgg tggttccgga acttacctgc ctttatctgc atgagcatga    960
ctacgatgtg cttgcttttt tgcgcgaggc tttgcctgat tttttgagca gcaccttgca   1020
ttttatatcg ccgcccatgc aacaagctta catagggggct acgctggtta gcatagctcc   1080
gagtatgcgt gtcataatca gtgtgggttc ttttgtcatg gttcctggcg gggaagtggc   1140
cgcgctggtc cgtgcagacc tgcacgatta tgttcagctg gccctgcgaa gggacctacg   1200
ggatcgcggt atttttgtta atgttccgct tttgaatctt atacaggtct gtgaggaacc   1260
tgaatttttg caatcatgat tcgctgcttg aggctgaagg tggagggcgc tctggagcag   1320
atttttacaa tggccggact taatattcgg gatttgctta gagacatatt gataaggtgg   1380
cgagatgaaa attatttggg catggttgaa ggtgctggaa tgtttataga ggagattcac   1440
cctgaagggt ttagccttta cgtccacttg gacgtgaggg cagtttgcct tttggaagcc   1500
attgtgcaac atcttacaaa tgccattatc tgttctttgg ctgtagagtt tgaccacgcc   1560
accggagggg agcgcgttca cttaatagat cttcattttg aggttttgga taatcttttg   1620
gaataaaaaa aaaaaaaaca tggttcttcc agctcttccc gctcctcccg tgtgtgactc   1680
gcagaacgaa tgtgtaggtt ggctgggtgt ggcttattct gcggtggtgg atgttatcag   1740
ggcagcggcg catgaaggag tttacataga acccgaagcc agggggcgcc tggatgcttt   1800
gagagagtgg atatactaca actactacac agagcgagct aagcgacgag accggagacg   1860
cagatctgtt tgtcacgccc gcacctggtt ttgcttcagg aaatatgact acgtccggcg   1920
ttccatttgg catgacacta cgaccaacac gatctcggtt gtctcggcgc actccgtaca   1980
gtagggatcg cctacctcct tttgagacag agacccgcgc taccatactg gaggatcatc   2040
cgctgctgcc cgaatgtaac actttgacaa tgcacaacgt gagttacgtg cgaggtcttc   2100
cctgcagtgt gggatttacg ctgattcagg aatgggttgt tccctgggat atggttctga   2160
cgcgggagga gcttgtaatc ctgaggaagt gtatgcacgt gtgcctgtgt tgtgccaaca   2220
ttgatatcat gacgagcatg atgatccatg gttacgagtc ctgggctctc cactgtcatt   2280
gttccagtcc cggttccctg cagtgcatag ccggcgggca ggttttggcc agctggttta   2340
ggatggtggt ggatggcgcc atgtttaatc agaggtttat atggtaccgg gaggtggtga   2400
attacaacat gccaaaagag gtaatgttta tgtccagcgt gtttatgagg ggtcgccact   2460
```

-continued

```
taatctacct gcgcttgtgg tatgatggcc acgtgggttc tgtggtcccc gccatgagct   2520
ttggatacag cgccttgcac tgtgggattt tgaacaatat tgtggtgctg tgctgcagtt   2580
actgtgctga tttaagtgag atcagggtgc gctgctgtgc ccggaggaca aggcgtctca   2640
tgctgcgggc ggtgcgaatc atcgctgagg agaccactgc catgttgtat tcctgcagga   2700
cggagcggcg gcggcagcag tttattcgcg cgctgctgca gcaccaccgc cctatcctga   2760
tgcacgatta tgactctacc cccatgtagg cgtggacttc cccttcgccg cccgttgagc   2820
aaccgcaagt tggacagcag cctgtggctc agcagctgga cagcgacatg aacttaagcg   2880
agctgcccgg ggagtttatt aatatcactg atgagcgttt ggctcgacag gaaaccgtgt   2940
ggaatataac acctaagaat atgtctgtta cccatgatat gatgcttttt aaggccagcc   3000
ggggagaaag gactgtgtac tctgtgtgtt gggagggagg tggcaggttg aatactaggg   3060
ttctgtgagt ttgattaagg tacggtgatc aatataagct atgtggtggt ggggctatac   3120
tactgaatga aaaatgactt gaaattttct gcaattgaaa aataaacacg ttgaaacata   3180
acatgcaaca ggttcacgat tctttattcc tgggcaatgt aggagaaggt gtaagagttg   3240
gtagcaaaag tttcagtggt gtattttcca ctttcccagg accatgtaaa agacatagag   3300
taagtgctta cctcgctagt ttctgtggat tcactagtgc cattaagtgt aatggtaagt   3360
atcataggtt tagttttatc accatgcaag taaacttgac tgacaatgtt atttttagca   3420
gtttgacttt gggtttttgg ataggctaga aggttaggca taaatccaac tgcatttgtg   3480
tatggatttg cattagttga gttcccattt ctaaagttcc agtaatgttt tttaagtgag   3540
gagttctcca ttagaacacc gttttggtca aatctaagga atatactaac acttgcaacg   3600
gtgcctgtca tggatgaaag atctccagat acagccaaag cagctacagt agctagtact   3660
tgactcccac attttgtaag aaccaaagta aatttgcagt cattatctga atgaattctg   3720
cagttaggag atgggtctgg ggttgtccac agggtaagtt tgtcatcatt tttgtttcct   3780
attgtaatgg cccctgagtt gtcaaagctt aaacccgctc caagtttagt aatcatggca   3840
ccgttttcat tgtaatcaat gccagagcca attttagttt ttattgggtt gatatctgga   3900
gactcagatg tgtttgtatc aaactccaga ccctttcctg catttatagc tatggcagta   3960
ttatcaaagt ttagtccact ggattttttt atgctaactt ccagtttttt agtattgttt   4020
gatgcattaa aaaggtatag gcctctgtta tagtttatgt ccaagttatg agatgcatta   4080
atatacaggg gtccctgccc cagtttaaga cgtagttttg tttgagcatc aaatgggtaa   4140
tccacatcta gaattaacaa gttgttattt atacgcatgc caccgcccgt tttaatttcc   4200
atgttgtttg atgaatcata accaatagct cctgcaactt tggttctaag ggagttttgt   4260
tcaacggtga cacctggtcc agtaactact gttagtgtat cggagttttg tgctacttgc   4320
aaaggaccgc ttattttaat tcctattttt ccattattta cataaatagg atcttccatg   4380
ttaatgccca agctacccgt ggcagtagtt agcgggggtg atgcagttac agtaagggtg   4440
tcgctgtcac tgccagagag gggggctgat gtttgcaggg ctagctttcc atctgacact   4500
gtaatgggcc ctttagtagc aatgcttagt ttggagtctt gcacggtcag tggggcttgt   4560
gactgtacgc taagagcgcc gctagtaact atcagaggag cggtggttgc cactgttagg   4620
gcgcctgagg taattgtaag tggtgcggag gtgtccaaac ttatgtttga ctttgttttt   4680
ttaagtggct gagtaacagt ggttacattt tgggaggtga ggtttccggc cttgtctagg   4740
gtaagaccgc tgcccatttt aagcgcaagc atgccgtggg aggtgtccaa aggttcggag   4800
acgcgtagag agagaactcc agggggactt tcttggaaac cattgggtga aacaaatgga   4860
```

-continued

```
ggggtaagaa agggcacagt tggaggcccg gtttctgtgt catatggata cacggggttg   4920
aaggtgtctt cagacggtct ggcgcgtttc atctgcaaca atatgaagat agtgggtgcg   4980
gagggacaag aacatgagga atttgacatc ccatttaaac tttggagaaa gtttgcagct   5040
aaaaggcggc tgagatacca gagttgggag gaaggaaagg aggtgatgct gaataagctg   5100
gacaaagatt tgctgactga ttttaagtaa gtaatttatt cagtcgtagc cgtccgccga   5160
gtctttcacc gcgtcaaagt tgggaataaa ctggtccggg tagtggccgg gaggtccaga   5220
aaaggggttg aagtaaaccg aaggcacgaa ctcctcaata aattgtagag ttccaatgcc   5280
tccggagcgc ggctccgagg acgaggtctg cagagttagg atcgcctgac ggggcgtaaa   5340
tgaagagcgg ccagcgccgc cgatctgaaa tgtcccgtcc ggacggagac caagagagga   5400
gctcaccgac tcgtcgttga gctgaatacc tcgccctctg attttcaggt gagttatacc   5460
ctgcccgggc gaccgcaccc tgtgacgaaa gccgcccgca agctgcgccc ctgagttagt   5520
catctgaact tcggcctggg cgtctctggg aagtaccaca gtggtgggag cgggactttc   5580
ctggtacacc agggcagcgg gccaactacg gggattaagg ttattacgag gtgtggtggt   5640
aatagccgcc tgttcgagga gaattcggtt tcggtgggcg cggattccgt tgacccggga   5700
tatcatgtgg ggtcccgcgc tcatgtagtt tattcgggtt gagtagtctt gggcagctcc   5760
agccgcaagt cccatttgtg gctggtaact ccacatgtag ggcgtgggaa tttccttgct   5820
cataatggcg ctgacgacag gtgctggcgc cgggtgtggc cgctggagat gacgtagttt   5880
tcgcgcttaa atttgagaaa gggcgcgaaa ctagtcctta agagtcagcg cgcagtattt   5940
gctgaagaga gcctccgcgt cttccagcgt gcgccgaagc tgatcttcgc ttttgtgata   6000
caggcagctg cgggtgaggg agcgcagaga cctgtttttt attttcagct cttgttcttg   6060
gcccctgctt tgttgaaata tagcatacag agtgggaaaa atcctatttc taagctcgcg   6120
ggtcgatacg ggttcgttgg gcgccagacg cagcgctcct cctcctgctg ctgccgccgc   6180
tgtggatttc ttgggctttg tcagagtctt gctatccggt cgcctttgct tctgtgtgac   6240
cgctgctgtt gctgccgctg ccgctgccgc cggtgcagta ggggctgtag agatgacggt   6300
agtaatgcag gatgttacgg gggaaggcca cgccgtgatg gtagagaaga aagcggcggg   6360
cgaaggagat gttgccccca cagtcttgca agcaagcaac tatggcgttc ttgtgcccgc   6420
gccacgagcg gtagccttgg cgctgttgtt gctcttgggc taacggcggc ggctgcttag   6480
acttaccggc cctggttcca gtggtgtccc atctacggtt gggtcggcga acaggcagtg   6540
ccggcggcgc ctgaggagcg gaggttgtag cgatgctggg aacggttgcc aatttctggg   6600
gcgccggcga ggggaatgcg accgagggtg acggtgtttc gtctgacacc tcttcggcct   6660
cggaagcttc gtctaggctg tcccagtctt ccatcatctc ctcctcctcg tccaaaacct   6720
cctctgcctg actgtcccag tattcctcct cgtccgtggg tggcggcggc ggcagctgca   6780
gcttcttttt gggtgccatc ctgggaagca agggcccgcg gctgctgata gggctgcggc   6840
ggcgggggga ttgggttgag ctcctcgccg gactggggt ccaggtaaac cccccgtccc   6900
tttcgtagca gaaactcttg gcgggctttg ttgatggctt gcaattggcc aaggatgtgg   6960
ccctgggtaa tgacgcaggc ggtaagctcc gcatttggcg ggcgggattg gtcttcgtag   7020
aacctaatct cgtgggcgtg gtagtcctca ggtacaaatt tgcgaaggta agccgacgtc   7080
cacagccccg gagtgagttt caaccccgga gccgcggact tttcgtcagg cgagggaccc   7140
tgcagctcaa aggtaccgat aatttgactt tcgctaagca gttgcgaatt gcagaccagg   7200
gagcggtgcg gggtgcatag gttgcagcga cagtgacact ccagtaggcc gtcaccgctc   7260
```

-continued

```
acgtcttcca tgatgtcgga gtggtaggca aggtagttgg ctagctgcag aaggtagcag   7320

tgaccccaaa gcggcggagg gcattcacgg tacttaatgg gcacaaagtc gctaggaagc   7380

gcacagcagg tggcgggcag aattcctgaa cgctctagga taaagttcct aaagttttgc   7440

aacatgcttt gactggtgaa gtctggcaga ccctgttgca gggttttaag caggcgttcg   7500

gggaagataa tgtccgccag gtgcgcggcc acggagcgct cgttgaaggc cgtccatagg   7560

tccttcaagt tttgctttag cagcttctgc agctccttta ggttgcgctc ctccaggcat   7620

tgctgccaca cgcccatggc cgtttgccag gtgtagcaca gaaataagta aacgcagtcg   7680

cggacgtagt cgcggcgcgc ctcgcccttg agcgtggaat gaagcacgtt ttgcccgagg   7740

cggttttcgt gcaaaattcc aaggtaggag accaggttgc agagctccac gttggaaatt   7800

ttgcaggcct ggcgcacgta gccctggcga aaggtgtagt gcaacgtttc ctctagcttg   7860

cgctgcatct ccgggtcagc aaagaaccgc tgcatgcact caagctccac ggtaacaagc   7920

actgcggcca tcattagctt gcgtcgctcc tccaagtcgg caggctcgcg cgtctcaagc   7980

cagcgcgcca gctgctcatc gccaactgcg ggtaggccct cctcggtttg ttcttgcaag   8040

tttgcatccc tctccagggg tcgtgcacgg cgcacgatca gctcgctcat gactgtgctc   8100

ataaccttgg ggggtaggtt aagtgccggg taggcaaagt gggtgacctc gatgctgcgt   8160

ttcagcacgg ctaggcgcgc gttgtcaccc tcaagttcca ccagcactcc acagtgactt   8220

tcattttcgc tgttttcttg ttgcagagcg tttgccgcgc gtttctcgtc gcgtccaaga   8280

ccctcaaaga tttttggcac ttcgtcgagc gaggcgatat caggtatgac agcgccctgc   8340

cgcaaggcca gctgcttgtc cgctcggctg cggttggcac ggcaggatag ggtatcttg    8400

cagttttgga aaaagatgtg ataggtggca agcacctctg gcacggcaaa tacggggtag   8460

aagttgaggc gcgggttggg ctcgcatgtg ccgttttctt ggcgtttggg gggtacgcgc   8520

ggtgagaaca ggtggcgttc gtaggcaagg ctgacatccg ctatggcgag ggcacatcg    8580

ctgcgctctt gcaacgcgtc gcagataatg gcgcactggc gctgcagatg cttcaacagc   8640

acgtcgtctc ccacatctag gtagtcgcca tgcctttggt ccccccgccc gacttgttcc   8700

tcgtttgcct ctgcgtcgtc ctggtcttgc tttttatcct ctgttggtac tgagcgatcc   8760

tcgtcgtctt cgcttacaaa acctgggtcc tgctcgataa tcacttcctc ctcctcaagc   8820

gggggtgcct cgacggggaa ggtggtaggc gcgttggcgg catcggtgga ggcggtggtg   8880

gcgaactcaa agggggcggt taggctgtcc tccttctcga ctgactccat gatcttttc    8940

tgcctatagg agaaggaaat ggccagtcgg gaagaggagc agcgcgaaac cacccccgag   9000

cgcggacgcg gtgcggcgcg acgtccacca accatggagg acgtgtcgtc cccgtcgccg   9060

tcgccgccgc ctccccgcgc gcccccaaaa aagcggctga ggcggcgtct cgagtccgag   9120

gacgaagaag actcgtcaca agatgcgctg gtgccgcgca cacccagccc gcggccatcg   9180

acctcgacgg cggatttggc cattgcgtcc aaaaagaaaa agaagcgccc ctctcccaag   9240

cccgagcgcc cgccatcccc agaggtgatc gtggacagcg aggaagaaag agaagatgtg   9300

gcgctacaaa tggtgggttt cagcaaccca ccggtgctaa tcaagcacgg caagggaggt   9360

aagcgcacgg tgcggcggct gaatgaagac gacccagtgg cgcggggtat gcggacgcaa   9420

gaggaaaagg aagagtccag tgaagcggaa agtgaaagca cggtgataaa cccgctgagc   9480

ctgccgatcg tgtctgcgtg ggagaagggc atggaggctg cgcgcgcgtt gatggacaag   9540

taccacgtgg ataacgatct aaaggcaaac ttcaagctac tgcctgacca agtggaagct   9600

ctggcggccg tatgcaagac ctggctaaac gaggagcacc gcgggttgca gctgaccttc   9660
```

-continued

```
accagcaaca agacctttgt gacgatgatg gggcgattcc tgcaggcgta cctgcagtcg   9720
tttgcagagg taacctacaa gcaccacgag cccacgggct gcgcgttgtg gctgcaccgc   9780
tgcgctgaga tcgaaggcga gcttaagtgt ctacacggga gcattatgat aaataaggag   9840
cacgtgattg aaatggatgt gacgagcgaa aacgggcagc gcgcgctgaa ggagcagtct   9900
agcaaggcca agatcgtgaa gaaccggtgg ggccgaaatg tggtgcagat ctccaacacc   9960
gacgcaaggt gctgcgtgca tgacgcggcc tgtccggcca atcagttttc cggcaagtct  10020
tgcggcatgt tcttctctga aggcgcaaag gctcaggtgg cttttaagca gatcaaggct  10080
ttcatgcagg cgctgtatcc taacgcccag accgggcacg gtcaccttct gatgccacta  10140
cggtgcgagt gcaactcaaa gcctgggcat gcaccctttt tgggaaggca gctaccaaag  10200
ttgactccgt tcgccctgag caacgcggag gacctggacg cggatctgat ctccgacaag  10260
agcgtgctgg ccagcgtgca ccacccggcg ctgatagtgt tccagtgctg caaccctgtg  10320
tatcgcaact cgcgcgcgca gggcggaggc cccaactgcg acttcaagat atcggcgccc  10380
gacctgctaa acgcgttggt gatggtgcgc agcctgtgga gtgaaaactt caccgagctg  10440
ccgcggatgg ttgtgcctga gtttaagtgg agcactaaac accagtatcg caacgtgtcc  10500
ctgccagtgg cgcatagcga tgcgcggcag aacccctttg atttttaaac ggcgcagacg  10560
gcaagggtgg ggggtaaata atcacccgag agtgtacaaa taaaaacatt tgcctttatt  10620
gaaagtgtct cctagtacat tatttttaca tgtttttcaa gtgacaaaaa gaagtggcgc  10680
tcctaatctg cgcactgtgg ctgcggaagt agggcgagtg gcgctccagg aagctgtaga  10740
gctgttcctg gttgcgacgc agggtgggct gtacctgggg actgttaagc atggagttgg  10800
gtaccccggt aataaggttc atggtggggt tgtgatccat gggagtttgg ggccagttgg  10860
caaaggcgtg gagaaacatg cagcagaata gtccacaggc ggccgagttg ggcccctgca  10920
cgctttgggt ggacttttcc agcgttatac agcggtcggg ggaagaagca atggcgctac  10980
ggcgcaggag tgactcgtac tcaaactggt aaacctgctt gagtcgttgg tcagaaaagc  11040
caaagggctc aaagaggtag catgtttttg agcgcgggtt ccaggcaaag gccatccagt  11100
gtacgccccc agtctcgcga ccggccgtat tgactatggc gcaggcgagc ttgtgtggag  11160
aaacaaagcc tggaaagcgc ttgtcatagg tgcccaaaaa atatggccca caaccaagat  11220
ctttgacaat ggctttcagt tcctgctcac tggagcccat ggcggcagct gttgttgatg  11280
ttgcttgctt cttttatgtt gtggcgttgc cggccgagaa gggcgtgcgc aggtacacgg  11340
tctcgatgac gccgcggtgc ggctggtgca cacggaccac gtcaaagact tcaaacaaaa  11400
cataaagaag ggtgggctcg tccatgggat ccacctcaaa agtcatgtct agcgcgtggg  11460
cggagttggc gtagagaagg ttttggccca ggtctgtgag tgcgcccatg gacataaagt  11520
tactggagaa tgggatgcgc caaagggtgc gatcgcaaag aaactttttc tgggtaatac  11580
tgtcaaccgc ggttttgcct attagtgggt agggcacgtt ggcggggtaa gcctgtccct  11640
cgcgcatggt gggagcgagg tagcctacga atcctgagtt gttatgctgg tgaagaattc  11700
caacctgctg atactccttg tatttagtat cgtcaaccac ttgccggctc atgggctgga  11760
agtttctgaa gaacgagtac atgcggtcct tgtagctttc tggaatgtag aagccctggt  11820
agccaatatt gtagttggcc aacatctgca ccaggaacca gtccttggtc atgttgcact  11880
gagctacgtt gtagccctcc ccgtcaactg agcgtttaat ctcaaactca ttgggagtaa  11940
gcaggcggtc gttgcccggc cagctaacag aagagtcaaa ggtaatggcc accttcttaa  12000
aggtgtgatt aagatagaag gttccgtcaa ggtatggtat ggagccagag taggtgtagt  12060
```

-continued

```
aagggtcgta gcctgatccc agggaagggg tttcctttgt cttcaagcgt gtgaaggccc  12120
aaccgcgaaa tgctgcccag ttgcgcgatg ggatggagat gggcacgttg gtggcgttgg  12180
cgggtatggg gtatagcatg ttggcggcgg aaaggtagtc attaaaggac tggtcgttgg  12240
tgtcatttct gagcatggct tccagcgtgg aggccgtgtt gtgggccatg gggaagaagg  12300
tggcgtaaag acaaatgctg tcaaacttaa tgctagcccc gtcaactcta agatcgtttc  12360
ccagagagct ctgcagaacc atgttaacat ccttcctgaa gttccattca tatgtatatg  12420
agcctggcag gaggaggagg tttttaatgg caaaaaactt ttggggcacc tgaatgtgaa  12480
agggcacgta gcggccgttt cccaacaaca tggagcgata acggaggccc gcattgcggt  12540
ggtggttaaa gggattaacg ttgtccatgt agtccagaga ccagcgcgcc ccaaggttaa  12600
tgtagcagtc tacaagcccg ggagccacca ctcgcttgtt catgtagtcg taggtgttgg  12660
ggttgtcaga tatttccaca ttggtggggt tgtattttag cttgtctggc aggtacagcg  12720
caatattgga gtaaaggaaa tttctccata ggttggcatt taggttaatt tccatggcaa  12780
agttgttacc cactcctatt tcattacgtg ttgcaaaagt ttcatctttt gtccatgtag  12840
tatctccatt atcgcctgag ccattgccat tagccttaat agcttgatag gtgtcagtta  12900
ccccaatacc cccaagagga aaacaataat ttggcaattc atcctcagtt ccatggtttt  12960
caatgattct aacatctgga tcatagctgt ctacagcctg attccacata gaaaaatatc  13020
tggttctatc acctatggaa tcaagcaaga gttgatagga cagctctgtg tttctgtctt  13080
gcaaatctac cacggcattt agctgcgatg cctgaccagc aagaacaccc atgttgccag  13140
tgctgttata atacattagg ccaataaaat tgtccctgaa agcaatgtaa ttgggtctgt  13200
ttggcataga ttgttgaccc aacatagctt tagaattttc atcacctttt ccaggtttgt  13260
aagacagatg tgtgtctggg gtttccatat ttacatcttc actgtacaaa accacttttg  13320
gtttagtagc attgccttgc cggtcgttca aagaggtagt atttgagaag aattgcaagt  13380
caacctttgg aagaggcacc ccttttttcat ccggaaccag aacggattga ccaccaaaag  13440
gatttgtagg cctggcataa gatccatagc atggtttcat gggagttgtt tttttaagca  13500
ctctccctcc tgccgcatta gcatcagctt cgttccactg agattcgcca atttgaggtt  13560
ctggttgata ggaaggatct gcgtatacag gtttagcttg tgtttctgca ttgtctgatc  13620
ctatttgtag cccgcttttt gtaattgttt ctccagacaa aggagcctgg gcatagacat  13680
gtgttttctt agtagcctga tctcgagcgt tttgctcttc ttcttcctct tcttcatctt  13740
catcttcctc ttcttcatcc tcggcaactg cccggccgct atcttcggtt tgttcccact  13800
cacaggagtt aggagcgccc ttgggagcta gagcgttgta ggcagtgccg gagtagggct  13860
taaaagtagg ccccctgtcc agcacgccgc ggatgtcaaa gtacgtggaa gccatatcaa  13920
gcacacggtt gtcacccaca gccagggtga accgcgcttt gtacgagtac gcggtatcct  13980
cgcggtccac agggatgaac cgcagcgtca aacgctggga ccggtctgtg gttacgtcgt  14040
gcgtaggtgc caccgtgggg tttctaaact tgttattcag gctgaagtac gtctcggtgg  14100
cgcgggcaaa ctgcaccagc ccggggctca ggtactccga ggcgtcctgg cccgagatgt  14160
gcatgtaaga ccactgcggc atcatcgaag ggtagccat cttggaaagc gggcgcacgg  14220
cggctcagca gctcctctgg cggcgacatg gacgcataca tgacacatac gacacgttag  14280
ctatttagaa gcatcgtcgg cgcttcaggg attgcacccc cagacccacg atgctgttca  14340
gtgtgctttg ccagttgcca ctggctacgg gccgcatcga tcgcggaccg ctggcggcac  14400
ggcgcaggga cgcgcggcta gggcgggtta caacaacggc ggacggccct ggcagcacag  14460
```

-continued

```
gtttctgctg ggtgtcagcg gggggaggca ggtccagcgt tacaggtgtg tgctggccca  14520
gcactccggt agccatgggc gcgatgggac gggtggtggg caggccttgc tttagtgcct  14580
cctcgtacga gggaggctca tctatttgcg tcaccagagt ttcttccctg tcgggccgcg  14640
gacgcttttc gccacgcccc tctggagaca ctgtctccac ggccggtgga ggctcctcta  14700
cgggagggcg gggatcaagc ttactgttaa tcttattttg cactgcctgg ttggccaggt  14760
ccaccacccc gctaatgcca gaggccaggc catctaccac cttttgttgg aaattttgct  14820
ctttcaactt gtccctcagc atctggcctg tgctgctgtt ccaggccttg ctgccatagt  14880
tcttaatggt ggaaccgaaa tttttaatgc cgctccacag cgagccccag ctgaaggcgc  14940
caccgctcat attgctggtg ccgatatctt gccagtttcc catgaacggg cgcgagccgt  15000
gtcgcggggc cagagacgca aagttgatgt cttccattct acaaaatagt tacaggacca  15060
agcgagcgtg agactccaga ctttttattt tgatttttcc acatgcaact tgtttttaat  15120
cagtgtctct gcgcctgcaa ggccacggat gcaattccgg gcacggcgcc aatcgccgcg  15180
gcgatcagtg gaataaggag gggcaggata ccgccgcgca tgcgacggtg cgacgcgcgc  15240
cgccgccggt ggtgcgcacg acgcatgccg cccgtcaggc cgtggccggc catgcccctc  15300
ctacggtgca ttcttcctcg gaatcccggc accgggaaac ggaggcggca ggtgagggcc  15360
atatctgcaa gaaccacaaa gaccggcttt taaacgatgc tggggtggta gcgcgctgtt  15420
ggcagcacca gggtcctgcc tccttcgcga gccaccctgc gcacggaaat cggggccagc  15480
acgggctggc gacggcgacg gcggcggcgg gttccagtgg tggttcggcg tcgggtagtc  15540
gctcgtcttc tggggcggta ggtgtagcca cgatagccgg gggtaggcgc gatggaagga  15600
tgtagggcat attcgggcag tagtgcgctg gcggtgccgt acttcctgga acggcgcggg  15660
cgccgggggg ctgaaacgcg aaacatccac gggtccgttt gcacctccgt agaggttttg  15720
gacgcggccg cagcggccgc ctgcaccgcg gcatctgcca ccgccgaggc aaccggggac  15780
gtttgtgtct ccatgccctc tgtggcagtg gcaatactag tgctactggt ggtgggtatc  15840
tgaacgtcca cggtctgcac gcccagtccc ggtgccacct gcttgattgg ccgcacgcgg  15900
acctcgggct ccagcccagg ctccacggtc atttttttcca agacatcttc cagtcgctgg  15960
cgcttgggta ccatcagctg cacggtgggt gccaagtcac cagactcgcg ctttaggccg  16020
cgcttttctt cggacggtgc aagcgtgggc agcacctgct gcagtgtcac gggctttagg  16080
ctaggtgttg ggttgccctc gtccagcggc aacgccaaca tgtccttatg ccgctttccg  16140
taggcaaact ccccgaggcg ctcgttggcc tgctcaagca ggtcctcgtc gccgtacacc  16200
tcatcataca cgcgcttgta ggtgcgggtg gagcgctcac cgggcgtaaa aactacggtg  16260
gtgccgggtc gcaaaacacg tcttacgcgt cgacctttcc actgtacccg ccgcctgggc  16320
gcggttgcgt gcagcagttc cacctcgtcg tcaagttcat catcatcatc atctttcttt  16380
ttctttttga cccgctttag ctttcggggc ttgtaatcct gctcttcctt cttcgggggg  16440
ccatagatct ccggcgcgat gacctggagc atctcttctt tgattttgcg cttggacata  16500
gcttcgttgc gcgccgccgc cgctggatac atacaacagt acgagtctaa gtagtttttt  16560
cttgcaatct agttgcgcgg ggggcgggtg cgcacgggca cgcgcaggcc gctaaccgag  16620
tcgcgcaccc agtacacgtt gcccctgcga ccctgagtca tagcactaat ggccgcggct  16680
gctgcggcgg ccgctcgtcg cctggacctg gggggcacag tgacaatacc cgcggccagc  16740
cttcgagcgg cccgcatggc cgcccgtcgg ccggtgcgac gtgcgcggtt aagcagggcc  16800
gccgccgcgc gttgggcggc agtgccgggt cggcggcggt ggcgacgtgc tacgcgcctc  16860
```

-continued

```
cgccgtctct tcattttagc ataacgccgg gctccgcgca ccacggtctg aatggccgcg  16920
tccactgtgg acactggtgg cggcgtgggc gtgtagttgc gcgcctcctc caccaccgcg  16980
tcaatggcgt catcgacggt ggtgcgccca gtgcggccgc gtttgtgcgc gccccagggc  17040
gcgcggtagt gcccgcgcac gcgcactggg tgttggtcgg agcgcttctt tgccccgcca  17100
aacatcttgc ttgggaagcg caggccccag cctgtgttat tgctgggcga tataaggatg  17160
gacatgtttg ctcaaaaagt gcggctcgat aggacgcgcg gcgagactat gcccagggcc  17220
ttgtaaacgt aggggcaggt gcggcgtctg gcgtcagtaa tggtcactcg ctggactcct  17280
ccgatgctgt tgcgcagcgg tagcgtcccg tgatctgtga gagcaggaac gttttcactg  17340
acggtggtga tggtgggggc tggcgggcgc gccaaaatct ggttctcggg aaagcgattg  17400
aacacgtggg tcagagaggt aaactggcgg atgagctggg agtagacggc ctggtcgttg  17460
tagaagctct tggagtgcac gggcaacagc tcggcgccca ccaccggaaa gttgctgatc  17520
tggctcgtgg agcggaaggt cacggggtct tgcatcatgt ctggcaacga ccagtagacc  17580
tgctccgagc cgcaggttac gtcaggagtg caaaggaggg tccatgagcg gatcccggtc  17640
tgagggtcgc cgtagttgta tgcaaggtac cagctgcggt actgggtgaa ggtgctgtca  17700
ttgcttatta ggttgtaact gcgtttcttg ctgtcctctg tcaggggttt gatcaccggt  17760
ttcttctgag gcttctcgac ctcgggttgc gcagcggggg cggcagcttc tgccgctgcc  17820
tcggcctcag cgcgcttctc ctccgcccgt gtggcaaagg tgtcgccgcg aatggcatga  17880
tcgttcatgt cctccaccgg ctgcattgcc gcggctgccg cgttggagtt ctcttccgcg  17940
ccgctgccac tgttgttgcc gccgcctgcg ccatccccgc cctgttcggt gtcatctttt  18000
aagcttgcct ggtaggcgtc cacatccaac agtgcgggaa tgttaccacc ctccaggtca  18060
tcgtaggtga tcctaaagcc ctcctggaag ggttgccgct tgcggatgcc caacaagttg  18120
ctcaggcggc tgtgggtgaa gtccaccccg catcctggca gcaaaatgat gtctggatgg  18180
aaggcttcgt ttgtatatac cccaggcatg acaagaccag tgactgggtc aaaccccagt  18240
ctgaagttgc gggtgtcaaa ctttaccccg atgtcgcttt ccagaacccc gttctgcctg  18300
cccactttca agtagtgctc cacgatcgcg ttgttcataa ggtctatggt catggtctcg  18360
gagtagttgc cctcgggcag cgtgaactcc acccactcat atttcagctc cacctgtttg  18420
tccttagtaa gcgagcgcga caccatcacc cgcgccttaa acttattggt aaacatgaac  18480
tcgttcacat ttggcatgtt ggtatgcagg atggttttca ggtcgccgcc ccagtgcgaa  18540
cggtcgtcaa gattgatggt ctgtgtgctt gcctcccccg ggctgtagtc attgttttga  18600
atgaccgtgg ttagaaagtt gctgtggtcg ttctggtagt tcagggatgc cacatccgtt  18660
gacttgttgt ccacaaggta cacacgggtg gtgtcgaata ggggtgccaa ctcagagtaa  18720
cggatgctgt ttctcccccc ggtaggccgc aggtaccgcg gaggcacaaa cggcgggtcc  18780
aggggagcat cgaagggggga acccagcgcc gccgccactg gcgccgcgct caccacgctc  18840
tcgtaggagg gaggaggacc ttcctcatac atcgccgcgc gctgcatact aaggggaata  18900
caagaaaacc aacgctcggt gccatggcct tggtgagttt tttattttgc atcatgcttt  18960
tttttttttt ttttaaaaca ttctccccag cctggggcga aggtgcgcaa acgggttgcc  19020
actccctccc aaatccagga cgctgctgtc gtctgccgag tcatcgtcct cccacaccag  19080
accccgctga cggtcgtgcc tttgacgacg ggtgggcggg cgcgggccgg gcacatccct  19140
gtgctcctgc gcatacgtct tccatctact catcttgtcc actaggctct ctatcccgtt  19200
gttgggaaat gccggaggca ggttcttttc gcgctgcggc tgcagcagcg agttgtttag  19260
```

-continued

```
gtactcctcc tcgcccagca ggcgcgggcg ggtggtgcga gtgctggtaa aagaccctat  19320
caagcttgga aatgggctac tcgcatctga ccgcggggcc gcagcgccta gatcggacaa  19380
gctgcttggc ctgcggaagc tttcctttcg cagcgccgcc tctgcctgct cgcgctgttg  19440
caactctagc agggtctgcg gttgcgggga aaacacgctg tcgtctatgt cgtcccagag  19500
gaatccatcg ttaccctcgg gcacctcaaa tcccccggtg tagaaaccag gggcggtag   19560
ccagtgcggg ttcaagatgg cattggtgaa atactcgggg ttcacggcgg ccgcgcgatg  19620
caagtagtcc attaggcgat tgataaacgg ccggtttgag gcatacatgc ccggttccat  19680
gttgcgcgcg gtcatgtcca gcgccacgct gggcgttacc ccgtcgcgca tcaggttaag  19740
gctcacgctc tgctgcacat agcgcaagat gcgctcctcc tcgctgttta aactgtgcaa  19800
cgaggggatc ttctgccgcc ggttggtcag caggtagttc agggttgcct ccaggctgcc  19860
cgtgtcctcc tgccccagcg cgcggctgac acttgtaatc tcctggaaag tatgctcgtc  19920
cacatgcgcc tgacctatgg cctcgcggta cagtgtcagc aagtgaccta ggtatgtgtc  19980
ccgggacacg ctgccactgt ccgtgaaggg cgctattagc agcagcaaca ggcgcgagtt  20040
gggcgtcagc aagctagaca cggtcgcgcg gtcgcctgtg ggagcccgca ccccccacag  20100
cccctgcaag ttcttgaaag cctggctcag gtttacggtc tgcaggcctt gtctactggt  20160
ctggaaaaaa tagtctggcc cggactggta cacctcactt tgcggtgtct cagtcaccat  20220
tagccgcagt gcgctcacaa agttggtgta gtcctcctgt ccccgcggca cgttggcggg  20280
ctgtgtactc aggaaggcgt ttagtgcaac catggagccc aggttgccct gctgctgcgc  20340
gcgctcacgc tgcgccacgg cctcgcgcac atcccccacc agccggtcca ggttggtctg  20400
cacgttgccg ctgttgtaac gagccacgcg ctgaagcagc gcgtcgtaga ccaggccggc  20460
ctcatcgggc cggatggccc tgttttcggc cagcgcgttt acgatcgcca gcaccttctc  20520
gtgcgtgggg tttgcgcgcg ccgggaccac cgcttccaga attgcggaga gccggttggc  20580
ctgcggctgc tgccggaacg cgtcagggtt acgcgcagtc agcgacatga tgcggtccat  20640
gacctggcgc cagtcgtccg tggagttaag gccggacggc tggctctgca gcgccgcccg  20700
caccgccggg tccgttgcgt cttgcatcat ctgatcagaa acatcaccgc ttagtactcg  20760
ccgtcctctg gctcgtactc atcgtcctcg tcatattcct ccacgccgcc gacgttgcca  20820
gcgcgcgcgg gtgccaccgc cagcccaggt ccggccccag ctgcctccag ggcgcgtcgg  20880
cttggggccc agcgcaggtc agcgcccgcg tcaaagtagg actcggcctc tctatcgccg  20940
ctgcccgtgc cagccagggc cctttgcagg ctgtgcatca gctcgcggtc gctgagctcg  21000
cgccgccggc tcacgctcac ggccttgtgg atgcgctcgt tgcgataaac gcccaggtcg  21060
tcgctcaagg taagcacctt caacgccatg cgcatgtaga acccctcgat ctttacctcc  21120
ttgtctatgg gaacgtaagg ggtatggtat atcttgcggg cgtaaaactt gcccagactg  21180
agcatggaat agttaatggc ggccaccttg tcagccaggc tcaagctgcg ctcctgcacc  21240
actatgctct gcagaatgtt tatcaaatcg agcagccagc ggccctcggg ctctactatg  21300
tttagcagcg catccctgaa tgcctcgttg tccctgctgt gctgcactat aaggaacagc  21360
tgcgccatga gcggcttgct atttgggttt tgctccagcg cgcttacaaa gtcccacaga  21420
tgcatcagtc ctatagccac ctcctcgcgc gccacaagcg tgcgcacgtg gttgttaaag  21480
ctttttttgaa agttaatctc ctggttcacc gtctgctcgt acgcggttac caggtcggcg  21540
gccgccacgt gtgcgcgcgc gggactaatc ccggtccgcg cgtcgggctc aaagtcctcc  21600
tcgcgcagca accgctcgcg gttcaggcca tgccgcaact cgcgccctgc gtggaacttt  21660
```

-continued

```
cgatcccgca tctcctcggg ctcctctccc tcgcggtcgc gaaacaggtt ctgccgcggc  21720
acgtacgcct cgcgcgtgtc acgcttcagc tgcacccttg ggtgtcgctc aggagagggc  21780
gctcctagcc gcgccaggcc ctcgccctcc tccaagtcca ggtagtgccg ggcccggcgc  21840
cgcgggggtt cgtaatcacc atctgccgcc gcgtcagccg cggatgttgc ccctcctgac  21900
gcggtaggag aaggggaggg tgccctgcat gtctgccgct gctcttgctc ttgccgctgc  21960
tgaggagggg ggcgcatctg ccgcagcacc ggatgcatct gggaaaagca aaaaaggggc  22020
tcgtccctgt ttccggagga atttgcaagc ggggtcttgc atgacgggga ggcaaacccc  22080
cgttcgccgc agtccggccg gcccgagact cgaaccgggg gtcctgcgac tcaacccttg  22140
gaaaataacc ctccggctac agggagcgag ccacttaatg ctttcgcttt ccagcctaac  22200
cgcttacgcc gcgcgcggcc agtggccaaa aaagctagcg cagcagccgc cgcgcctgga  22260
aggaagccaa aaggagcgct cccccgttgt ctgacgtcgc acacctgggt tcgacacgcg  22320
ggcggtaacc gcatggatca cggcggacgg ccggatccgg ggttcgaacc ccggtcgtcc  22380
gccatgatac ccttgcgaat ttatccacca gaccacggaa gagtgcccgc ttacaggctc  22440
tccttttgca cggtctagag cgtcaacgac tgcgcacgcc tcaccggcca gagcgtcccg  22500
accatggagc actttttgcc gctgcgcaac atctggaacc gcgtccgcga ctttccgcgc  22560
gcctccacca ccgccgccgg catcacctgg atgtccaggt acatctacgg atatcatcgc  22620
cttatgttgg aagacctcgc ccccggagcc ccggccaccc tacgctggcc cctctaccgc  22680
cagccgccgc cgcacttttt ggtgggatat cagtacctgg tgcggacttg caacgactac  22740
gtctttgact caagggctta ctcgcgtctc aggtacaccg agctctcgca gccgggtcac  22800
cagaccgtta actggtccgt tatggccaac tgcacttaca ccatcaacac gggcgcatac  22860
caccgctttg tggacatgga tgacttccag tctaccctca cgcaggtgca gcaggccata  22920
ttagccgagc gcgttgtcgc cgacctggcc ctgcttcagc cgatgagggg cttcggggtc  22980
acacgcatgg gaggaagagg gcgccaccta cggccaaact ccgccgccgc cgtagcgata  23040
gatgcaagag atgcaggaca agaggaagga gaagaagaag tgccggtaga aaggctcatg  23100
caagactact acaaagacct gcgccgatgt caaaacgaag cctggggcat ggccgaccgc  23160
ctgcgcattc agcaggccgg acccaaggac atggtgcttc tgtcgaccat ccgccgtctc  23220
aagaccgcct actttaatta catcatcagc agcacctccg ccagaaacaa ccccgaccgc  23280
cacccgctgc cgcccgccac ggtgctcagc ctaccttgcg actgtgactg gttagacgcc  23340
tttctcgaga ggttttccga tccggtcgat gcggactcgc tcaggtccct cggtggcgga  23400
gtacctacac aacaattgtt gagatgcatc gttagcgccg tatccctgcc gcacggcagc  23460
cccccgccaa cccataaccg ggacatgacg ggcggcgtct tccaactgcg cccccgcgag  23520
aacggccgcg ccgtcaccga gaccatgcgc cgtcgccgcg gggagatgat cgagcgcttt  23580
gtcgaccgcc tcccggtgcg ccgtcgtcgc cgccgtgtcc cccctccccc accgccgcca  23640
gaagaagaag aagaagggga ggcccttatg gaagaggaga ttgaagaaga agaggcccct  23700
gtagcctttg agcgcgaggt gcgcgacact gtcgccgagc tcatccgtct tctggaggag  23760
gagttaaccg tgtcggcgcg caactcccag tttttcaact tcgccgtgga cttctacgag  23820
gccatggagc gccttgaggc cttgggggat atcaacgaat ccacgttgcg acgctgggtt  23880
atgtacttct tcgtggcaga acacaccgcc accaccctca actacctctt tcagcgcctg  23940
cgaaactacg ccgtcttcgc ccggcacgtg gagctcaatc tcgcgcaggt ggtcatgcgc  24000
gcccgcgatg ccgaaggggg cgtggtctac agccgcgtct ggaacgaggg aggcctcaac  24060
```

-continued

```
gccttctcgc agctcatggc ccgcatctcc aacgacctcg ccgccaccgt ggagcgagcc  24120
ggacgcggag atctccagga ggaagagatc gagcagttca tggccgaaat cgcctatcaa  24180
gacaactcag gagacgtgca ggagattttg cgccaggccg ccgtcaacga caccgaaatt  24240
gattctgtcg aactctcttt caggttcaag ctcaccgggc ccgtcgtctt cacgcagagg  24300
cgccagattc aggagatcaa ccgccgcgtc gtcgcgttcg ccagcaacct ccgcgcgcag  24360
caccagctcc tgcccgcgcg cggcgccgac gtgcccctgc cccctctccc ggcgggtccc  24420
gagcccccc tacctccggg ggcccgcccg cgtcaccgct tttagatgca tcatccaagg  24480
acaccccgc ggcccaccgc ccgccgcgcg gtaccgtagt cgcgccgcgg ggatgcggcc  24540
tcttgcaagt catcgacgcc gccaccaacc agcccctgga aatcaggtat cacctggacc  24600
tagcccgcgc cctgacccgg ctatgcgagg taaacctgca ggagctcccg cctgacctgt  24660
cgccgcggga gctccagacc atggacagct cccatctgcg cgatgttgtc atcaagctcc  24720
gaccgccgcg cgcggacatc tggactttgg gctcgcgcgg cgtggtggtc cgatccacca  24780
taactcccct cgagcagcca gacggtcaag gacaagcagc cgaagtagaa gaccaccagc  24840
caaacccgcc aggcgagggg ctcaaattcc cactctgctt ccttgtgcgc ggtcgtcagg  24900
tcaacctcgt gcaggatgta cagcccgtgc accgctgcca gtactgcgca cgtttttaca  24960
aaagccagca cgagtgttcg gcccgtcgca gggacttcta ctttcaccac atcaacagcc  25020
actcctccaa ctggtggcgg gagatccagt tcttcccgat cggctcgcat cctcgcaccg  25080
agcgtctctt tgtcacctac gatgtagaga cctatacttg gatgggggcc tttgggaagc  25140
agctcgtgcc cttcatgctg gttatgaagt tcggcggaga tgagcctctg gtgaccgccg  25200
cgcgagacct agccgtggac cttggatggg accgctggga acaagacccg cttaccttct  25260
actgcatcac cccagaaaaa atggccatag gtcgccagtt taggaccttt cgcgaccacc  25320
tgcaaatgct aatggcccgt gacctgtgga gctcattcgt cgcttccaac cctcatcttg  25380
cagactgggc cctgtcagaa cacgggctca gctcccctga ggagctcacc tacgaggaac  25440
ttaaaaaatt gccctccatc aagggcaccc cgcgcttctt ggaactttac atcgtgggcc  25500
acaacatcaa cggcttcgac gagatcgtgc tcgccgccca ggtaattaac aaccgttccg  25560
aggtgccggg acccttccgc atcacacgca actttatgcc tcgcgcggga aagatacttt  25620
tcaacgatgt caccttcgcc ctgccaaacc cgcgttccaa aaagcgcacg gactttttgc  25680
tctgggagca gggcggatgc gacgacactg acttcaaata ccagtacctc aaagtcatgg  25740
ttagggacac ctttgcgctc acccacacct cgctccggaa ggccgcgcag gcatacgcgc  25800
tacccgtaga aaagggatgc tgcgcctacc aggccgtcaa ccagttctac atgctaggct  25860
cttaccgttc ggaggccgac gggtttccga tccaagagta ctggaaagac cgcgaagagt  25920
ttgtcctcaa ccgcgagctg tggaaaaaaa agggacagga taagtatgac atcatcaagg  25980
aaaccctgga ctactgcgcc ctagacgtgc aggtcaccgc cgagctggtc aacaagctgc  26040
gcgactccta cgcctccttc gtgcgtgacg cggtaggtct cacagacgcc agcttcaacg  26100
tcttccagcg tccaaccata tcatccaact cacatgccat cttcaggcag atagtcttcc  26160
gagcagagca gcccgcccgt agcaacctcg gtcccgacct cctcgctccc tcgcacgaac  26220
tatacgatta cgtgcgcgcc agcatccgcg gtggaagatg ctaccctaca tatcttggaa  26280
tactcagaga gcccctctac gtttacgaca tttgcggcat gtacgcctcc gcgctcaccc  26340
accccatgcc atggggtccc ccactcaacc catacgagcg cgcgcttgcc gcccgcgcat  26400
ggcagcaggc gctagacttg caaggatgca agatagacta cttcgacgcg cgcctgctgc  26460
```

-continued

```
ccggggtctt taccgtggac gcagaccccc cggacgagac gcagctagac ccactaccgc  26520
cattctgttc gcgcaagggc ggccgcctct gctggaccaa cgagcgccta cgcggagagg  26580
tagccaccag cgttgacctt gtcaccctgc acaaccgcgg ttggcgcgtg cacctggtgc  26640
ccgacgagcg caccaccgtc tttcccgaat ggcggtgcgt tgcgcgcgaa tacgtgcagc  26700
taaacatcgc ggccaaggag cgcgccgatc gcgacaaaaa ccaaaccctg cgctccatcg  26760
ccaagttgct gtccaacgcc ctctacgggt cgtttgccac caagcttgac aacaaaaaga  26820
ttgtcttttc tgaccagatg gacgcggcca ccctcaaagg catcaccgcg ggccaggtga  26880
atatcaaatc ctcctcgttt ttggaaactg acaatcttag cgcagaagtc atgcccgctt  26940
ttgagaggga gtactcaccc caacagctgg ccctcgcaga cagcgatgcg gaagagagtg  27000
aggacgaacg cgcccccacc ccctttttata gcccccccttc aggaacaccc ggtcacgtgg  27060
cctacaccta taaaccaatc accttccttg atgccgaaga gggcgacatg tgtcttcaca  27120
ccctggagcg agtggacccc ctagtggaca acgaccgcta cccctcccac ttagcctcct  27180
tcgtgctggc ctggacgcga gccttcgtct cagagtggtc cgagtttcta tacgaggagg  27240
accgcggaac accgctcgag gacaggcctc tcaagtctgt atacggggac acggacagcc  27300
ttttcgtcac cgagcgtgga caccggctca tggaaaccag aggtaagaaa cgcatcaaaa  27360
agcatggggg aaacctggtt tttgaccccg aacggccaga gctcacctgg ctcgtggaat  27420
gcgagaccgt ctgcggggcc tgcggcgcgg atgcctactc ccggaatcg gtatttctcg  27480
cgcccaagct ctacgccctt aaaagtctgc actgcccctc gtgcggcgcc tcctccaagg  27540
gcaagctgcg cgccaagggc cacgccgcgg aggggctgga ctatgacacc atggtcaaat  27600
gctacctggc cgacgcgcag ggcgaagacc ggcagcgctt cagcaccagc aggaccagcc  27660
tcaagcgcac cctggccagc gcgcagcccg gagcgcaccc cttcaccgtg acccagacta  27720
cgctgacgag gaccctgcgc ccgtggaaag acatgaccct ggcccgtctg gacgagcacc  27780
gactactgcc gtacagcgaa agccgcccca acccgcgaaa cgaggagata tgctggatcg  27840
agatgccgta gagcacgtga ccgagctgtg ggaccgcctg gaactgcttg gtcaaacgct  27900
caaaagcatg cctacggcgg acggcctcaa accgttgaaa aactttgctt ccttgcaaga  27960
actgctatcg ctgggcggcg agcgccttct ggcgcatttg gtcagggaaa acatgcaagt  28020
cagggacatg cttaacgaag tggccccccct gctcagggat gacggcagct gcagctctct  28080
taactaccag ttgcagccgg taataggtgt gatttacggg cccaccggct gcggtaagtc  28140
gcagctgctc aggaacctgc tttcttccca gctgatctcc cctaccccgg aaacggtttt  28200
cttcatcgcc ccgcaggtag acatgatccc cccatctgaa ctcaaagcgt gggaaatgca  28260
aatctgtgag ggtaactacg cccctgggcc ggatggaacc attataccgc agtctggcac  28320
cctccgcccg cgctttgtaa aaatggccta tgacgatctc atcctggaac acaactatga  28380
cgttagtgat cccagaaata tcttcgccca ggccgccgcc cgtgggccca ttgccatcat  28440
tatggacgaa tgcatggaaa atctcggagg tcacaagggc gtctccaagt tcttccacgc  28500
atttccttct aagctacatg acaaatttcc caagtgcacc ggatacactg tgctggtggt  28560
tctgcacaac atgaatcccc ggagggatat ggctgggaac atagccaacc taaaaataca  28620
gtccaagatg catctcatat ccccacgtat gcacccatcc cagcttaacc gctttgtaaa  28680
cacttacacc aagggcctgc ccctggcaat cagcttgcta ctgaaagaca tttttaggca  28740
ccacgcccag cgctcctgct acgactggat catctacaac accaccccgc agcatgaagc  28800
tctgcagtgg tgctacctcc accccagaga cgggcttatg cccatgtatc tgaacatcca  28860
```

-continued

```
gagtcacctt taccacgtcc tggaaaaaat acacaggacc ctcaacgacc gagaccgctg  28920
gtcccgggcc taccgcgcgc gcaaaacccc taaataaaga cagcaagaca cttgcttgat  28980
caaaatccaa acagagtctg gtttttattt atgttttaaa ccgcattggg aggggaggaa  29040
gccttcaggg cagaaacctg ctggcgcaga tccaacagct gctgagaaac gacattaagt  29100
tcccgggtca aagaatccaa ttgtgccaaa agagccgtca acttgtcatc gcgggcggat  29160
gaacgggaag ctgcactgct tgcaagcggg ctcaggaaag caaagtcagt cacaatcccg  29220
cgggcggtgg ctgcagcggc tgaagcggcg gcggaggctg cagtctccaa cggcgttcca  29280
gacacggtct cgtaggtcaa ggtagtagag tttgcgggca ggacggggcg accatcaatg  29340
ctggagccca tcacattctg acgcaccccg gcccatgggg gcatgcgcgt tgtcaaatat  29400
gagctcacaa tgcttccatc aaacgagttg gcgctcatgg cggcggctgc tgcaaaacag  29460
atacaaaact acatgagacc cccaccttat atattctttc ccacccttaa gccccgccca  29520
tcgatggcaa acagctatta tgggtattat gggtgctagc gacatgaggt tgccccgtat  29580
tcagtgtcgc tgatttgtat tgtctgaagt tgtttttacg ttaagttgat gcagatcaat  29640
taatacgata cctgcgtcat aattgattat ttgacgtggt ttgatggcct ccacgcacgt  29700
tgtgatatgt agatgataat cattatcact ttacgggtcc tttccggtga tccgacaggt  29760
tacggggcgg cgacctcgcg ggttttcgct atttatgaaa attttccggt ttaaggcgtt  29820
tccgttcttc ttcgtcataa cttaatgttt ttatttaaaa taccctctga aaagaaagga  29880
aacgacaggt gctgaaagcg aggctttttg gcctctgtcg tttcctttct ctgtttttgt  29940
ccgtggaatg aacaatggaa gttaacggat ccaggccgcg agcaaaaggc cagcaaaagg  30000
ccaggaaccg taaaaaggcc gcgttgctgg cgtttttcca taggctccgc ccccctgacg  30060
agcatcacaa aaatcaacgc tcaagtcaga ggtggcgaaa cccgacagga ctataaagat  30120
accaggcgtt tccccctgga agctccctcg tgcgctctcc tgttccgacc ctgccgctta  30180
ccggatacct gtccgccttt ctcccttcgg gaagcgtggc gctttctcat agctcacgct  30240
gtaggtatct cagttcggtg taggtcgttc gctccaagct gggctgtgtg cacgaacccc  30300
ccgttcagcc cgaccgctgc gccttatccg gtaactatcg tcttgagtcc aacccggtaa  30360
gacacgactt atcgccactg gcagcagcca ctggtaacag gattagcaga gcgaggtatg  30420
taggcggtgc tacagagttc ttgaagtggt ggcctaacta cggctacact agaagaacag  30480
tatttggtat ctgcgctctg ccaaagccag ttaccttcgg aaaaagagtt ggtagctctt  30540
gatccggcaa acaaaccacc gctggtagcg gtggtttttt tgtttgcaag cagcagatta  30600
cgcgcagaaa aaaaggatct caagaagatc ctttgatctt ttctacgggg tctgacgctc  30660
agtggaacga aaactcacgt taagggattt tggtcatcag attatcaaaa aggatcttca  30720
cctagatcct tttaaattaa aaatgaagtt ttaaatcaat ctaaagtata tatgagtaaa  30780
cttggtctga cagttaccaa tgcttaatca gtgaggcacc tatctcagcg atctgtctat  30840
ttcgttcatc catagttgcc tgactccccg tagtgtagat aactacgata cgggagggct  30900
taccatccgg ccccagtgct gcaatgatac cgcgtgaccc acgctcaccg gctcctgatt  30960
tatcagcaat aaaccagcca gccggaagtg ccgagcgcag aagtggtcct gcaactttat  31020
ccgcctccat ccagtctatt agttgttgcc gggaagctag agtaagtagt tcgccagtta  31080
atagttttcg caacgttgtt gccattgcta caggcatcgt ggtgtcacgc tcgtcgtttg  31140
gtatggcttc attcagctcc ggttcccaac gatcaaggcg agttacatga tcccccatgt  31200
tgtgcaaaaa agcggttagc tccttcggtc ctccgatagt tgtcagaagt aagttggccg  31260
```

-continued

```
cagtgttatc actcatggtt atggcagcac tgcataattc tcttactgtc atgccatccg  31320

taagatgctt ttctgtgact ggtgagtatt caaccaagaa tacgggataa taccgcgcca  31380

catagcagaa ctttaaaagt gctcatcatt gggaaacgtt cttcggggcg aaaactctca  31440

aggatcttac cgctgttgag atccagttcg atgtaaccca ctcgcgcacc caagtgatct  31500

tctgcatctt ttactttcac cagcgtttct gggtgagcaa aaacaggaag gcaaaatgcc  31560

gcaaaaaagg gaataagggc gacacggaaa tgttgaatac tcatactttt cctttttcaa  31620

tattattgaa gcatttatca gggttattgt ctcatcagcg gatacatatt tg          31672
```

<210> SEQ ID NO 4
<211> LENGTH: 30365
<212> TYPE: DNA
<213> ORGANISM: Artificial Sequence
<220> FEATURE:
<223> OTHER INFORMATION: derived from Adenovirus

<400> SEQUENCE: 4

```
gaatcggcca gcgcgaatta actataacgg tcctaaggta gcgtcatcat cataatatac     60

cttattttgg attgaagcca atatgataat gaggggggtgg agtttgtgac gtggcgcggg   120

gcgtgggaac ggggcgggtg acgtaggttt tagggcggag taacttgcat gtattgggaa    180

ttgtagtttt tttaaaatgg gaagttacgt atcgtgggaa aacggaagtg aagatttgag    240

gaagttgtgg gtttttttggc tttcgtttct gggcgtaggt tcgcgtgcgg ttttctgggt   300

gtttttttgtg gactttaacc gttacgtcat tttttagtcc tatatatact cgctctgtac   360

ttggcccttt ttacactgtg actgattgag ctggtgccgt gtcgagtggt gttttttaat    420

aggtttttttt actggtaagg ctgactgtta tggctgccgc tgtggaagcg ctgtatgttg   480

ttctggagcg ggagggtgct attttgccta ggataacttc gtataatgta tgctatacga    540

agttatggcg cgccagatct gtttgtcacg cccgcacctg gttttgcttc aggaaatatg    600

actacgtccg gcgttccatt tggcatgaca ctacgaccaa cacgatctcg gttgtctcgg    660

cgcactccgt acagtaggga tcgcctacct ccttttgaga cagagacccg cgctaccata    720

ctggaggatc atccgctgct gcccgaatgt aacactttga caatgcacaa cgtgagttac    780

gtgcgaggtc ttccctgcag tgtgggattt acgctgattc aggaatgggt tgttccctgg    840

gatatggttc tgacgcggga ggagcttgta atcctgagga agtgtatgca cgtgtgcctg    900

tgttgtgcca acattgatat catgacgagc atgatgatcc atggttacga gtcctgggct    960

ctccactgtc attgttccag tcccggttcc ctgcagtgca tagccggcgg gcaggttttg   1020

gccagctggt ttaggatggt ggtggatggc gccatgttta atcagaggtt tatatggtac   1080

cgggaggtgg tgaattacaa catgccaaaa gaggtaatgt ttatgtccag cgtgtttatg   1140

aggggtcgcc acttaatcta cctgcgcttg tggtatgatg gccacgtggg ttctgtggtc   1200

cccgccatga gctttggata cagcgccttg cactgtggga ttttgaacaa tattgtggtg   1260

ctgtgctgca gttactgtgc tgatttaagt gagatcaggg tgcgctgctg tgcccggagg   1320

acaaggcgtc tcatgctgcg ggcggtgcga atcatcgctg aggagaccac tgccatgttg   1380

tattcctgca ggacggagcg gcggcggcag cagtttattc gcgcgctgct gcagcaccac   1440

cgccctatcc tgatgcacga ttatgactct acccccatgt aggcgtggac ttccccttcg   1500

ccgcccgttg agcaaccgca agttggacag cagcctgtgg ctcagcagct ggacagcgac   1560

atgaacttaa gcgagctgcc cggggagttt attaatatca ctgatgagcg tttggctcga   1620

caggaaaccg tgtggaatat aacacctaag aatatgtctg ttacccatga tatgatgctt   1680
```

-continued

```
tttaaggcca gccggggaga aaggactgtg tactctgtgt gttgggaggg aggtggcagg   1740
ttgaatacta gggttctgtg agtttgatta aggtacggtg atcaatataa gctatgtggt   1800
ggtggggcta tactactgaa tgaaaaatga cttgaaattt tctgcaattg aaaaataaac   1860
acgttgaaac ataacatgca acaggttcac gattctttat tcctgggcaa tgtaggagaa   1920
ggtgtaagag ttggtagcaa aagtttcagt ggtgtatttt ccactttccc aggaccatgt   1980
aaaagacata gagtaagtgc ttacctcgct agtttctgtg gattcactag tgccattaag   2040
tgtaatggta agtatcatag gtttagtttt atcaccatgc aagtaaactt gactgacaat   2100
gttattttta gcagtttgac tttgggtttt tggataggct agaaggttag gcataaatcc   2160
aactgcattt gtgtatggat ttgcattagt tgagttccca tttctaaagt tccagtaatg   2220
ttttttaagt gaggagttct ccattagaac accgttttgg tcaaatctaa ggaatatact   2280
aacacttgca acggtgcctg tcatggatga aagatctcca gatacagcca aagcagctac   2340
agtagctagt acttgactcc cacattttgt aagaaccaaa gtaaatttgc agtcattatc   2400
tgaatgaatt ctgcagttag gagatgggtc tggggttgtc cacagggtaa gtttgtcatc   2460
atttttgttt cctattgtaa tggcccctga gttgtcaaag cttaaacccg ctccaagttt   2520
agtaatcatg gcaccgtttt cattgtaatc aatgccagag ccaattttag tttttattgg   2580
gttgatatct ggagactcag atgtgtttgt atcaaactcc agaccctttc ctgcatttat   2640
agctatggca gtattatcaa agtttagtcc actggatttt tttatgctaa cttccagttt   2700
tttagtattg tttgatgcat taaaaaggta taggcctctg ttatagttta tgtccaagtt   2760
atgagatgca ttaatataca ggggtccctg ccccagttta agacgtagtt ttgtttgagc   2820
atcaaatggg taatccacat ctagaattaa caagttgtta tttatacgca tgccaccgcc   2880
cgttttaatt tccatgttgt ttgatgaatc ataaccaata gctcctgcaa ctttggttct   2940
aagggagttt tgttcaacgg tgacacctgg tccagtaact actgttagtg tatcggagtt   3000
ttgtgctact tgcaaaggac cgcttatttt aattcctatt tttccattat ttacataaat   3060
aggatcttcc atgttaatgc ccaagctacc cgtggcagta gttagcgggg gtgatgcagt   3120
tacagtaagg gtgtcgctgt cactgccaga gagggggggct gatgtttgca gggctagctt   3180
tccatctgac actgtaatgg gccctttagt agcaatgctt agtttggagt cttgcacggt   3240
cagtggggct tgtgactgta cgctaagagc gccgctagta actatcagag gagcggtggt   3300
tgccactgtt agggcgcctg aggtaattgt aagtggtgcg gaggtgtcca aacttatgtt   3360
tgactttgtt tttttaagtg gctgagtaac agtggttaca ttttgggagg tgaggtttcc   3420
ggccttgtct agggtaagac cgctgcccat tttaagcgca agcatgccgt gggaggtgtc   3480
caaaggttcg gagacgcgta gagagagaac tccaggggga ctttcttgga aaccattggg   3540
tgaaacaaat ggaggggtaa gaaagggcac agttggaggc ccggtttctg tgtcatatgg   3600
atacacgggg ttgaaggtgt cttcagacgg tctggcgcgt ttcatctgca acaatatgaa   3660
gatagtgggt gcggagggac aagaacatga ggaatttgac atcccattta aactttggag   3720
aaagtttgca gctaaaaggc ggctgagata ccagagttgg gaggaaggaa aggaggtgat   3780
gctgaataag ctggacaaag atttgctgac tgattttaag taagtaattt attcagtcgt   3840
agccgtccgc cgagtctttc accgcgtcaa agttgggaat aaactggtcc gggtagtggc   3900
cgggaggtcc agaaaagggg ttgaagtaaa ccgaaggcac gaactcctca ataaattgta   3960
gagttccaat gcctccggag cgcggctccg aggacgaggt ctgcagagtt aggatcgcct   4020
gacggggcgt aaatgaagag cggccagcgc cgccgatctg aaatgtcccg tccggacgga   4080
```

-continued gaccaagaga ggagctcacc gactcgtcgt tgagctgaat acctcgccct ctgattttca 4140
ggtgagttat accctgcccg ggcgaccgca ccctgtgacg aaagccgccc gcaagctgcg 4200
cccctgagtt agtcatctga acttcggcct gggcgtctct gggaagtacc acagtggtgg 4260
gagcgggact ttcctggtac accagggcag cgggccaact acggggatta aggttattac 4320
gaggtgtggt ggtaatagcc gcctgttcga ggagaattcg gtttcggtgg gcgcggattc 4380
cgttgacccg ggatatcatg tggggtcccg cgctcatgta gtttattcgg gttgagtagt 4440
cttgggcagc tccagccgca agtcccattt gtggctggta actccacatg tagggcgtgg 4500
gaatttcctt gctcataatg gcgctgacga caggtgctgg cgccgggtgt ggccgctgga 4560
gatgacgtag ttttcgcgct taaatttgag aaagggcgcg aaactagtcc ttaagagtca 4620
gcgcgcagta tttgctgaag agagcctccg cgtcttccag cgtgcgccga agctgatctt 4680
cgcttttgtg atacaggcag ctgcgggtga gggagcgcag agacctgttt tttattttca 4740
gctcttgttc ttggcccctg ctttgttgaa atatagcata cagagtggga aaaatcctat 4800
ttctaagctc gcgggtcgat acgggttcgt tgggcgccag acgcagcgct cctcctcctg 4860
ctgctgccgc cgctgtggat ttcttgggct ttgtcagagt cttgctatcc ggtcgccttt 4920
gcttctgtgt gaccgctgct gttgctgccg ctgccgctgc cgccggtgca gtaggggctg 4980
tagagatgac ggtagtaatg caggatgtta cgggggaagg ccacgccgtg atggtagaga 5040
agaaagcggc gggcgaagga gatgttgccc ccacagtctt gcaagcaagc aactatggcg 5100
ttcttgtgcc cgcgccacga gcggtagcct tggcgctgtt gttgctcttg ggctaacggc 5160
ggcggctgct tagacttacc ggccctggtt ccagtggtgt cccatctacg gttgggtcgg 5220
cgaacaggca gtgccggcgg cgcctgagga gcggaggttg tagcgatgct gggaacggtt 5280
gccaatttct ggggcgccgg cgaggggaat gcgaccgagg gtgacggtgt ttcgtctgac 5340
acctcttcgg cctcggaagc ttcgtctagg ctgtcccagt cttccatcat ctcctcctcc 5400
tcgtccaaaa cctcctctgc ctgactgtcc cagtattcct cctcgtccgt gggtggcggc 5460
ggcggcagct gcagcttctt tttgggtgcc atcctgggaa gcaagggccc gcggctgctg 5520
atagggctgc ggcggcgggg ggattgggtt gagctcctcg ccggactggg ggtccaggta 5580
aaccccccgt ccctttcgta gcagaaactc ttggcgggct ttgttgatgg cttgcaattg 5640
gccaaggatg tggccctggg taatgacgca ggcggtaagc tccgcatttg gcgggcggga 5700
ttggtcttcg tagaacctaa tctcgtgggc gtggtagtcc tcaggtacaa atttgcgaag 5760
gtaagccgac gtccacagcc ccggagtgag tttcaacccc ggagccgcgg acttttcgtc 5820
aggcgaggga ccctgcagct caaaggtacc gataatttga ctttcgctaa gcagttgcga 5880
attgcagacc agggagcggt gcggggtgca taggttgcag cgacagtgac actccagtag 5940
gccgtcaccg ctcacgtctt ccatgatgtc ggagtggtag gcaaggtagt tggctagctg 6000
cagaaggtag cagtgacccc aaagcggcgg agggcattca cggtacttaa tgggcacaaa 6060
gtcgctagga agcgcacagc aggtggcggg cagaattcct gaacgctcta ggataaagtt 6120
cctaaagttt tgcaacatgc tttgactggt gaagtctggc agaccctgtt gcagggtttt 6180
aagcaggcgt tcggggaaga taatgtccgc caggtgcgcg gccacggagc gctcgttgaa 6240
ggccgtccat aggtccttca agttttgctt tagcagcttc tgcagctcct ttaggttgcg 6300
ctcctccagg cattgctgcc acacgcccat ggccgtttgc caggtgtagc acagaaataa 6360
gtaaacgcag tcgcggacgt agtcgcggcg cgcctcgccc ttgagcgtgg aatgaagcac 6420
gttttgcccg aggcggtttt cgtgcaaaat tccaaggtag gagaccaggt tgcagagctc 6480

-continued

```
cacgttggaa attttgcagg cctggcgcac gtagccctgg cgaaaggtgt agtgcaacgt   6540
ttcctctagc ttgcgctgca tctccgggtc agcaaagaac cgctgcatgc actcaagctc   6600
cacggtaaca agcactgcgg ccatcattag cttgcgtcgc tcctccaagt cggcaggctc   6660
gcgcgtctca agccagcgcg ccagctgctc atcgccaact gcgggtaggc cctcctcggt   6720
ttgttcttgc aagtttgcat ccctctccag ggtcgtgca cggcgcacga tcagctcgct   6780
catgactgtg ctcataacct tggggggtag gttaagtgcc gggtaggcaa agtgggtgac   6840
ctcgatgctg cgtttcagca cggctaggcg cgcgttgtca ccctcaagtt ccaccagcac   6900
tccacagtga ctttcatttt cgctgttttc ttgttgcaga gcgtttgccg cgcgtttctc   6960
gtcgcgtcca agaccctcaa agatttttgg cacttcgtcg agcgaggcga tatcaggtat   7020
gacagcgccc tgccgcaagg ccagctgctt gtccgctcgg ctgcggttgg cacggcagga   7080
taggggtatc ttgcagtttt ggaaaaagat gtgataggtg gcaagcacct ctggcacggc   7140
aaatacgggg tagaagttga ggcgcgggtt gggctcgcat gtgccgtttt cttggcgttt   7200
ggggggtacg cgcggtgaga acaggtggcg ttcgtaggca aggctgacat ccgctatggc   7260
gaggggcaca tcgctgcgct cttgcaacgc gtcgcagata atggcgcact ggcgctgcag   7320
atgcttcaac agcacgtcgt ctcccacatc taggtagtcg ccatgccttt ggtccccccg   7380
cccgacttgt tcctcgtttg cctctgcgtc gtcctggtct tgctttttat cctctgttgg   7440
tactgagcga tcctcgtcgt cttcgcttac aaaacctggg tcctgctcga taatcacttc   7500
ctcctcctca agcgggggtg cctcgacggg gaaggtggta ggcgcgttgg cggcatcggt   7560
ggaggcggtg gtggcgaact caaaggggc ggttaggctg tcctccttct cgactgactc   7620
catgatcttt ttctgcctat aggagaagga aatggccagt cgggaagagg agcagcgcga   7680
aaccaccccc gagcgcggac gcggtgcggc gcgacgtcca ccaaccatgg aggacgtgtc   7740
gtccccgtcg ccgtcgccgc cgcctccccg cgcgccccca aaaaagcggc tgaggcggcg   7800
tctcgagtcc gaggacgaag aagactcgtc acaagatgcg ctggtgccgc gcacacccag   7860
cccgcggcca tcgacctcga cggcggattt ggccattgcg tccaaaaaga aaaagaagcg   7920
cccctctccc aagcccgagc gcccgccatc cccagaggtg atcgtggaca gcgaggaaga   7980
aagagaagat gtggcgctac aaatggtggg tttcagcaac ccaccggtgc taatcaagca   8040
cggcaaggga ggtaagcgca cggtgcggcg gctgaatgaa gacgacccag tggcgcgggg   8100
tatgcggacg caagaggaaa aggaagagtc cagtgaagcg gaaagtgaaa gcacggtgat   8160
aaacccgctg agcctgccga tcgtgtctgc gtgggagaag ggcatggagg ctgcgcgcgc   8220
gttgatggac aagtaccacg tggataacga tctaaaggca aacttcaagc tactgcctga   8280
ccaagtggaa gctctggcgg ccgtatgcaa gacctggcta aacgaggagc accgcgggtt   8340
gcagctgacc ttcaccagca acaagacctt tgtgacgatg atggggcgat tcctgcaggc   8400
gtacctgcag tcgtttgcag aggtaaccta caagcaccac gagcccacgg gctgcgcgtt   8460
gtggctgcac cgctgcgctg agatcgaagg cgagcttaag tgtctacacg ggagcattat   8520
gataaataag gagcacgtga ttgaaatgga tgtgacgagc gaaaacgggc agcgcgcgct   8580
gaaggagcag tctagcaagg ccaagatcgt gaagaaccgg tggggccgaa atgtggtgca   8640
gatctccaac accgacgcaa ggtgctgcgt gcatgacgcg gcctgtccgg ccaatcagtt   8700
ttccggcaag tcttgcggca tgttcttctc tgaaggcgca aaggctcagg tggcttttaa   8760
gcagatcaag gctttcatgc aggcgctgta tcctaacgcc cagaccgggc acggtcacct   8820
tctgatgcca ctacggtgcg agtgcaactc aaagcctggg catgcaccct ttttgggaag   8880
```

-continued

```
gcagctacca aagttgactc cgttcgccct gagcaacgcg gaggacctgg acgcggatct   8940
gatctccgac aagagcgtgc tggccagcgt gcaccacccg gcgctgatag tgttccagtg   9000
ctgcaaccct gtgtatcgca actcgcgcgc gcagggcgga ggccccaact gcgacttcaa   9060
gatatcggcg cccgacctgc taaacgcgtt ggtgatggtg cgcagcctgt ggagtgaaaa   9120
cttcaccgag ctgccgcgga tggttgtgcc tgagtttaag tggagcacta aacaccagta   9180
tcgcaacgtg tccctgccag tggcgcatag cgatgcgcgg cagaacccct ttgattttta   9240
aacggcgcag acggcaaggg tgggggtaa ataatcaccc gagagtgtac aaataaaaac   9300
atttgccttt attgaaagtg tctcctagta cattattttt acatgttttt caagtgacaa   9360
aaagaagtgg cgctcctaat ctgcgcactg tggctgcgga agtagggcga gtggcgctcc   9420
aggaagctgt agagctgttc ctggttgcga cgcagggtgg gctgtacctg gggactgtta   9480
agcatggagt tgggtacccc ggtaataagg ttcatggtgg ggttgtgatc catgggagtt   9540
tggggccagt tggcaaaggc gtggagaaac atgcagcaga atagtccaca ggcggccgag   9600
ttgggcccct gcacgctttg ggtggacttt tccagcgtta tacagcggtc gggggaagaa   9660
gcaatggcgc tacggcgcag gagtgactcg tactcaaact ggtaaacctg cttgagtcgt   9720
tggtcagaaa agccaaaggg ctcaaagagg tagcatgttt ttgagcgcgg gttccaggca   9780
aaggccatcc agtgtacgcc cccagtctcg cgaccggccg tattgactat ggcgcaggcg   9840
agcttgtgtg gagaaacaaa gcctggaaag cgcttgtcat aggtgcccaa aaaatatggc   9900
ccacaaccaa gatctttgac aatggctttc agttcctgct cactggagcc catggcggca   9960
gctgttgttg atgttgcttg cttcttttat gttgtggcgt tgccggccga gaagggcgtg  10020
cgcaggtaca cggtctcgat gacgccgcgg tgcggctggt gcacacggac cacgtcaaag  10080
acttcaaaca aaacataaag aagggtgggc tcgtccatgg gatccacctc aaaagtcatg  10140
tctagcgcgt gggcggagtt ggcgtagaga aggttttggc ccaggtctgt gagtgcgccc  10200
atggacataa agttactgga gaatgggatg cgccaaaggg tgcgatcgca aagaaacttt  10260
ttctgggtaa tactgtcaac cgcggttttg cctattagtg ggtagggcac gttggcgggg  10320
taagcctgtc cctcgcgcat ggtgggagcg aggtagccta cgaatcctga gttgttatgc  10380
tggtgaagaa ttccaacctg ctgatactcc ttgtatttag tatcgtcaac cacttgccgg  10440
ctcatgggct ggaagtttct gaagaacgag tacatgcggt ccttgtagct ttctggaatg  10500
tagaagccct ggtagccaat attgtagttg gccaacatct gcaccaggaa ccagtccttg  10560
gtcatgttgc actgagctac gttgtagccc tccccgtcaa ctgagcgttt aatctcaaac  10620
tcattgggag taagcaggcg gtcgttgccc ggccagctaa cagaagagtc aaaggtaatg  10680
gccaccttct taaaggtgtg attaagatag aaggttccgt caaggtatgg tatggagcca  10740
gagtaggtgt agtaagggtc gtagcctgat cccagggaag ggtttccctt tgtcttcaag  10800
cgtgtgaagg cccaaccgcg aaatgctgcc cagttgcgcg atgggatgga gatgggcacg  10860
ttggtggcgt tggcgggtat ggggtatagc atgttggcgg cggaaaggta gtcattaaag  10920
gactggtcgt tggtgtcatt tctgagcatg gcttccagcg tggaggccgt gttgtgggcc  10980
atggggaaga aggtggcgta aagacaaatg ctgtcaaact taatgctagc cccgtcaact  11040
ctaagatcgt ttcccagaga gctctgcaga accatgttaa catccttcct gaagttccat  11100
tcatatgtat atgagcctgg caggaggagg aggtttttaa tggcaaaaaa cttttggggc  11160
acctgaatgt gaaagggcac gtagcggccg tttcccaaca acatggagcg ataacggagg  11220
cccgcattgc ggtggtggtt aaagggatta acgttgtcca tgtagtccag agaccagcgc  11280
```

-continued

```
gccccaaggt taatgtagca gtctacaagc ccgggagcca ccactcgctt gttcatgtag  11340
tcgtaggtgt tggggttgtc agatatttcc acattggtgg ggttgtattt tagcttgtct  11400
ggcaggtaca gcgcaatatt ggagtaaagg aaatttctcc ataggttggc atttaggtta  11460
atttccatgg caaagttgtt acccactcct atttcattac gtgttgcaaa agtttcatct  11520
tttgtccatg tagtatctcc attatcgcct gagccattgc cattagcctt aatagcttga  11580
taggtgtcag ttaccccaat accccccaaga ggaaaacaat aatttggcaa ttcatcctca  11640
gttccatggt tttcaatgat tctaacatct ggatcatagc tgtctacagc ctgattccac  11700
atagaaaaat atctggttct atcacctatg gaatcaagca agagttgata ggacagctct  11760
gtgtttctgt cttgcaaatc taccacggca tttagctgcg atgcctgacc agcaagaaca  11820
cccatgttgc cagtgctgtt ataatacatt aggccaataa aattgtccct gaaagcaatg  11880
taattgggtc tgtttggcat agattgttga cccaacatag ctttagaatt ttcatcacct  11940
tttccaggtt tgtaagacag atgtgtgtct ggggtttcca tatttacatc ttcactgtac  12000
aaaaccactt ttggtttagt agcattgcct tgccggtcgt tcaaagaggt agtatttgag  12060
aagaattgca agtcaacctt tggaagaggc acccctttt catccggaac cagaacggat  12120
tgaccaccaa aaggatttgt aggcctggca taagatccat agcatggttt catgggagtt  12180
gtttttttaa gcactctccc tcctgccgca ttagcatcag cttcgttcca ctgagattcg  12240
ccaatttgag gttctggttg ataggaagga tctgcgtata caggtttagc ttgtgtttct  12300
gcattgtctg atcctatttg tagcccgctt tttgtaattg tttctccaga caaaggagcc  12360
tgggcataga catgtgtttt cttagtagcc tgatctcgag cgttttgctc ttcttcttcc  12420
tcttcttcat cttcatcttc ctcttcttca tcctcggcaa ctgcccggcc gctatcttcg  12480
gtttgttccc actcacagga gttaggagcg cccttgggag ctagagcgtt gtaggcagtg  12540
ccggagtagg gcttaaaagt aggccccctg tccagcacgc cgcggatgtc aaagtacgtg  12600
gaagccatat caagcacacg gttgtcaccc acagccaggg tgaaccgcgc tttgtacgag  12660
tacgcggtat cctcgcggtc cacagggatg aaccgcagcg tcaaacgctg ggaccggtct  12720
gtggttacgt cgtgcgtagg tgccaccgtg gggtttctaa acttgttatt caggctgaag  12780
tacgtctcgg tggcgcgggc aaactgcacc agcccggggc tcaggtactc cgaggcgtcc  12840
tggcccgaga tgtgcatgta agaccactgc ggcatcatcg aaggggtagc catcttggaa  12900
agcgggcgca cggcggctca gcagctcctc tggcggcgac atggacgcat acatgacaca  12960
tacgacacgt tagctattta gaagcatcgt cggcgcttca gggattgcac ccccagaccc  13020
acgatgctgt tcagtgtgct ttgccagttg ccactggcta cgggccgcat cgatcgcgga  13080
ccgctggcgg cacggcgcag ggacgcgcgg ctagggcggg ttacaacaac ggcggacggc  13140
cctggcagca caggtttctg ctgggtgtca gcggggggag gcaggtccag cgttacaggt  13200
gtgtgctggc ccagcactcc ggtagccatg ggcgcgatgg gacgggtggt gggcaggcct  13260
tgctttagtg cctcctcgta cgagggaggc tcatctattt gcgtcaccag agtttcttcc  13320
ctgtcgggcc gcggacgctt ttcgccacgc ccctctggag acactgtctc cacggccggt  13380
ggaggctcct ctacgggagg gcggggatca agcttactgt taatcttatt ttgcactgcc  13440
tggttggcca ggtccaccac cccgctaatg ccagaggcca ggccatctac caccttttgt  13500
tggaaatttt gctctttcaa cttgtccctc agcatctggc ctgtgctgct gttccaggcc  13560
ttgctgccat agttcttaat ggtggaaccg aaatttttaa tgccgctcca cagcgagccc  13620
cagctgaagg cgccaccgct catattgctg gtgccgatat cttgccagtt tcccatgaac  13680
```

-continued

```
gggcgcgagc cgtgtcgcgg ggccagagac gcaaagttga tgtcttccat tctacaaaat  13740
agttacagga ccaagcgagc gtgagactcc agactttta ttttgatttt tccacatgca  13800
acttgttttt aatcagtgtc tctgcgcctg caaggccacg gatgcaattc cgggcacggc  13860
gccaatcgcc gcggcgatca gtggaataag gaggggcagg ataccgccgc gcatgcgacg  13920
gtgcgacgcg cgccgccgcc ggtggtgcgc acgacgcatg ccgcccgtca ggccgtggcc  13980
ggccatgccc ctcctacggt gcattcttcc tcggaatccc ggcaccggga aacggaggcg  14040
gcaggtgagg gccatatctg caagaaccac aaagaccggc ttttaaacga tgctggggtg  14100
gtagcgcgct gttggcagca ccagggtcct gcctccttcg cgagccaccc tgcgcacgga  14160
aatcggggcc agcacgggct ggcgacggcg acggcggcgg cgggttccag tggtggttcg  14220
gcgtcgggta gtcgctcgtc ttctggggcg gtaggtgtag ccacgatagc cgggggtagg  14280
cgcgatggaa ggatgtaggg catattcggg cagtagtgcg ctggcggtgc cgtacttcct  14340
ggaacggcgc gggcgccggg gggctgaaac gcgaaacatc cacgggtccg tttgcacctc  14400
cgtagaggtt ttggacgcgg ccgcagcggc cgcctgcacc gcggcatctg ccaccgccga  14460
ggcaaccggg gacgtttgtg tctccatgcc ctctgtggca gtggcaatac tagtgctact  14520
ggtggtgggt atctgaacgt ccacggtctg cacgcccagt cccggtgcca cctgcttgat  14580
tggccgcacg cggacctcgg gctccagccc aggctccacg gtcatttttt ccaagacatc  14640
ttccagtcgc tggcgcttgg gtaccatcag ctgcacggtg ggtgccaagt caccagactc  14700
gcgctttagg ccgcgctttt cttcggacgg tgcaagcgtg ggcagcacct gctgcagtgt  14760
cacgggcttt aggctaggtg ttgggttgcc ctcgtccagc ggcaacgcca acatgtcctt  14820
atgccgcttt ccgtaggcaa actccccgag gcgctcgttg gcctgctcaa gcaggtcctc  14880
gtcgccgtac acctcatcat acacgcgctt gtaggtgcgg gtggagcgct caccgggcgt  14940
aaaaactacg gtggtgccgg gtcgcaaaac acgtcttacg cgtcgacctt tccactgtac  15000
ccgccgcctg ggcgcggttg cgtgcagcag ttccacctcg tcgtcaagtt catcatcatc  15060
atcatctttc tttttctttt tgacccgctt tagctttcgg ggcttgtaat cctgctcttc  15120
cttcttcggg gggccataga tctccggcgc gatgacctgg agcatctctt ctttgatttt  15180
gcgcttggac atagcttcgt tgcgcgccgc cgccgctgga tacatacaac agtacgagtc  15240
taagtagttt tttcttgcaa tctagttgcg cggggggcgg gtgcgcacgg gcacgcgcag  15300
gccgctaacc gagtcgcgca cccagtacac gttgcccctg cgaccctgag tcatagcact  15360
aatggccgcg gctgctgcgg cggccgctcg tcgcctggac ctgggggggca cagtgacaat  15420
acccgcggcc agccttcgag cggcccgcat ggccgcccgt cggccggtgc gacgtgcgcg  15480
gttaagcagg gccgccgccg cgcgttgggc ggcagtgccg ggtcggcggc ggtggcgacg  15540
tgctacgcgc ctccgccgtc tcttcatttt agcataacgc cgggctccgc gcaccacggt  15600
ctgaatggcc gcgtccactg tggacactgg tggcggcgtg ggcgtgtagt tgcgcgcctc  15660
ctccaccacc gcgtcaatgg cgtcatcgac ggtggtgcgc ccagtgcggc cgcgtttgtg  15720
cgcgccccag ggcgcgcggt agtgcccgcg cacgcgcact gggtgttggt cggagcgctt  15780
ctttgccccg ccaaacatct tgcttgggaa gcgcaggccc cagcctgtgt tattgctggg  15840
cgatataagg atggacatgt ttgctcaaaa agtgcggctc gataggacgc gcggcgagac  15900
tatgcccagg gccttgtaaa cgtaggggca ggtgcggcgt ctggcgtcag taatggtcac  15960
tcgctggact cctccgatgc tgttgcgcag cggtagcgtc ccgtgatctg tgagagcagg  16020
aacgttttca ctgacggtgg tgatggtggg ggctggcggg cgcgccaaaa tctggttctc  16080
```

-continued

```
gggaaagcga ttgaacacgt gggtcagaga ggtaaactgg cggatgagct gggagtagac  16140
ggcctggtcg ttgtagaagc tcttggagtg cacgggcaac agctcggcgc ccaccaccgg  16200
aaagttgctg atctggctcg tggagcggaa ggtcacgggg tcttgcatca tgtctggcaa  16260
cgaccagtag acctgctccg agccgcaggt tacgtcagga gtgcaaagga gggtccatga  16320
gcggatcccg gtctgagggt cgccgtagtt gtatgcaagg taccagctgc ggtactgggt  16380
gaaggtgctg tcattgctta ttaggttgta actgcgtttc ttgctgtcct ctgtcagggg  16440
tttgatcacc ggtttcttct gaggcttctc gacctcgggt tgcgcagcgg gggcggcagc  16500
ttctgccgct gcctcggcct cagcgcgctt ctcctccgcc cgtgtggcaa ggtgtcgcc  16560
gcgaatggca tgatcgttca tgtcctccac cggctgcatt gccgcggctg ccgcgttgga  16620
gttctcttcc gcgccgctgc cactgttgtt gccgccgcct gcgccatccc cgccctgttc  16680
ggtgtcatct tttaagcttg cctggtaggc gtccacatcc aacagtgcgg gaatgttacc  16740
accctccagg tcatcgtagg tgatcctaaa gccctcctgg aagggttgcc gcttgcggat  16800
gcccaacaag ttgctcaggc ggctgtgggt gaagtccacc ccgcatcctg gcagcaaaat  16860
gatgtctgga tggaaggctt cgtttgtata taccccaggc atgacaagac cagtgactgg  16920
gtcaaacccc agtctgaagt tgcgggtgtc aaactttacc ccgatgtcgc tttccagaac  16980
cccgttctgc ctgcccactt tcaagtagtg ctccacgatc gcgttgttca taaggtctat  17040
ggtcatggtc tcggagtagt tgccctcggg cagcgtgaac tccacccact catatttcag  17100
ctccacctgt ttgtccttag taagcgagcg cgacaccatc acccgcgcct taaacttatt  17160
ggtaaacatg aactcgttca catttggcat gttggtatgc aggatggttt tcaggtcgcc  17220
gccccagtgc gaacggtcgt caagattgat ggtctgtgtg cttgcctccc ccgggctgta  17280
gtcattgttt tgaatgaccg tggttagaaa gttgctgtgg tcgttctggt agttcaggga  17340
tgccacatcc gttgacttgt tgtccacaag gtacacacgg gtggtgtcga ataggggtgc  17400
caactcagag taacggatgc tgtttctccc cccggtaggc cgcaggtacc gcggaggcac  17460
aaacggcggg tccaggggag catcgaaggg ggaacccagc gccgccgcca ctggcgccgc  17520
gctcaccacg ctctcgtagg agggaggagg accttcctca tacatcgccg cgcgctgcat  17580
actaagggga atacaagaaa accaacgctc ggtgccatgg ccttggtgag ttttttattt  17640
tgcatcatgc tttttttttt ttttttttaaa acattctccc cagcctgggg cgaaggtgcg  17700
caaacgggtt gccactccct cccaaatcca ggacgctgct gtcgtctgcc gagtcatcgt  17760
cctcccacac cagaccccgc tgacggtcgt gcctttgacg acgggtgggc gggcgcgggc  17820
cggcacatc cctgtgctcc tgcgcatacg tcttccatct actcatcttg tccactaggc  17880
tctctatccc gttgttggga aatgccggag gcaggttctt ttcgcgctgc ggctgcagca  17940
gcgagttgtt taggtactcc tcctcgccca gcaggcgcgg gcgggtggtg cgagtgctgg  18000
taaaagaccc tatcaagctt ggaaatgggc tactcgcatc tgaccgcggg gccgcagcgc  18060
ctagatcgga caagctgctt ggcctgcgga agctttcctt tcgcagcgcc gcctctgcct  18120
gctcgcgctg ttgcaactct agcagggtct gcggttgcgg ggaaaacacg ctgtcgtcta  18180
tgtcgtccca gaggaatcca tcgttaccct cgggcacctc aaatcccccg gtgtagaaac  18240
cagggggcgg tagccagtgc gggttcaaga tggcattggt gaaatactcg gggttcacgg  18300
cggccgcgcg atgcaagtag tccattaggc gattgataaa cggccggttt gaggcataca  18360
tgcccggttc catgttgcgc gcggtcatgt ccagcgccac gctgggcgtt accccgtcgc  18420
gcatcaggtt aaggctcacg ctctgctgca catagcgcaa gatgcgctcc tcctcgctgt  18480
```

-continued

```
ttaaactgtg caacgagggg atcttctgcc gccggttggt cagcaggtag ttcagggttg  18540
cctccaggct gcccgtgtcc tcctgcccca gcgcgcggct gacacttgta atctcctgga  18600
aagtatgctc gtccacatgc gcctgaccta tggcctcgcg gtacagtgtc agcaagtgac  18660
ctaggtatgt gtcccgggac acgctgccac tgtccgtgaa gggcgctatt agcagcagca  18720
acaggcgcga gttgggcgtc agcaagctag acacggtcgc gcggtcgcct gtgggagccc  18780
gcaccccccca cagcccctgc aagttcttga aagcctggct caggtttacg gtctgcaggc  18840
cttgtctact ggtctggaaa aaatagtctg gcccggactg gtacacctca ctttgcggtg  18900
tctcagtcac cattagccgc agtgcgctca caaagttggt gtagtcctcc tgtccccgcg  18960
gcacgttggc gggctgtgta ctcaggaagg cgtttagtgc aaccatggag cccaggttgc  19020
cctgctgctg cgcgcgctca cgctgcgcca cggcctcgcg cacatccccc accagccggt  19080
ccaggttggt ctgcacgttg ccgctgttgt aacgagccac gcgctgaagc agcgcgtcgt  19140
agaccaggcc ggcctcatcg ggccggatgg ccctgttttc ggccagcgcg tttacgatcg  19200
ccagcacctt ctcgtgcgtg gggtttgcgc gcgccgggac caccgcttcc agaattgcgg  19260
agagccggtt ggcctgcggc tgctgccgga acgcgtcagg gttacgcgca gtcagcgaca  19320
tgatgcggtc catgacctgg cgccagtcgt ccgtggagtt aaggccggac ggctggctct  19380
gcagcgccgc ccgcaccgcc gggtccgttg cgtcttgcat catctgatca gaaacatcac  19440
cgcttagtac tcgccgtcct ctggctcgta ctcatcgtcc tcgtcatatt cctccacgcc  19500
gccgacgttg ccagcgcgcg cgggtgccac cgccagccca ggtccggccc cagctgcctc  19560
cagggcgcgt cggcttgggg cccagcgcag gtcagcgccc gcgtcaaagt aggactcggc  19620
ctctctatcg ccgctgcccg tgccagccag ggccctttgc aggctgtgca tcagctcgcg  19680
gtcgctgagc tcgcgccgcc ggctcacgct cacggccttg tggatgcgct cgttgcgata  19740
aacgcccagg tcgtcgctca aggtaagcac cttcaacgcc atgcgcatgt agaacccctc  19800
gatctttacc tccttgtcta tgggaacgta aggggtatgg tatatcttgc gggcgtaaaa  19860
cttgcccaga ctgagcatgg aatagttaat ggcggccacc ttgtcagcca ggctcaagct  19920
gcgctcctgc accactatgc tctgcagaat gtttatcaaa tcgagcagcc agcggccctc  19980
gggctctact atgtttagca gcgcatccct gaatgcctcg ttgtccctgc tgtgctgcac  20040
tataaggaac agctgcgcca tgagcggctt gctatttggg ttttgctcca gcgcgcttac  20100
aaagtcccac agatgcatca gtcctatagc cacctcctcg cgcgccacaa gcgtgcgcac  20160
gtggttgtta aagctttttt gaaagttaat ctcctggttc accgtctgct cgtacgcggt  20220
taccaggtcg gcggccgcca cgtgtgcgcg cgcgggacta atcccggtcc gcgcgtcggg  20280
ctcaaagtcc tcctcgcgca gcaaccgctc gcggttcagg ccatgccgca actcgcgccc  20340
tgcgtggaac tttcgatccc gcatctcctc gggctcctct ccctcgcggt cgcgaaacag  20400
gttctgccgc ggcacgtacg cctcgcgcgt gtcacgcttc agctgcaccc ttgggtgtcg  20460
ctcaggagag ggcgctccta gccgcgccag gccctcgccc tcctccaagt ccaggtagtg  20520
ccgggcccgg cgccgcgggg gttcgtaatc accatctgcc gccgcgtcag ccgcggatgt  20580
tgcccctcct gacgcggtag gagaagggga gggtgccctg catgtctgcc gctgctcttg  20640
ctcttgccgc tgctgaggag gggggcgcat ctgccgcagc accggatgca tctgggaaaa  20700
gcaaaaaagg ggctcgtccc tgtttccgga ggaatttgca agcggggtct tgcatgacgg  20760
ggaggcaaac cccgttcgc cgcagtccgg ccggcccgag actcgaaccg gggtcctgc  20820
gactcaaccc ttggaaaata accctccggc tacagggagc gagccactta atgctttcgc  20880
```

-continued

```
tttccagcct aaccgcttac gccgcgcgcg gccagtggcc aaaaaagcta gcgcagcagc  20940
cgccgcgcct ggaaggaagc caaaaggagc gctcccccgt tgtctgacgt cgcacacctg  21000
ggttcgacac gcgggcggta accgcatgga tcacggcgga cggccggatc cggggttcga  21060
accccggtcg tccgccatga taccccttgcg aatttatcca ccagaccacg gaagagtgcc  21120
cgcttacagg ctctcctttt gcacggtcta gagcgtcaac gactgcgcac gcctcaccgg  21180
ccagagcgtc ccgaccatgg agcacttttt gccgctgcgc aacatctgga accgcgtccg  21240
cgactttccg cgcgcctcca ccaccgccgc cggcatcacc tggatgtcca ggtacatcta  21300
cggatatcat cgccttatgt tggaagacct cgcccccgga gccccggcca ccctacgctg  21360
gcccctctac cgccagccgc cgccgcactt tttggtggga tatcagtacc tggtgcggac  21420
ttgcaacgac tacgtctttg actcaagggc ttactcgcgt ctcaggtaca ccgagctctc  21480
gcagccgggt caccagaccg ttaactggtc cgttatggcc aactgcactt acaccatcaa  21540
cacgggcgca taccaccgct ttgtggacat ggatgacttc cagtctaccc tcacgcaggt  21600
gcagcaggcc atattagccg agcgcgttgt cgccgacctg gccctgcttc agccgatgag  21660
gggcttcggg gtcacacgca tgggaggaag agggcgccac ctacggccaa actccgccgc  21720
cgccgtagcg atagatgcaa gagatgcagg acaagaggaa ggagaagaag aagtgccggt  21780
agaaaggctc atgcaagact actacaaaga cctgcgccga tgtcaaaacg aagcctgggg  21840
catggccgac cgcctgcgca ttcagcaggc cggacccaag gacatggtgc ttctgtcgac  21900
catccgccgt ctcaagaccg cctactttaa ttacatcatc agcagcacct ccgccagaaa  21960
caaccccgac cgccacccgc tgccgcccgc cacggtgctc agcctacctt gcgactgtga  22020
ctggttagac gcctttctcg agaggttttc cgatccggtc gatgcggact cgctcaggtc  22080
cctcggtggc ggagtaccta cacaacaatt gttgagatgc atcgttagcg ccgtatccct  22140
gccgcacggc agccccccgc caacccataa ccgggacatg acgggcggcg tcttccaact  22200
gcgcccccgc gagaacggcc gcgccgtcac cgagaccatg cgccgtcgcc gcggggagat  22260
gatcgagcgc tttgtcgacc gcctcccggt gcgccgtcgt cgccgccgtg tccccccctcc  22320
cccaccgccg ccagaagaag aagaagaagg ggaggccctt atggaagagg agattgaaga  22380
agaagaggcc cctgtagcct ttgagcgcga ggtgcgcgac actgtcgccg agctcatccg  22440
tcttctggag gaggagttaa ccgtgtcggc gcgcaactcc cagtttttca acttcgccgt  22500
ggacttctac gaggccatgg agcgccttga ggccttgggg gatatcaacg aatccacgtt  22560
gcgacgctgg gttatgtact tcttcgtggc agaacacacc gccaccaccc tcaactacct  22620
ctttcagcgc ctgcgaaact acgccgtctt cgcccggcac gtggagctca atctcgcgca  22680
ggtggtcatg cgcgcccgcg atgccgaagg gggcgtggtc tacagccgcg tctggaacga  22740
gggaggcctc aacgccttct cgcagctcat ggcccgcatc tccaacgacc tcgccgccac  22800
cgtggagcga gccggacgcg gagatctcca ggaggaagag atcgagcagt tcatggccga  22860
aatcgcctat caagacaact caggagacgt gcaggagatt ttgcgccagg ccgccgtcaa  22920
cgacaccgaa attgattctg tcgaactctc tttcaggttc aagctcaccg ggcccgtcgt  22980
cttcacgcag aggcgccaga ttcaggagat caaccgccgc gtcgtcgcgt tcgccagcaa  23040
cctccgcgcg cagcaccagc tcctgcccgc gcgcggcgcc gacgtgcccc tgccccctct  23100
cccggcgggt cccgagcccc ccctacctcc gggggcccgc ccgcgtcacc gcttttagat  23160
gcatcatcca aggacacccc cgcggcccac cgcccgccgc gcggtaccgt agtcgcgccg  23220
cggggatgcg gcctcttgca agtcatcgac gccgccacca accagcccct ggaaatcagg  23280
```

-continued

```
tatcacctgg acctagcccg cgccctgacc cggctatgcg aggtaaacct gcaggagctc  23340

ccgcctgacc tgtcgccgcg ggagctccag accatggaca gctcccatct gcgcgatgtt  23400

gtcatcaagc tccgaccgcc gcgcgcggac atctggactt tgggctcgcg cggcgtggtg  23460

gtccgatcca ccataactcc cctcgagcag ccagacggtc aaggacaagc agccgaagta  23520

gaagaccacc agccaaaccc gccaggcgag ggctcaaat tcccactctg cttccttgtg  23580

cgcggtcgtc aggtcaacct cgtgcaggat gtacagcccg tgcaccgctg ccagtactgc  23640

gcacgttttt acaaaagcca gcacgagtgt tcggcccgtc gcagggactt ctactttcac  23700

cacatcaaca gccactcctc caactggtgg cgggagatcc agttcttccc gatcggctcg  23760

catcctcgca ccgagcgtct ctttgtcacc tacgatgtag agacctatac ttggatgggg  23820

gcctttggga agcagctcgt gcccttcatg ctggttatga agttcggcgg agatgagcct  23880

ctggtgaccg ccgcgcgaga cctagccgtg gaccttggat gggaccgctg ggaacaagac  23940

ccgcttacct tctactgcat caccccagaa aaaatggcca taggtcgcca gtttaggacc  24000

tttcgcgacc acctgcaaat gctaatggcc cgtgacctgt ggagctcatt cgtcgcttcc  24060

aaccctcatc ttgcagactg ggccctgtca gaacacgggc tcagctcccc tgaggagctc  24120

acctacgagg aacttaaaaa attgccctcc atcaagggca ccccgcgctt cttggaactt  24180

tacatcgtgg gccacaacat caacggcttc gacgagatcg tgctcgccgc ccaggtaatt  24240

aacaaccgtt ccgaggtgcc gggacccttc cgcatcacac gcaactttat gcctcgcgcg  24300

ggaaagatac ttttcaacga tgtcaccttc gccctgccaa acccgcgttc caaaaagcgc  24360

acggactttt tgctctggga gcagggcgga tgcgacgaca ctgacttcaa ataccagtac  24420

ctcaaagtca tggttaggga cacctttgcg ctcacccaca cctcgctccg gaaggccgcg  24480

caggcatacg cgctacccgt agaaaaggga tgctgcgcct accaggccgt caaccagttc  24540

tacatgctag gctcttaccg ttcggaggcc gacgggtttc cgatccaaga gtactggaaa  24600

gaccgcgaag agtttgtcct caaccgcgag ctgtggaaaa aaaagggaca ggataagtat  24660

gacatcatca aggaaaccct ggactactgc gccctagacg tgcaggtcac cgccgagctg  24720

gtcaacaagc tgcgcgactc ctacgcctcc ttcgtgcgtg acgcggtagg tctcacagac  24780

gccagcttca acgtcttcca gcgtccaacc atatcatcca actcacatgc catcttcagg  24840

cagatagtct tccgagcaga gcagcccgcc cgtagcaacc tcggtcccga cctcctcgct  24900

ccctcgcacg aactatacga ttacgtgcgc gccagcatcc gcggtggaag atgctaccct  24960

acatatcttg gaatactcag agagcccctc tacgtttacg acatttgcgg catgtacgcc  25020

tccgcgctca cccaccccat gccatggggt cccccactca acccatacga gcgcgcgctt  25080

gccgcccgcg catggcagca ggcgctagac ttgcaaggat gcaagataga ctacttcgac  25140

gcgcgcctgc tgcccggggt ctttaccgtg gacgcagacc ccccggacga gacgcagcta  25200

gacccactac cgccattctg ttcgcgcaag ggcggccgcc tctgctggac caacgagcgc  25260

ctacgcggag aggtagccac cagcgttgac cttgtcaccc tgcacaaccg cggttggcgc  25320

gtgcacctgg tgcccgacga gcgcaccacc gtctttcccg aatggcggtg cgttgcgcgc  25380

gaatacgtgc agctaaacat cgcggccaag gagcgcgccg atcgcgacaa aaaccaaacc  25440

ctgcgctcca tcgccaagtt gctgtccaac gccctctacg ggtcgtttgc caccaagctt  25500

gacaacaaaa agattgtctt ttctgaccag atggacgcgg ccaccctcaa aggcatcacc  25560

gcgggccagg tgaatatcaa atcctcctcg tttttggaaa ctgacaatct tagcgcagaa  25620

gtcatgcccg cttttgagag ggagtactca ccccaacagc tggccctcgc agacagcgat  25680
```

-continued

```
gcggaagaga gtgaggacga acgcgccccc accccctttt atagcccccc ttcaggaaca  25740
cccggtcacg tggcctacac ctataaacca atcaccttcc ttgatgccga agagggcgac  25800
atgtgtcttc acaccctgga gcgagtggac cccctagtgg acaacgaccg ctacccctcc  25860
cacttagcct ccttcgtgct ggcctggacg cgagccttcg tctcagagtg gtccgagttt  25920
ctatacgagg aggaccgcgg aacaccgctc gaggacaggc ctctcaagtc tgtatacggg  25980
gacacggaca gccttttcgt caccgagcgt ggacaccggc tcatggaaac cagaggtaag  26040
aaacgcatca aaaagcatgg gggaaacctg gtttttgacc ccgaacggcc agagctcacc  26100
tggctcgtgg aatgcgagac cgtctgcggg gcctgcggcg cggatgccta ctccccggaa  26160
tcggtatttc tcgcgcccaa gctctacgcc cttaaaagtc tgcactgccc ctcgtgcggc  26220
gcctcctcca agggcaagct gcgcgccaag ggccacgccg cggaggggct ggactatgac  26280
accatggtca aatgctacct ggccgacgcg cagggcgaag accggcagcg cttcagcacc  26340
agcaggacca gcctcaagcg caccctggcc agcgcgcagc ccggagcgca ccccttcacc  26400
gtgacccaga ctacgctgac gaggaccctg cgcccgtgga aagacatgac cctggcccgt  26460
ctggacgagc accgactact gccgtacagc gaaagccgcc ccaacccgcg aaacgaggag  26520
atatgctgga tcgagatgcc gtagagcacg tgaccgagct gtgggaccgc ctggaactgc  26580
ttggtcaaac gctcaaaagc atgcctacgg cggacggcct caaaccgttg aaaaactttg  26640
cttccttgca agaactgcta tcgctgggcg gcgagcgcct tctggcgcat ttggtcaggg  26700
aaaacatgca agtcagggac atgcttaacg aagtggcccc cctgctcagg gatgacggca  26760
gctgcagctc tcttaactac cagttgcagc cggtaatagg tgtgatttac gggcccaccg  26820
gctgcggtaa gtcgcagctg ctcaggaacc tgctttcttc ccagctgatc tcccctaccc  26880
cggaaacggt tttcttcatc gccccgcagg tagacatgat ccccccatct gaactcaaag  26940
cgtgggaaat gcaaatctgt gagggtaact acgcccctgg gccggatgga accattatac  27000
cgcagtctgg caccctccgc ccgcgctttg taaaaatggc ctatgacgat ctcatcctgg  27060
aacacaacta tgacgttagt gatcccagaa atatcttcgc ccaggccgcc gcccgtgggc  27120
ccattgccat cattatggac gaatgcatgg aaaatctcgg aggtcacaag ggcgtctcca  27180
agttcttcca cgcatttcct tctaagctac atgacaaatt tcccaagtgc accggataca  27240
ctgtgctggt ggttctgcac aacatgaatc cccggaggga tatggctggg aacatagcca  27300
acctaaaaat acagtccaag atgcatctca tatccccacg tatgcaccca tcccagctta  27360
accgctttgt aaacacttac accaagggcc tgcccctggc aatcagcttg ctactgaaag  27420
acatttttag gcaccacgcc cagcgctcct gctacgactg gatcatctac aacaccaccc  27480
cgcagcatga agctctgcag tggtgctacc tccaccccag agacgggctt atgcccatgt  27540
atctgaacat ccagagtcac ctttaccacg tcctggaaaa aatacacagg accctcaacg  27600
accgagaccg ctggtcccgg gcctaccgcg cgcgcaaaac ccctaaataa agacagcaag  27660
acacttgctt gatcaaaatc caaacagagt ctggttttta tttatgtttt aaaccgcatt  27720
gggaggggag gaagccttca gggcagaaac ctgctggcgc agatccaaca gctgctgaga  27780
aacgacatta agttcccggg tcaaagaatc caattgtgcc aaaagagccg tcaacttgtc  27840
atcgcgggcg gatgaacggg aagctgcact gcttgcaagc gggctcagga aagcaaagtc  27900
agtcacaatc ccgcgggcgg tggctgcagc ggctgaagcg gcggcggagg ctgcagtctc  27960
caacggcgtt ccagacacgg tctcgtaggt caaggtagta gagtttgcgg gcaggacggg  28020
gcgaccatca atgctggagc ccatcacatt ctgacgcacc ccggcccatg gggcatgcg   28080
```

-continued

```
cgttgtcaaa tatgagctca caatgcttcc atcaaacgag ttggcgctca tggcggcggc  28140
tgctgcaaaa cagatacaaa actacatgag acccccacct tatatattct ttcccaccct  28200
taagccccgc ccatcgatgg caaacagcta ttatgggtat tatgggtgct agcgacatga  28260
ggttgccccg tattcagtgt cgctgatttg tattgtctga agttgttttt acgttaagtt  28320
gatgcagatc aattaatacg atacctgcgt cataattgat tatttgacgt ggtttgatgg  28380
cctccacgca cgttgtgata tgtagatgat aatcattatc actttacggg tcctttccgg  28440
tgatccgaca ggttacgggg cggcgacctc gcgggttttc gctatttatg aaaattttcc  28500
ggtttaaggc gtttccgttc ttcttcgtca taacttaatg tttttattta aaataccctc  28560
tgaaaagaaa ggaaacgaca ggtgctgaaa gcgaggcttt ttggcctctg tcgtttcctt  28620
tctctgtttt tgtccgtgga atgaacaatg gaagttaacg gatccaggcc gcgagcaaaa  28680
ggccagcaaa aggccaggaa ccgtaaaaag gccgcgttgc tggcgttttt ccataggctc  28740
cgcccccctg acgagcatca caaaaatcaa cgctcaagtc agaggtggcg aaacccgaca  28800
ggactataaa gataccaggc gtttccccct ggaagctccc tcgtgcgctc tcctgttccg  28860
accctgccgc ttaccggata cctgtccgcc tttctccctt cgggaagcgt ggcgctttct  28920
catagctcac gctgtaggta tctcagttcg gtgtaggtcg ttcgctccaa gctgggctgt  28980
gtgcacgaac cccccgttca gcccgaccgc tgcgccttat ccggtaacta tcgtcttgag  29040
tccaacccgg taagacacga cttatcgcca ctggcagcag ccactggtaa caggattagc  29100
agagcgaggt atgtaggcgg tgctacagag ttcttgaagt ggtggcctaa ctacggctac  29160
actagaagaa cagtatttgg tatctgcgct ctgccaaagc cagttacctt cggaaaaaga  29220
gttggtagct cttgatccgg caaacaaacc accgctggta gcggtggttt ttttgtttgc  29280
aagcagcaga ttacgcgcag aaaaaaagga tctcaagaag atcctttgat cttttctacg  29340
gggtctgacg ctcagtggaa cgaaaactca cgttaaggga ttttggtcat cagattatca  29400
aaaaggatct tcacctagat ccttttaaat taaaaatgaa gttttaaatc aatctaaagt  29460
atatatgagt aaacttggtc tgacagttac caatgcttaa tcagtgaggc acctatctca  29520
gcgatctgtc tatttcgttc atccatagtt gcctgactcc ccgtagtgta gataactacg  29580
atacgggagg gcttaccatc cggccccagt gctgcaatga taccgcgtga cccacgctca  29640
ccggctcctg atttatcagc aataaaccag ccagccggaa gtgccgagcg cagaagtggt  29700
cctgcaactt tatccgcctc catccagtct attagttgtt gccgggaagc tagagtaagt  29760
agttcgccag ttaatagttt tcgcaacgtt gttgccattg ctacaggcat cgtggtgtca  29820
cgctcgtcgt ttggtatggc ttcattcagc tccggttccc aacgatcaag gcgagttaca  29880
tgatccccca tgttgtgcaa aaaagcggtt agctccttcg gtcctccgat agttgtcaga  29940
agtaagttgg ccgcagtgtt atcactcatg gttatggcag cactgcataa ttctcttact  30000
gtcatgccat ccgtaagatg cttttctgtg actggtgagt attcaaccaa gaatacggga  30060
taataccgcg ccacatagca gaactttaaa agtgctcatc attgggaaac gttcttcggg  30120
gcgaaaactc tcaaggatct taccgctgtt gagatccagt tcgatgtaac ccactcgcgc  30180
acccaagtga tcttctgcat cttttacttt caccagcgtt tctgggtgag caaaaacagg  30240
aaggcaaaat gccgcaaaaa agggaataag ggcgacacgg aaatgttgaa tactcatact  30300
tttccttttt caatattatt gaagcattta tcagggttat tgtctcatca gcggatacat  30360
atttg                                                              30365
```

-continued

```
<210> SEQ ID NO 5
<211> LENGTH: 33
<212> TYPE: DNA
<213> ORGANISM: Homo sapiens

<400> SEQUENCE: 5

gcggaattcg gcttggtgac ttagagaaca gag                               33


<210> SEQ ID NO 6
<211> LENGTH: 33
<212> TYPE: DNA
<213> ORGANISM: Homo sapiens

<400> SEQUENCE: 6

gcgggatcct tgaacccgga ccctctcaca cta                               33


<210> SEQ ID NO 7
<211> LENGTH: 20
<212> TYPE: DNA
<213> ORGANISM: Artificial Sequence
<220> FEATURE:
<223> OTHER INFORMATION: derived from Adenovirus

<400> SEQUENCE: 7

actctcttcc gcatcgctgt                                              20


<210> SEQ ID NO 8
<211> LENGTH: 21
<212> TYPE: DNA
<213> ORGANISM: Artificial Sequence
<220> FEATURE:
<223> OTHER INFORMATION: derived from Adenovirus

<400> SEQUENCE: 8

cttgcgactg tgactggtta g                                            21


<210> SEQ ID NO 9
<211> LENGTH: 20
<212> TYPE: DNA
<213> ORGANISM: Artificial Sequence
<220> FEATURE:
<223> OTHER INFORMATION: derived from Adenovirus

<400> SEQUENCE: 9

ccgcacccac tatcttcata                                              20


<210> SEQ ID NO 10
<211> LENGTH: 20
<212> TYPE: DNA
<213> ORGANISM: Artificial Sequence
<220> FEATURE:
<223> OTHER INFORMATION: derived from Adenovirus

<400> SEQUENCE: 10

ggtgtccaaa ggttcggaga                                              20
```

SELF-REARRANGING DNA VECTORS

CROSS REFERENCE TO RELATED APPLICATIONS

This application is a continuation of International Application No. PCT/US01/27682, filed Sep. 7, 2001, which claims benefit of U.S. provisional application Nos. 60/246,904, and 60/231,053, filed Nov. 8, 2000, and Sep. 8, 2000, respectively, all of which are hereby incorporated by reference in their entirety.

BACKGROUND OF THE INVENTION

The invention relates to DNA vectors.

Mammalian cell expression vectors based on DNA viruses have been widely discussed as gene delivery vehicles for genetic therapy. Among the different DNA viruses proposed for this purpose have been adenoviruses, baculovirus, Epstein Barr virus, and herpes simplex virus. In addition other smaller viruses that have an intranuclear phase in which the viral genome is present as a double stranded DNA, such as retroviruses and parvoviruses, have been proposed as gene delivery vehicles.

Adenoviral vectors (AdV), for example, have a recognized potential for gene delivery, founded in their broad host range, robust growth in culture, and capacity to infect mitotically quiescent cells (Graham and Prevec, Manipulation of adenovirus vectors, p. 109–128, In E. J. Murray (ed.), Methods in Molecular Biology, vol. 7, Humana, Clifton, N.J., 1991; Trapnell and Gorziglia, Curr. Opin. Biotechnol. 5:617–625, 1994). AdV can be propagated in a helper cell line, 293, a human embryonic kidney cell line transformed by adenovirus type 5 (Graham et al., J. Gen. Virol. 36:59–72, 1994). 293 cells express the viral E1 gene products (E1a and E1b) that are the master regulatory proteins for subsequent viral gene expression. E1 deleted viruses can propagate in 293 cells, but not in other cells. Although it would be expected that E1 deleted viruses lack the machinery to express viral genes, several studies have demonstrated that cellular E1-like components can stimulate viral gene expression (Imperiale et al., Mol. Cell. Biol. 4:867–74, 1984; Onclercq et al., J. Virol. 62:4533–7,1988; Spergel et al., J. Virol. 66:1021–30, 1992). The expression of these viral genes results in the relatively rapid elimination of transduced cells in vivo as a result of cytotoxic T cell responses (Yang et al., Immunity 1:433–42, 1994; Yang et al., Gene Ther. 3:137–44, 1996; Yang et al., J. Virol. 69:2004–15, 1995).

Thus attention has been focused on eliminating the remaining vestiges of viral expression. Viral genes that have been deleted for this purpose include the gene for E4 proteins (Armentano et al., Hum. Gene Ther. 6:1343–53, 1995; Kochanek et al., Proc. Natl. Acad. Sci. USA 93:5731–6, 1996; and Yeh et al., J. Virol. 70:559–565, 1996), DNA binding protein (Engelhardt et al., Proc. Natl. Acad. Sci. USA 21:6196–6200, 1994; and Gorziglia et al., J. Virol. 70:4173–8, 1996), DNA polymerase (Amalfitano et al., J. Virol. 72:926–33, 1998), and the preterminal protein (Schaack et al., Proc. Natl. Acad. Sci. USA 93:14686–91, 1996). The most aggressive approach has been the creation of helper virus-dependent vectors that lack all viral genes (Hardy et al., J. Virol. 71:1842–9, 1997; Kochaneketal., Proc. Natl. Acad. Sci. USA 93:5731–6, 1996; Lieber et al., J. Virol. 70:8944–60, 1996; Mitani et al., Proc. Natl. Acad. Sci. USA 92:3854–8, 1995; and Parks et al., Proc. Natl. Acad. Sci. USA 93:13565–13570, 1996). These vectors have high capacity, evoke reduced cellular immune responses and show prolonged expression in vivo (Morsy et al., Proc. Natl. Acad. Sci. USA 95:7866–71, 1998). However to deploy these viruses on the scale required for human clinical application presents major challenges because a cesium chloride (CsCl) gradient is needed to remove the helper virus.

SUMMARY OF THE INVENTION

In one aspect, the invention features a replicatable viral DNA vector encoding a site-specific DNA-altering enzyme and a DNA target recognized by the enzyme, the enzyme selectively converting, in a cell expressing the enzyme, the DNA vector to a rearranged form.

In preferred embodiments, the rearranged form includes an autonomously replicating episome and a linear DNA product. In other preferred embodiments, the vector comprises adenoviral DNA.

In yet other preferred embodiments, the vector includes a genetically-engineered recombination site (such as a target of Cre or FLP). Preferably, such a recombination site includes a recognition sequence of a site-specific DNA altering enzyme.

In another preferred embodiment, the site-specific DNA altering enzyme is a recombinase (such as Cre or FLP) or an integrase. Preferably, such an enzyme is functional in a mammalian cell. Preferred embodiments of the vector also include an origin of replication that functions in a mammalian cell (such as an Epstein Barr Virus replicon). Moreover, the vector typically includes a gene of interest (such as a therapeutic gene that encodes a protein or polypeptide or an RNA product).

In another aspect, the invention features a method for assembling a recombinant adenoviral DNA. The method, in general, includes the steps of: (a) providing a first linearized DNA vector comprising a restriction site and a cos site and a second linearized DNA vector comprising the restriction site, an adenoviral nucleic acid molecule, and a cos site; and (b) ligating the first and second linearized DNA vectors, the ligation assembling a recombinant adenoviral DNA.

In preferred embodiments, the first linearized DNA vector comprises a selectable marker (such as a gene encoding a polypeptide that confers, on a host cell expressing such a polypeptide, resistance to an antibiotic). In other preferred embodiments, the first linearized DNA vector includes an adenoviral left-end inverted terminal repeat, a gene of interest, or both. In still other preferred embodiments, the second linearized DNA vector includes a selectable marker. Preferably, the second linearized DNA vector includes an adenoviral right-end inverted terminal repeat.

The method further includes packaging the assembled adenoviral DNA into a phage and infecting a host cell. Typically the first and second linearized DNAs include cosmid vector DNA. In addition, such adenoviral DNA is typically flanked by cleavage sites (such as intron endonuclease cleavage sites).

In another aspect, the invention features an adenovirus producer cell having a nucleic acid molecule that expresses a dominant negative site-specific DNA-altering enzyme. In preferred embodiments, the site-specific DNA altering enzyme is a dominant negative recombinase (for example, a Cre recombinase such as CreY324C or a Flp recombinase). Exemplary adenovirus producer cells include, without limitation, 293 human embryonic kidney cells, per.C6 cells, and N52 cells.

In yet another aspect, the invention features a vector comprising, in the 5' to 3' direction, a first genetically engineered cis-acting target recognized by a site-specific DNA altering enzyme; a gene of interest; a lineage-specific gene promoter; a second genetically engineered cis-acting target recognized by a site-specific DNA altering enzyme; and a nucleic acid molecule encoding a site-specific DNA altering enzyme.

In still another aspect, the invention features a vector including, in the 5' to 3' direction, a first genetically engineered cis-acting target recognized by a site-specific DNA altering enzyme; a gene of interest; a bi-directional promoter, comprising a second genetically engineered cis-acting target recognized by a site-specific DNA altering enzyme; and a nucleic acid molecule encoding a site-specific DNA altering enzyme.

In related aspects, the invention features a method of gene therapy including the administration to a patient in need of gene therapy a therapeutically effective amount of the vector of the invention, which is expressed in the patient. The invention further relates to a population of cells transfected with the vector of the invention.

Accordingly, the invention further relates to the use of a recombinant viral vector or use of a recombinant viral particle for gene therapy. Such vectors and viral particles may be introduced either in vitro into a host cell removed from the patient, or directly in vivo, into the body to be treated, according to standard methods known in the art.

The invention also relates to a pharmaceutical composition that includes a therapeutically effective amount of a recombinant viral vector or viral particle prepared according to the methods disclosed herein, in combination with a vehicle that is acceptable from a pharmaceutical standpoint. Such a pharmaceutical composition may be prepared according to the techniques commonly employed and administered by any known administration route, for example systemically (in particular, by intravenous, intratracheal, intraperitoneal, intramuscular, subcutaneous, intratumoral, or intracranial routes) or by aerosolization or intrapulmonary administration.

One skilled in the art will appreciate that suitable methods of administering a vector (particularly an adenoviral vector) of the present invention to an animal for purposes of gene therapy, chemotherapy, and vaccination are available, and, although more than one route can be used for administration, one particular route may provide a more immediate and more effective reaction than another. Pharmaceutically acceptable excipients also are well known to those who are skilled in the art, and are readily available. The choice of excipient will be determined, in part, by the particular method used to administer the recombinant vector or particle. Accordingly, there are a wide variety of suitable formulations for use in the context of the present invention.

By "recombinant DNA vector" is meant a DNA sequence containing a desired sequence (such as a gene of interest) and an appropriate regulatory element(s) necessary for the expression of the operably linked sequence in a particular host organism (such as a mammal).

By "operably linked" is meant that a gene and a regulatory element(s) are connected to permit gene expression when the appropriate molecules (for example, transcriptional activator proteins) are bound to the regulatory sequence(s).

By "regulatory element" is meant a genetic element that controls some aspect of the expression of a nucleic acid sequence. For example, a promoter is a regulatory element that facilitates the initiation of transcription of an operably linked coding region. Other genetic regulatory elements include, without limitation, splicing signals, polyadenylation signals, and termination signals. For example, transcriptional regulatory elements in eukaryotes include promoter and enhancer elements. Promoters and enhancers include arrays of DNA sequences that interact directly or indirectly with cellular proteins involved in transcription. Promoter and enhancer elements have been isolated from a variety of eukaryotic sources including genes in mammalian cells and viruses.

By "transfection" is meant the introduction of foreign DNA into eukaryotic cells. Transfection is typically accomplished by a variety of means known in the art including, without limitation, calcium phosphate-DNA co-precipitation, DEAE-dextran-mediated transfection, electroporation, microinjection, liposome fusion, lipofection, protoplast fusion, and biolistics.

By "stably transfected" is meant the introduction of foreign DNA into the genome of the transfected cell. In general, transfer and expression of transgenes in mammalian cells are now routine practices to those skilled in the art, and have become major tools to carry out gene expression studies and to generate vectors useful in gene therapy.

By "gene of interest" is meant a gene inserted into a vector whose expression is desired in a host cell. Genes of interest include, without limitation, genes having therapeutic value, as well as reporter genes. A variety of such genes are useful in the invention, including genes of interest encoding a protein, which provides a therapeutic function. In addition, the gene of interest, if a therapeutic gene, can render its effect at the level of RNA, for instance, by encoding an antisense message or ribozyme, a protein which affects splicing or 3' processing (e.g., polyadenylation), or it can encode a protein which acts by affecting the level of expression of another gene within the cell (i.e., where gene expression is broadly considered to include all steps from initiation of transcription through production of a processed protein), for example, by mediating an altered rate of mRNA accumulation, an alteration of mRNA transport, and/or a change in post-transcriptional regulation.

By "reporter gene" is meant a gene sequence that encodes a reporter molecule (including an enzyme). A "reporter molecule" is detectable in any detection system, including, but not limited to, enzyme (e.g., ELISA, as well as enzyme-based histochemical assays), fluorescent, radioactive, and luminescent systems. Exemplary reporter gene systems include the *E. coli* beta-galactosidase or glucuronidase genes, green fluorescent protein (GFP), blue fluorescent protein (BFP), the human placental alkaline phosphatase gene, and the chloramphenicol acetyltransferase (CAT) gene; other reporter genes are known in the art and may be employed as desired.

By "transgene" is meant any piece of DNA that is inserted by artifice into a cell, and becomes part of the genome of the organism that develops from that cell. Such a transgene may include a gene that is partly or entirely heterologous (i.e., foreign) to the transgenic organism, or may represent a gene homologous to an endogenous gene of the organism.

By "transgenic" is meant any cell that includes a DNA sequence that is inserted by artifice into a cell, and becomes part of the genome of the organism that develops from that cell.

By "polypeptide" is meant any chain of amino acids, regardless of length or post-translational modification (for example, glycosylation or phosphorylation).

By "derived from" is meant isolated from or having the sequence of a naturally occurring sequence (e.g., a cDNA, genomic DNA, synthetic, or combination thereof).

By “nucleic acid” is meant a polynucleotide (DNA or RNA).

By “gene” is meant any nucleic acid sequence coding for a protein or an RNA molecule.

By “gene product” is meant either an untranslated RNA molecule transcribed from a given gene or coding sequence (such as mRNA or antisense RNA) or the polypeptide chain translated from the mRNA molecule transcribed from the given gene or coding sequence. Nucleic acids according to the invention can be wholly or partially synthetically made, can comprise genomic or complementary DNA (cDNA) sequences, or can be provided in the form of either DNA or RNA.

The presently claimed invention affords a number of advantages. For example, applicants’ gene therapy vehicles, particularly those based on recombinant adenoviruses, minimize the propensity of the vectors to activate host immune surveillance, and thereby maximize the persistence for the DNA transduced. The invention therefore facilitates the development of gene delivery vectors designed to enhance persistence of virally delivered genes and evade the cellular immune response by severing the connection between the sole adenoviral enhancer and the sequences encoding potentially antigenic viral proteins.

As described in more detail below, the mechanism by which this is accomplished differs significantly from any other previous approaches. For example, to reduce the immunogenicity of vectors it is widely acknowledged that some intervention, such as the removal of key genes, or the prevention of their expression in the cells targeted for therapy, is important; however, many related approaches are directed at the host and have generally focused on the selective induction of tolerance to adenoviral antigens, or similar strategies directed at inducing a temporally restricted or antigen-specific compromise of the immune system.

In addition, the poor persistence of transduced DNA appears to be due in part to immunological rejection of transduced cells and to the inability of the viral DNA to replicate, a feature generally inherent in the design of adenoviral vectors, but one which is not associated with applicants’ claimed gene therapy vehicles.

Moreover, some contemporary adenoviral vectors are designed to propagate in specific host cells which provide essential replication factors in trans. These vectors are typically based on cell lines which express the master regulatory proteins of the E1 complex, which are required for induction of adenoviral DNA replication. In cells expressing E1 genes, the best studied of which is a human embryonic kidney cell line transformed by DNA from human adenovirus 5 (called HEK293, or simply 293), viruses lacking E1 genes propagate well. Such viruses do not propagate on cell lines which do not express E1, and do not generally propagate well in the target cells to which the therapeutic gene is to be delivered. Cells transduced with E1-deleted adenovirus vectors also do not express high levels of viral genes in the absence of E1. However, the weak residual expression that remains in such vectors appears to be sufficient to induce cellular immune responses that contribute to the destruction of the transduced cells.

In addition, the gene therapy vectors claimed herein are hybrid vectors capable of self-rearrangement to form circular and linear DNA products. The linear DNA has a compromised ability to express adenoviral genes, and therefore has a lower immunological profile. And the circular DNA behaves like a mammalian plasmid, encoding the gene of interest and persisting by autonomous replication in the nucleus.

For example, the circularization of an adenoviral vector via the action of Cre recombinase beneficially places a gene of interest (for example, a therapeutic gene) on a self-replicating episome. Vector circularization occurs in a tissue-targeted manner, for example, as a result of the activation of a synthetic liver-specific promoter upstream of the recombinase Cre. Once circularized, the EBV replicon in the episome confers improved persistence on the therapeutic gene as detected by reporter gene expression and direct assay for the presence of vector DNA sequences.

Furthermore, the invention eliminates the requirement for a helper virus, thus avoiding two potential limitations of that system. First, the continuous expression of Cre recombinase may lead to toxicity in host cells, either as a direct consequence of the protein’s activity or via its immunogenicity. Second, the Cre helper virus may itself produce antigenic viral proteins that contribute to the immunologic elimination of infected host cells. In contrast, the self-resolving adenovirus/EBV vector system disclosed herein advantageously provides no alternative source of viral proteins, and Cre expression is terminated upon rearrangement.

In addition, the invention described herein provides tools for analyzing the roles of the enhancer in viral gene regulation and virus growth.

The invention also provides a convenient general system for creating recombinant adenoviruses, which increase their attractiveness as gene transduction tools for basic research. The system, for example, employs two conventional plasmid vectors and a λ phage packaging step. The entire recombinant AdV genome is assembled into a single cosmid that is easily amplified in *E. coli*. The use of intron endonuclease recognition sequences flanking the ITRs enhances virus production while simplifying insertion of therapeutic gene sequences into the pLEP shuttle plasmid. The convenience of this vector system has facilitated the construction of over two hundred recombinant viruses to date.

Other embodiments and advantages of the invention will be apparent from the detailed description thereof, and from the claims.

BRIEF DESCRIPTION OF THE DRAWINGS

The application file contains drawings executed in color (FIGS. 7A, 7B, 7C, 10C, 11, 15A, 17, and 21). Copies of this patent or patent application with color drawings will be provided by the U.S. Patent and Trademark Office upon request and payment of the necessary fee.

FIG. 8B shows a summary of quantitative RT-PCR and PCR results. Each determinant was the average of three experiments.

FIG. 13A shows a schematic diagram of the components of various auto-regulatory synthetic TetO promoters. FIG. 13B shows a comparison of the strength of auto-regulatory synthetic TetO promoters bearing different basal elements, in the presence and absence of tetracycline, using GFP as a marker in HepG2 cells.

DETAILED DESCRIPTION

Described herein are systems for the regulated self-rearrangement of DNA vectors, for example, gene therapy vectors. Such regulated self-rearrangement has the potential to prevent unwanted expression of vector genes not required for a therapeutic effect, and to allow the stable association of the therapeutic gene with the target cell.

The essential elements of the regulated DNA rearrangement system are a gene that encodes one or more proteins that induce DNA rearrangement, a method for regulating the activity of those proteins or their abundance, and a target DNA sequence on which those proteins act. Particularly desirable are methods for regulating the activity of the proteins or their abundance which can be easily carried out on an intact organism, such as administration or withdrawal of a drug, hormone, or environmental stimulus such as heat or irradiation, which induces the activity or abundance of the proteins which cause DNA rearrangement.

Especially desirable are regulated DNA rearrangement systems in which all of the components can be delivered in a single vector. An example of this is a virus that bears both the cis-acting sequences for DNA rearrangement as well as the protein or proteins that act on those sequences, and the regulatory apparatus which controls the activity or abundance of those proteins. However, it is not necessary that the different elements be encoded in a single nucleic acid.

The important elements of this strategy are: the compromise of vector gene function by regulated rearrangement of DNA topology, the generation of plasmid circles from vector DNA in a regulated manner, and the removal of enhancer or promoter elements from the vector DNA by regulated excision. It is also important that the circular DNA generated by site-specific recombination possesses a mechanism for stable association with the host genome in some form, here conferred by the EBV replicon. In other embodiments, the circular DNA might possess the ability to direct its integration into the host chromosomes by a site-specific integration. Site-specific integration into the host chromosomes may also be generated by the action of a regulated site-specific recombinase on a linear template without passing through a circular intermediate.

Figure 5:
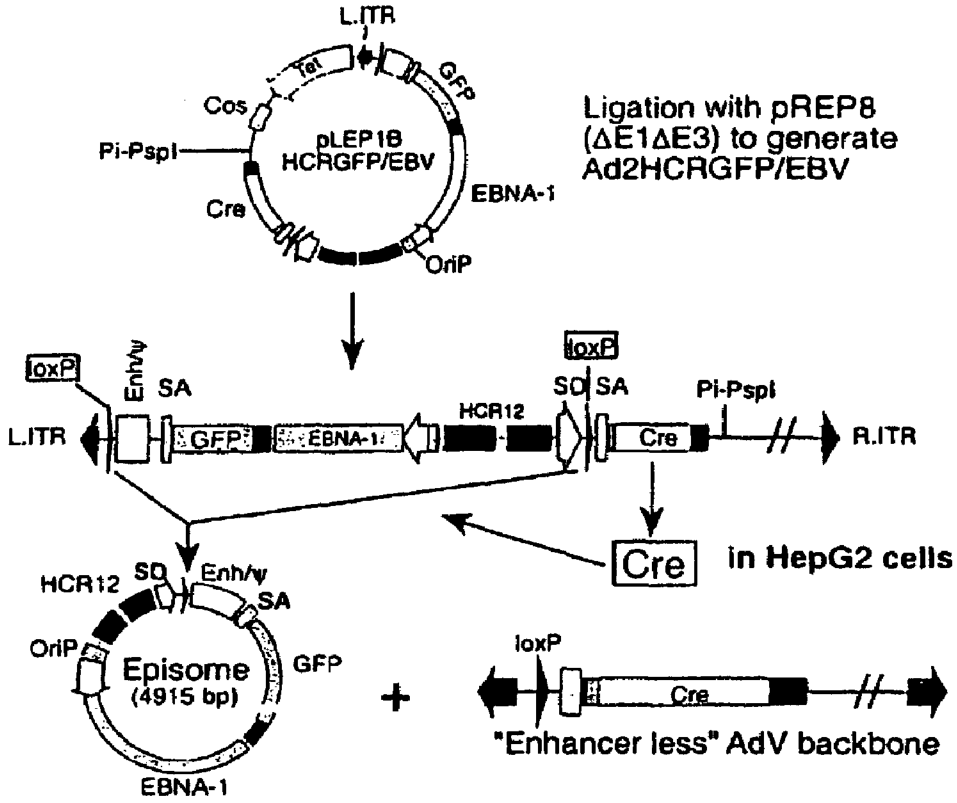
FIG. 5 is a schematic diagram showing a linear AdV that resolves into a circular episome. The elements involved in the self-directed rearrangement of the vector are shown schematically in pLEP1BHCRGFP/EBV and in the corresponding AdV. Starting from the left ITR, the elements are shown as following sequence: left ITR, 147 bp; first 34 bp loxP site; 185 bp enhancer/packaging signal; 64 bp splicing acceptor (SA) from EF1α gene first intron; 720 bp GFP cDNA; 230 bp SV40 poly(A); 1.7 kb TK-EBNA-1/OriP; 970 bp HCR12 promoter; 1 kb EF1α gene first intron containing splicing donor (SD) and acceptor (SA) sites with the second loxP site inserted at 64 bp upstream of the 3'end; 1.2 kb Cre gene tagged with AU1 and a nuclear localization signal; ~120 bp poly(A) signal and PI-PspI site. After infection of liver cells, the HCR12 promoter drives the expression of Cre which results in the cleavage of the two loxP sites. This results in the circularization of the fragment containing the EBV replicon. The excision severs the connection between the enhancer/packaging signals and the remainder of the AdV genome. The Cre gene becomes promoterless and is left on the AdV genome fragment. After excision, the HCR12 promoter drives the expression of the GFP reporter gene. The EBV replicon maintains the excised circle as an episome in host cells.

Also described herein is one particular self-rearranging vector that begins as a hybrid adenovirus vector which is capable of converting itself into two unlinked molecules, a circular and a linear DNA. After this event the linear DNA product is deleted for two important cis-acting sequences: the packaging signals, which are required for insertion of the viral DNA into the viral capsid, and the enhancer, which increases the expression of other promoters encoded in the viral DNA. The remaining linear DNA is thereby compromised in its ability to express adenoviral genes, endowing the vector with a lower immunological profile. The circular DNA generated by the excision event is a mammalian cell plasmid which has the capacity to persist by autonomous replication in the nucleus. This capacity is encoded in genetic elements derived from the Epstein Barr virus (EBV). A schematic diagram of such a vector is illustrated in FIG. 5.

Epstein Barr virus is a human herpes virus which is the etiologic agent of infectious mononucleosis and which has been implicated in the genesis of Burkitt's lymphoma, a B cell neoplasm, and is thought to be a predisposing factor for some forms of nasopharyngeal carcinoma. Approximately 85% of the adult Western population has a persistent population of B cells which contain a circular latent form of the viral-genome, maintained in cells by the action of Epstein Barr Nuclear Antigen 1 (EBNA1), a DNA replication protein that acts on the viral latent phase origin of replication, OriP. EBNA1 in and of itself is not thought to promote neoplasia; current thinking places greater weight on the actions of the EBNA2 proteins and LMP, latent membrane protein, in the inception of EBV-associated neoplasm.

Mammalian cell plasmids have been created which bear the EBNA1 gene and OriP. In nonrodent cells, these plasmids persist by replication with each transit of the cell cycle. Multiple transcription units can be borne by these plasmids, allowing regulated expression of diverse gene products.

Figure 1A:
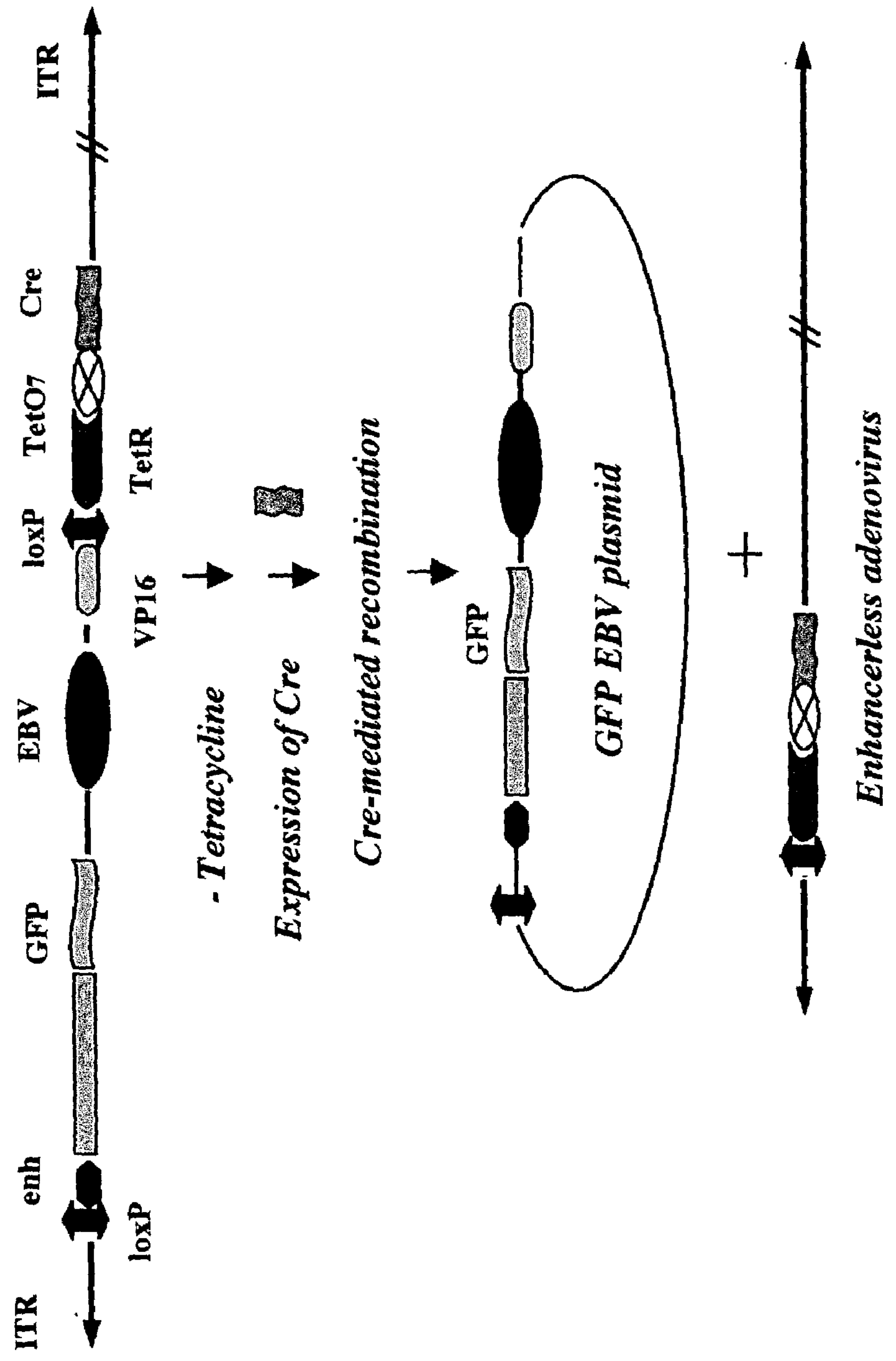
FIG. 1A is a schematic diagram of the structure of an adenoviral type A vector and its fate in a target cell. “enh” refers to the Ad2 enhancer; “GFP” refers to the marker gene green fluorescent protein; “EBV” refers to the Epstein Barr Virus replicon; “$TetO_7$” refers to a heptamer of Tet operator; “TetR” refers to the Tet repressor; “VP16” refers to the viral protein 16 of Herpes simplex virus, SD refers to the splice donor site; and SA refers to the splice acceptor site.
Figure 1B:
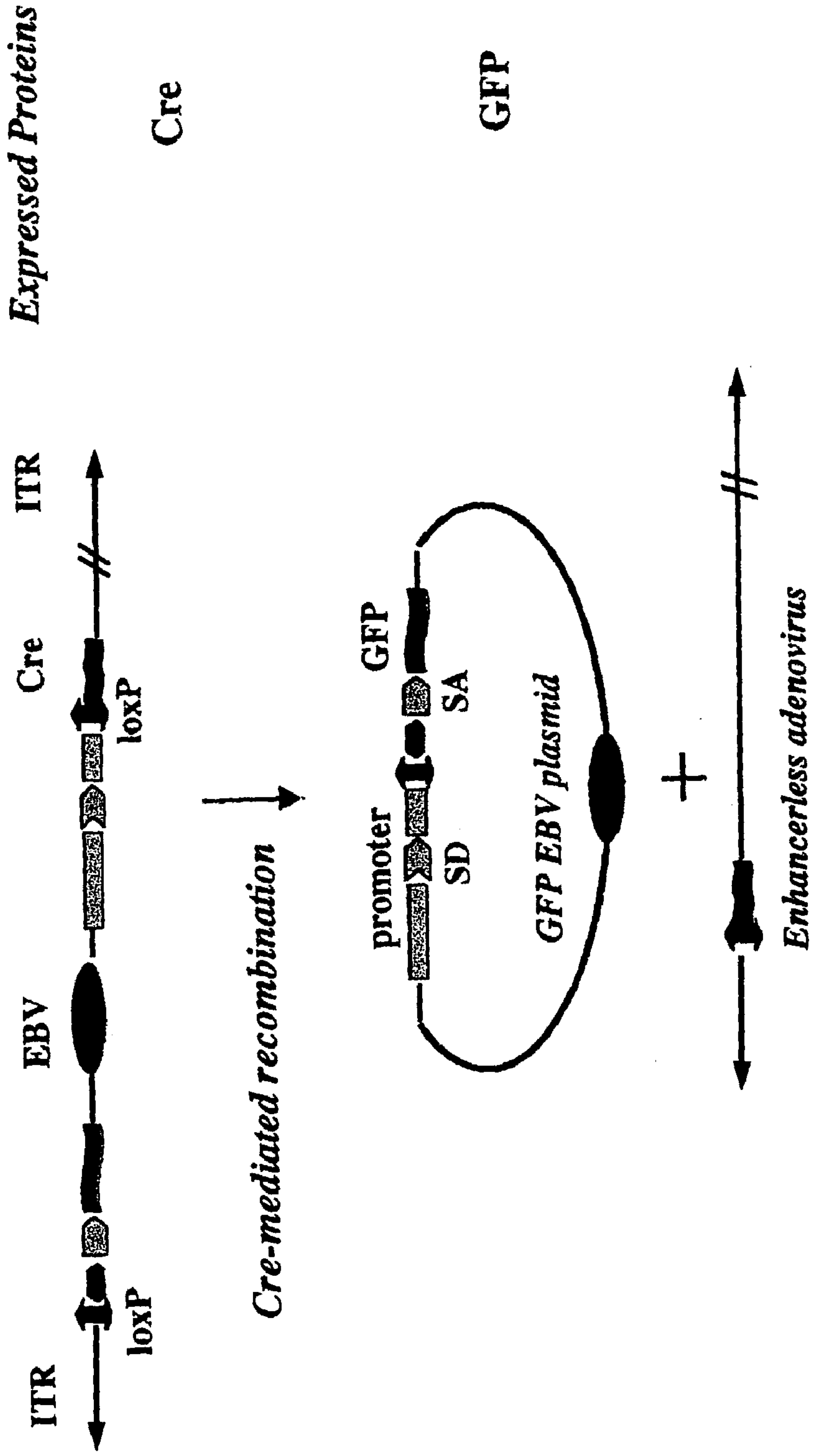
FIG. 1B is a schematic diagram of the structure of an adenoviral type B vector and its fate in a target cell. enh refers to the Ad2 enhancer; GFP refers to the marker gene green fluorescent protein; EBV refers to the Epstein Barr Virus replicon; SD refers to the splice donor site; and SA refers to the splice acceptor site.

Preferred adenoviral vectors, shown in FIGS. 1A and 1B, are linear forms of an EBV plasmid flanked by loxP sites, cis-acting sequences required for site-specific recombination directed by the bacteriophage P1 cre protein. To prepare an adenovirus bearing both the cre protein and loxP sites, it is necessary to insure that the cre protein is not expressed while the vector is being propagated in 293 cells. To lower the immunological profile of the vector, it is also desirable that the cre protein not be expressed after the vector delivered its payload to the target cell and the cre protein performed its function.

To accomplish these objectives, two general approaches have been developed for the production of adenoviral chromosomes that circularize following the regulated expression of site-specific recombinases. In each case, the vector is engineered to allow for the production of viruses in 293 cells, and to provide transitory expression of recombinase that induces rearrangement in target tissues. The major difference between the two strategies lies in the way the deinduction of recombinase is achieved.

In the first approach, adenoviral vectors are engineered to turn an activating transcription factor into a repressor upon chromosomal rearrangement. Vectors employing this approach are referred to herein as type A vectors (FIG. 1A). In the second approach, the recombinase promoter is redirected following chromosomal rearrangement. Vectors utilizing the second approach are referred to as type B vectors (FIG. 1B). In both cases a linear chromosome is converted to its circular episomal form and a resulting deleted linear form. The circular DNA contains an Epstein Barr virus (EBV) replicon, which allows synchronous replication of the episome with the host mitotic cycle (Reisman et al., Mol. Cell Biol. 8: 1822–32, 1985; Yates et al., Nature 313: 812–15, 1985). The linear DNA is deleted for the enhancer and E1 genes.

One self-regulated gene switch, employing the type A vector strategy, was designed based on the bacterial transposon Tn10 tetracycline repressor (tetR) gene. In its natural context, the tetR protein binds to specific sequences (tet operator sequences) upstream of a tetracycline resistance gene, preventing transcription of the gene unless tetracycline is present. To adapt this protein for eukaryotic gene regulation, a gene fusion is created between tetR and an active portion of a strong eukaryotic transcriptional activator, the herpes simplex virus VP16 protein. The fusion protein exerts its action on a synthetic promoter created by the insertion of multiple tet operator sequences upstream of a basal promoter element. This configuration allows high-level gene expression whenever the tetR-VP16 fusion protein binds to its cognate operator sequences. Because the tetR protein normally does not bind to its operator in the presence of tetracycline, the activity of this synthetic promoter is high in the absence of tetracycline and low in its presence.

One example of a type A vector is shown in FIG. 1A. This self-regulated gene expression cassette, present in a hybrid adenovirus, consists of a bi-directional promoter element in which central tetR binding sites are flanked by divergently oriented basal promoter elements. In one direction the promoter directs the formation of a transcript encoding the cre protein; in the other direction, the promoter directs the formation of a tetR-VP16 fusion protein. The latter differs from the conventional version in bearing a loxP site between the tetR component and the VP16 component. When tetracycline is present this gene switch is silent. As shown in FIG. 1A, upon introduction into a target cell in the absence of tetracycline, the tetR-loxP-VP16 fusion protein is produced, stimulating further production of the fusion protein, and the cre protein. The cre protein then acts to promote site specific recombination between the loxP site in the tetR-loxP-VP16 coding sequences, and a distant loxP site. As a result of this recombination, the fusion protein coding sequence is disrupted so that the promoter no longer directs the formation of a tetR-loxP-VP16 fusion protein, but gives rise to an inert tetR-loxP-VP16 fusion protein for binding to the promoter upstream elements, thereby extinguishing promoter activity.

As shown in FIG. 1A, the excised circular DNA element contains at least two transcription units. In addition, other transcription units or internal ribosome entry site elements may be used to allow the coexpression of gene products which are useful for extending the persistence of the delivered DNA, regulating expression of the gene of interest, or providing for ablation of the transduced cells once their presence is no longer desirable. In addition, the linear DNA remaining after excision of the circular gene expression plasmid lacks both viral packaging sequences and the cis-acting enhancer. Within this linear DNA, additional loxP sites may be placed to provide for the rearrangement of the remaining vector DNA in the target cell, disrupting the normal topology of the genes, and further thwarting expression.

Using the type B vector design strategy, described in greater detail below, a recombinant adenoviral gene delivery system that is capable of undergoing growth phase-dependent site-specific recombination has also been constructed.

The following examples are presented for the purpose of illustrating, not limiting, the invention.

Type B Vectors—Experimental Results

Several experimental examples for constructing type B vectors and for carrying out the general approaches of the invention are now described below.

Two-Cosmid System for Efficient Construction of Recombinant AdV

Figure 2A:
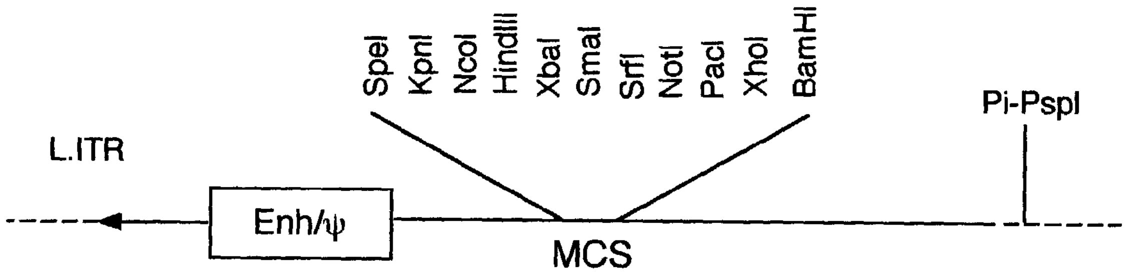
FIG. 2A shows a schematic diagram of the pLEP cosmid polylinker region and its position relative to the adenoviral left ITR. The adenovirus enhancer/packaging sequence (ψ) is boxed.
Figure 2B:
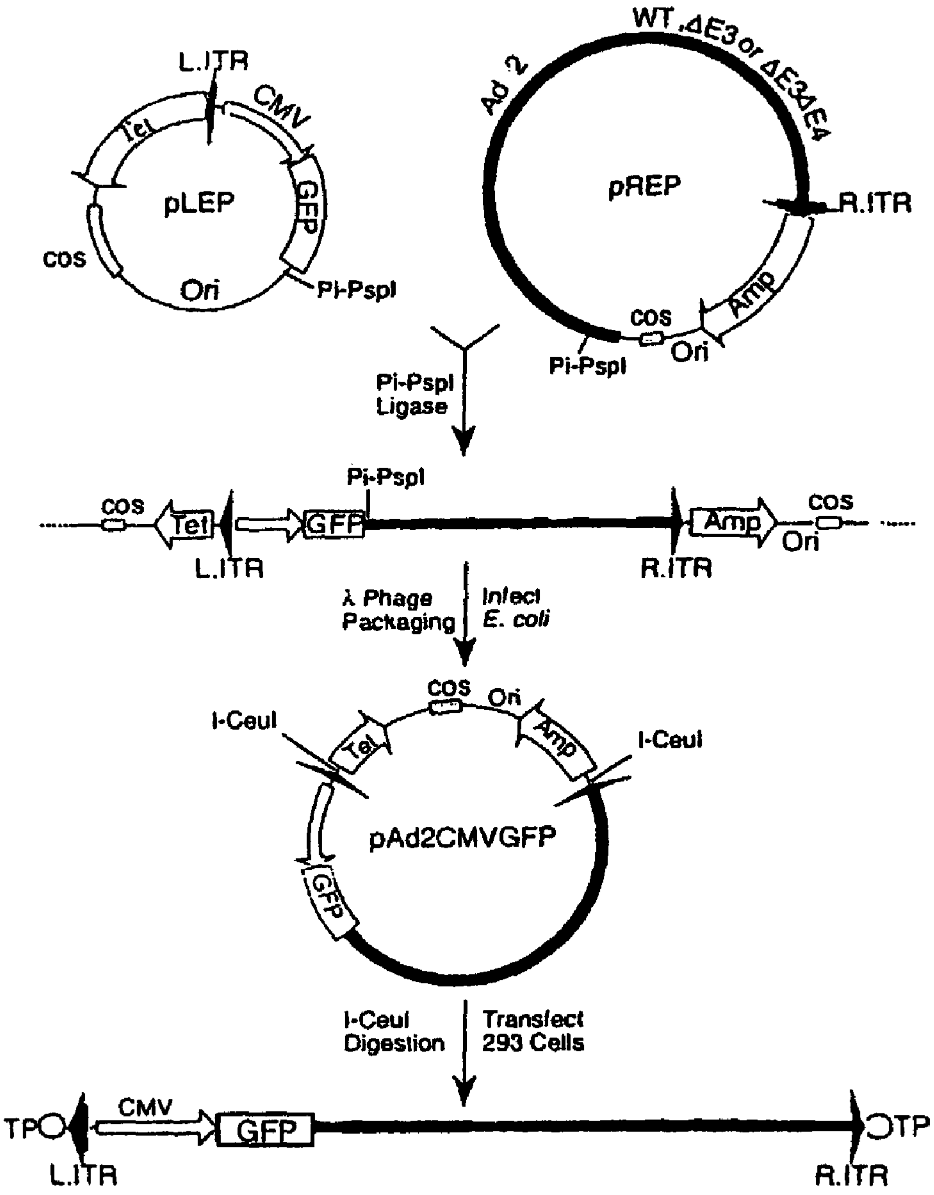
FIG. 2B is a schematic diagram showing the generation of a single cosmid encoding the AdV genome by the direct ligation of two smaller plasmids. A gene expression unit, CMVGFP, was inserted into the pLEP cosmid at the polylinker region. pLEP and pREP cosmids were digested with an intron endonuclease (PI-PspI), ligated, and packaged in vitro to generate pAd2CMVGFP. This DNA was then digested with another intron endonuclease (I-CeuI) to expose the ITRs at both ends of the viral genome. Finally, cosmid digestion mixtures were transfected into 293 cells. Plaques generated by recombinant viruses are detected in 7–10 days.

To simplify and facilitate the generation of recombinant AdV, a system was established to assemble the desired AdV genome in a single plasmid by ligation (shown in FIGS. 2A and 2B). The system consists of two component vectors, a left end plasmid, pLEP, and a right end plasmid, pREP. The left end Ad sequences (nt 1–376) in pLEP include the viral inverted terminal repeat, the cis-acting packaging sequences, and the viral enhancer. Nucleotide (nt) positions described herein refer to the wild type Ad2 sequence in GenBank (J019017). The Ad sequences are followed by the gene expression unit intended for delivery and an intron endonuclease (PI-PspI) cleavage site. The right end plasmid contains a PI-PspI site followed by the Ad2 genome from the end of the E1 locus rightward (nt 3527–35937).

pLEP is a small tractable vector for cloning, whereas pREP is much larger and contains less frequently manipulated genes. Both pLEP and pREP contain a bacteriophage λ cos site, oriented to generate a single cosmid of appropriate length for in vitro packaging following ligation of the two plasmids at the PI-PspI cleavage site. pLEP is tetracycline resistant ($Tet^r$) and pREP is ampicillin ($Amp^r$) resistant, allowing the recombinants to be selectively isolated by co-selection for both markers. In the resulting assembled cosmid, the adenoviral sequences are closely flanked by cleavage sites for the intron endonuclease I-CeuI. Digestion with I-CeuI liberates the entire recombinant AdV genome from the parent cosmid (see FIG. 2B).

Three classes of pREP have been constructed to allow the preparation of AdVs bearing E1 (pREP7; SEQ ID NO.: 2), E1 and E3 (pREP8; SEQ ID NO.: 3), or E1, E3, and E4 (pREP12; SEQ ID NO.: 4) deletions. pREP7 (SEQ ID NO.: 2) contains nt 3527–35937 of the Ad2 genome, and pREP8 (SEQ ID NO.: 3) carries an additional deletion in the E3 region (Δ nt 27901–30841). pREP12 (SEQ ID NO.: 4) has deleted open reading frames (ORF) 1–4 of the E4 region (Δ nt 34121–35469, 1348 bp). AdV generated with these cosmids should be able to accommodate 5, 8, and 10 kb inserts, respectively.

These aforementioned vectors were constructed as follows. The EcoRI to BsaI fragment that spans the ampicillin resistance gene in pBR322 was deleted and replaced by a synthetic adapter, and the bacteriophage λ cos site was inserted between the unique StyI and BsmI sites. A PCR amplified Ad2 fragment containing the left end ITR (L.ITR), enhancer elements, and the encapsidation signal (nt 1–376) was created and inserted into the adapter (FIGS. 2A, 2B) to yield the tetracycline-resistant left-end plasmid pLEP. The right end of Ad2 from the AflII site to the right end (nt 3527–35937) was assembled into an ampicillin resistant cosmid vector, pACKrr3 (SEQ ID NO.: 1), by multiple steps of PCR amplification and fragment interchange. The resultant cosmid was termed pREP7 (SEQ ID NO.: 2). To expand vector capacity, two deletions were incorporated into the pREP7 (SEQ ID NO.: 2) cosmid, an E3 gene deletion (nt 27901–30841, 2840 bp); cosmid pREP8 (SEQ ID NO.: 3) and a 1.3 kb deletion (nt 34121–35469) in the E4 region of the Ad2 region; pREP12 (SEQ ID NO.: 4)

An example of the construction of an AdV carrying a CMV-GFP expression unit is outlined in FIG. 2. pLEPCMVGFP ($Tet^r$) was digested with PI-PspI and ligated to the pREP7 (SEQ ID NO.: 2; ΔE 1, $Amp^r$) digested with the same enzyme. The ligation mixture was packaged with λ phage extracts (MaxPlax lambda packaging extracts, Epicentre Technologies) and a fraction of the packaged phage was used to infect a recombination-deficient *E. coli* host, with selection for the assembled plasmid on Amp/Tet plates. Transductants containing pLEP fused to pREP were selected on agar containing 25 μg/ml ampicillin and 12.5 μg/ml tetracycline (Amp/Tet). Colonies were selected and DNA isolated (Qiagen). DNA was used either for restriction analysis or for tranfection of 293 cells as described herein.

Figure 3A:
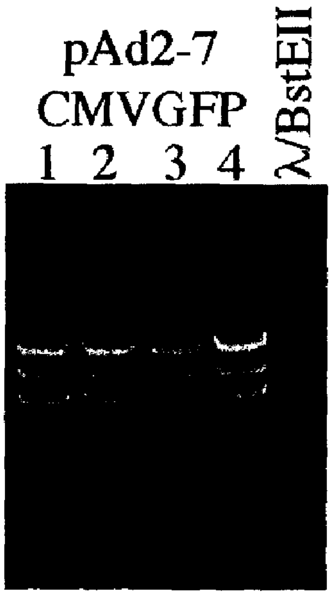
FIG. 3A shows the restriction analysis of cosmids carrying the full length AdV DNA showing uniform generation of the desired vector DNA. 2 μg DNA samples from four pAd2-7CMVGFP colonies were digested with Bgl II, resolved on a 1% agarose gel and stained with ethidium bromide. The predicted sizes of the DNA fragments are: 13261, 7684, 5228, 5088, 2284, 1757, 1549, 1270, 351, and 275 base pairs (bp). The 5228 and 5088 fragments appear as a doublet, and the 351 and 275 bp fragments are too small to be seen on the gel.
Figure 3B:
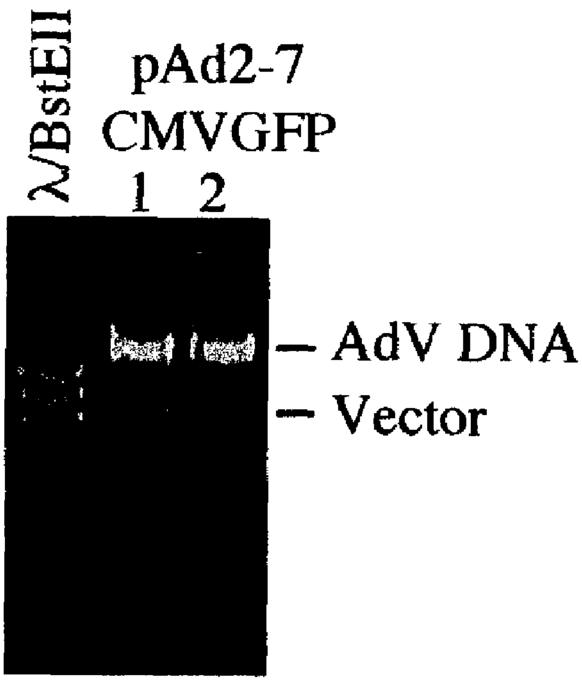
FIG. 3B shows the release of the recombinant Ad DNA from cosmids by I-CeuI digestion. 2 μg of pAd2-7CMV DNA from two clones was digested with I-CeuI. The position of the released recombinant AdV DNA and the vector fragments of approximately 35 kb and 5 kb, respectively, are indicated.

FIG. 3A shows typical results for the Bgl II digestion pattern of a pLEP3CMVGFP/pREP7 hybrid cosmid, pAd2-7CMVGFP DNA. Because of the size minimum (~40 kbp) for λ phage in vitro packaging and the double antibiotic selection, most of the colonies growing on Amp/Tet plates were the desired hybrid cosmids, and undesired rearrangements were rarely seen. In the present example, all four pAd2-7CMVGFP clones exhibited the digestion pattern predicted from the inferred sequence. The entire recombinant AdV genome was then released from the cosmid by I-CeuI digestion (FIG. 3B). I-CeuI digestion leaves ten nucleotides to the left of the left ITR and eight nucleotides to the right of the right ITR. Short flanking sequences have been reported to be eliminated during replication of recombinant viruses after transfecting the DNA into 293 (human embryonic kidney) cells (Hanahan et al., Mol. Cell. Biol. 4:302–309, 1984).

The digestion reaction can be transfected into 293 cells without purification as follows. 293 cells, obtained from Microbix Bisosystems (Ontario, Canada), were cultured in 10 cm dishes in complete Dulbecco's Modified Eagle's Medium (DMEM) supplemented with 10% FBS, 2 mM glutamine and penicillin/streptomycin (Gibco BRL), and maintained at 37° C. and 5% $CO_2$ atmosphere in an incubator. Cells were grown to ~50% confluence on the day of transfection. Ten μg of cosmid DNA were digested with I-CeuI in a volume of 50 μl. The reaction mixture was transfected into 293 cells by calcium phosphate precipitation (Graham and Prevec, Manipulation of adenovirus vectors, p. 109–128, In E. J. Murray (ed.), Methods in Molecular Biology, vol. 7, Humana, Clifton, N.J., 1991) without purification. After transfection, cells were cultured and examined daily for the appearance of cytopathic effects (CPE). Virus propagation, purification, plaque assay, and viral DNA isolation were performed using established protocols (Graham and Prevec, supra). At day six post-transfection, 5–30 viral plaques/10 cm dish/10 μg DNA were usually apparent, which compared favorably with the 30–50 plaques/10 cm dish/10 μg DNA found for 293 cells transfected with purified wild type Ad2 DNA.

To compare the efficiency of recombinant virus production, similar viruses were also generated by homologous recombination. 20 μg of pREP7 (SEQ ID NO.: 2) was co-transfected into 293 cells with 10 μg of a plasmid encoding the left end of the adenoviral genome and a green fluorescent reporter gene (pLITREF1αGFP). pLITREF1αGFP contained the Ad2 left end nt 1–376, an EF1α promoter/GFP expression unit and Ad2 sequence (from 3525–8120) that overlaps with the same sequence in pREP7 (SEQ ID NO.: 2). This overlap fragment served as the region for homologous recombination. Each co-transfection was performed in duplicate. Initial plaques took longer to appear (14 days post transfection) and were less abundant (0–3 plaques per plate).

Data in the literature suggest that exposed ITR ends favor efficient virus production (Hanahan et al., supra). To assess the importance of this effect, an AdV cosmid, pIAdEF1αGFPB, in which the AdV ITRs were flanked with a different restriction site at each end was constructed. pIAdEF1αGFPB DNA was digested with BsaBI to expose the right ITR, I-CeuI to expose the left ITR, or the two enzymes were used together to expose both ends. Digested cosmid DNA samples were transfected into 293 cells and plaques were allowed to develop. Virus propagation, purification, plaque assay, and viral DNA isolation were performed using established protocols described in Graham and Prevec. (Manipulation of adenovirus vectors, In E. J. Murray (ed.), Methods in Molecular Biology, vol. 7. Humana, Clifton, N.J., pp. 109–128, 1991).

Figure 4A:
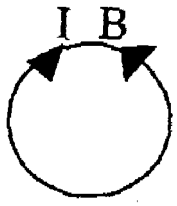
FIG. 4A shows the appearance of plaques in 293 cells transfected with 10 μg of pIAdGFPB with no ITR exposed (undigested), one ITR exposed (BsaBI or I-CeuI), or both ITRs exposed (BsaBI plus I-CeuI). Values represent the mean plaque counts per dish and the time required for plaque development in 293 cells from three separate experiments. "I" designates I-CeuI; and "B" designates Bsa BI.
Figure 4A:
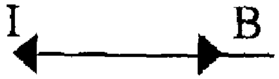
Figure 4A:
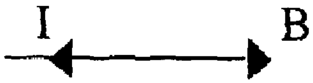
Figure 4A:
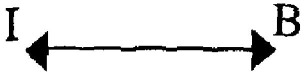
Figure 4B:
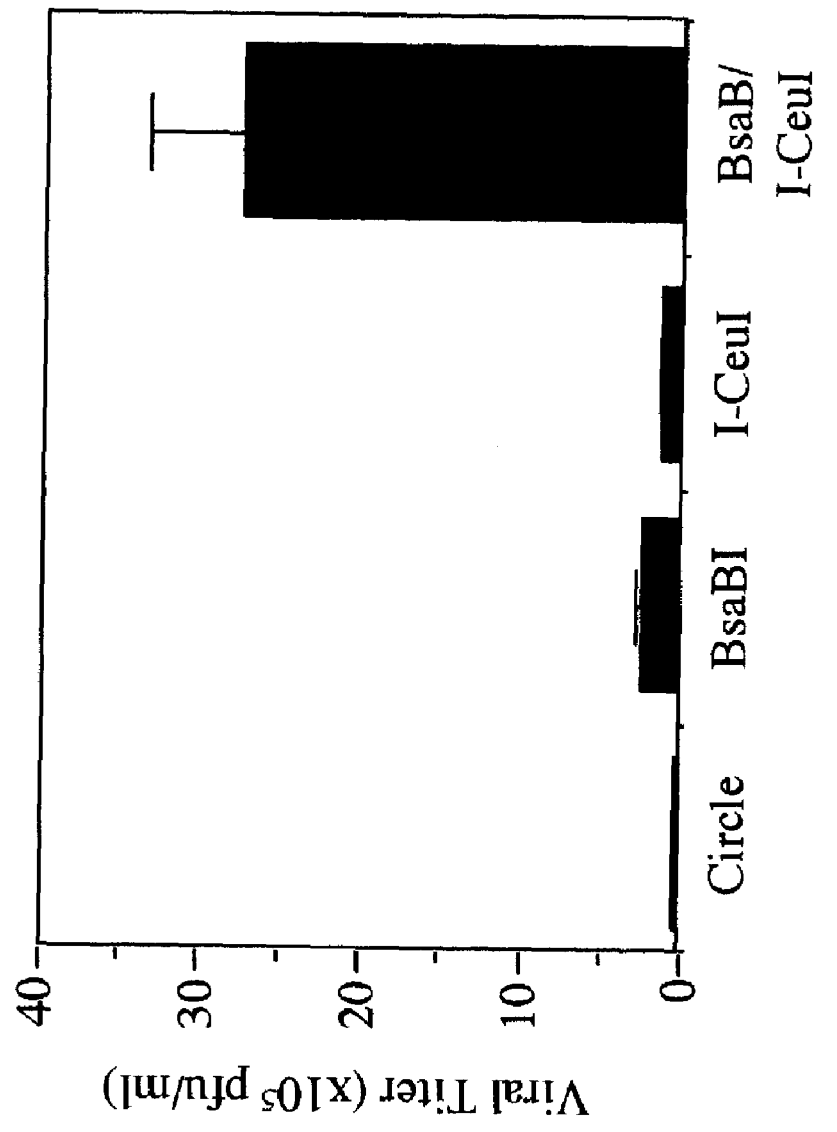
FIG. 4B shows the viral titers obtained from plaques that were allowed to grow over 10 days after transfection. Viruses were harvested and the titer of each virus stock was determined by a GFP based semi-quantitative titration procedure described herein. Values represent the mean±SE of three independent determinations.

Ten days after transfection the viruses were harvested and viral titers were determined. The average titer for the viral stocks (FIGS. 4A and 4B) was $1.3\times10^4$ pfu (plaque forming unit)/ml from transfection with undigested DNA; $2.4\times10^5$ pfu/ml from BsaBI linearized DNA (free right ITR); $1.1\times10^5$ pfu/ml from I-CeuI linearized DNA (free left ITR); and $2.7\times10^6$ pfu/ml for the BsaBI/I-CeuI double digested DNA (both ITRs free). Thus liberation of each end resulted in an approximate increase in the efficiency of generating virus by a factor of ten (FIGS. 4A and 4B).

Construction of an AdV Capable of Self-Rearrangement

One approach to attenuating adenoviral gene expression and improving transgene persistence is the creation of viruses capable of undergoing internal, self-directed rearrangement upon delivery to the target tissue. In principle, this objective can be achieved through the regulated expression of site-specific recombinases in vectors that contain the cis-acting target of recombinase action. To allow such vectors to be created, the recombinase activity must be suppressed during propagation in the packaging cell line. As described in more detail below, the use of a lineage-specific promoter to control recombinase expression has been successfully employed to achieve this end.

An example of this is shown in FIG. 5. The expression of Cre recombinase was controlled by a liver-specific promoter constructed as follows. The human hepatic control region 1 and 2 (HCR1 and 2) of the ApoE/C gene locus (Allan et al., J. Biol. Chem. 270:26278–81, 1995; and Dang et al., J. Biol. Chem. 270:22577–85, 1995) were amplified by PCR using 293 cell genomic DNA as the template. The following primers were used to amplify both HCR1 and HCR2 fragment: HCRtop-5'gcggaattcggcttggtgacttagagaacagag 3' (SEQ ID NO.:5); HCRbot-5' gcgggatccttgaacccggaccctctcacacta 3' (SEQ ID NO.:6). The amplified PCR fragments (~0.39 kb) were cloned into pUC19. The HCR1 and HCR2 sequences were confirmed by dideoxy DNA sequencing. The two fragments were assembled in a head to tail orientation, fused with a synthetic basal TATA element and cloned in a parental pLEP vector containing a GFP reporter gene. The resultant plasmid was named pLEPHCR12GFP. The synthetic liver-specific, as demonstrated below, provided a means to control Cre recombinase expression during propagation of the vector in 293 cells, and allowed for testing the consequences of abstracting the enhancer from the linear vector DNA upon delivery of the DNA to the target cells.

In 293 cells, this promoter is silent, allowing the viral chromosome to be propagated with minimal rearrangement. Any rearranged viruses that are formed lack packaging signals and so disappear from the pool of propagating vectors. In liver cells the Cre recombinase is induced by the action of the tissue-specific promoter. The resulting Cre-induced recombination excises a circular episome and redirects the transcriptional output of the liver-specific promoter so that it directs the synthesis of the transgene of interest. The remaining linear fragment consists of an adenoviral genome lacking the enhancer and packaging signals and a Cre expression unit devoid of promoter sequences.

In the form discussed here, one loxP site is located at nucleotide 147 of the Ad2 genome, between the left ITR and the enhancer/packaging sequences, and the second loxP site is placed inside an intron a few bases upstream of the splice acceptor sequence. Hence the loxP site does not appear in the resulting mature transcript. The Cre coding sequence that remains on the right end linear fragment after rearrangement lies downstream from a splice acceptor that lacks a splice donor or upstream promoter sequences. This effectively terminates the expression of Cre following excision.

Prior to recombination, the Cre recombinase gene is under the control of a synthetic promoter (referred to as HCR12), consisting of hepatic locus control elements from the human ApoE/C locus fused to the first intron of the human EF1α gene. After cyclization the HCR12 promoter lies upstream of the transgene (in this case GFP) and the distal segment of the intron (beyond the loxP site) contains the adenoviral enhancer. To facilitate manipulation of the plasmids in *E. coli*, the human IgG 1 hinge-CH2 intron (118 bp) was inserted in the Cre coding sequence at nucleotide 237, suppressing Cre expression in bacteria. The circularized episome contains the latent origin of replication (OriP) and trans-acting DNA replication protein (EBNA-1) of Epstein Barr virus, and hence is capable of autonomous replication in synchrony with the host mitotic cycle (Yates et al., Nature 313:812–815, 1985).

Using the two cosmid system described above, the pLEP plasmid containing the self-resolving components, pLEP1BHCR12, was ligated with pREP8 (SEQ ID NO.: 3; ΔE1ΔE3) to create pAdVHCRGFP/EBV. The latter was digested with I-CeuI and transfected into 293 cells. Appearance of plaques from AdVHCRGFP/EBV was retarded (by 8 days) compared to non-rearranging viruses, perhaps as a result of basal expression of the liver-specific promoter in 293 cells. However high titer viral stocks of $10^{12}$ nominal (absorbance-determined) particles/ml was achieved.

Rearrangement in Target and Nontarget Cells

To test excision efficiency, HepG2 (hepatocellular carcinoma) and Hela (cervical carcinoma) cells, obtained from ATCC, were infected with virus at a multiplicity of infection (moi) of 1,000 nominal particles/cell. This titer corresponds to approximately 10 plaque forming units per cell. For these experiments, HepG2 and Hela cells were seeded in 35 mm dishes and cultured to approximately 80% confluence in DMEM/FBS as described herein. Cells were infected with the desired multiplicity of virus in a volume of 1 ml at 37° C. for 2 hours. At the end of the incubation, cells were washed with PBS twice and cultured in 2 ml of medium. Cells were collected in parallel at desired points for low molecular weight DNA and RNA extraction. Cells were examined for GFP expression by fluorescence microscopy (Olympus, IX70) or microtiter plate reader (PerSeptive Biosystem, CytoFluor II) before extraction of DNA for analysis of chromosomal rearrangement.

Figure 6A:
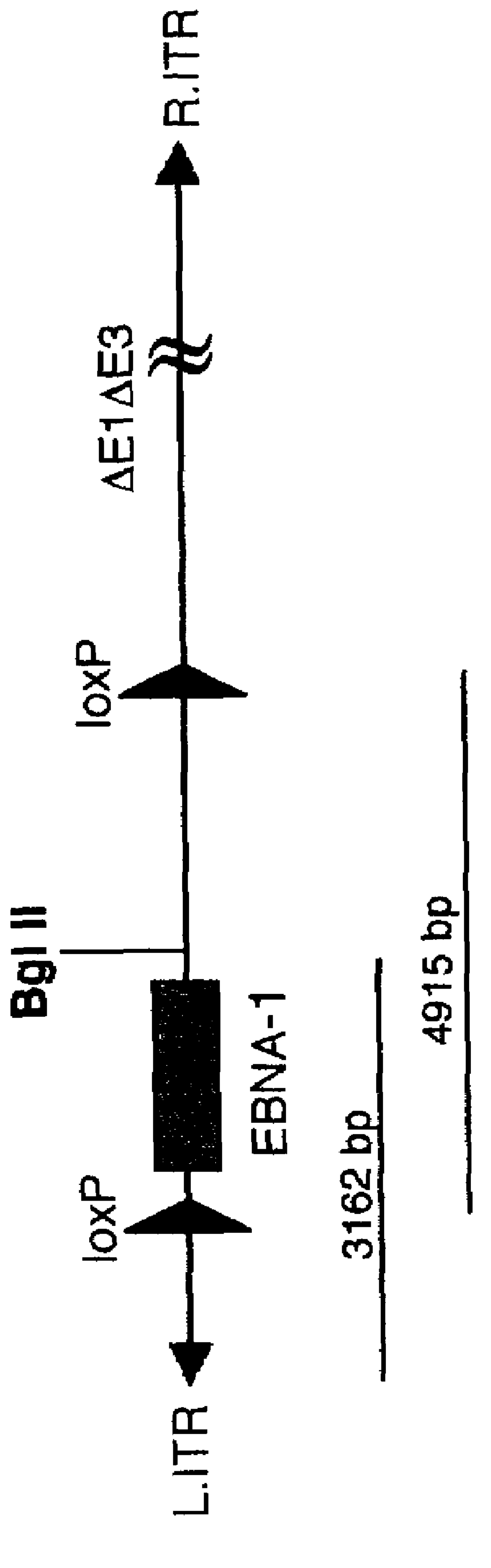
FIG. 6A is a schematic representation of the loxP sites and EBNA-1 locations in the AdV genome. The relevant Bgl II site is also shown.
Figure 6B:
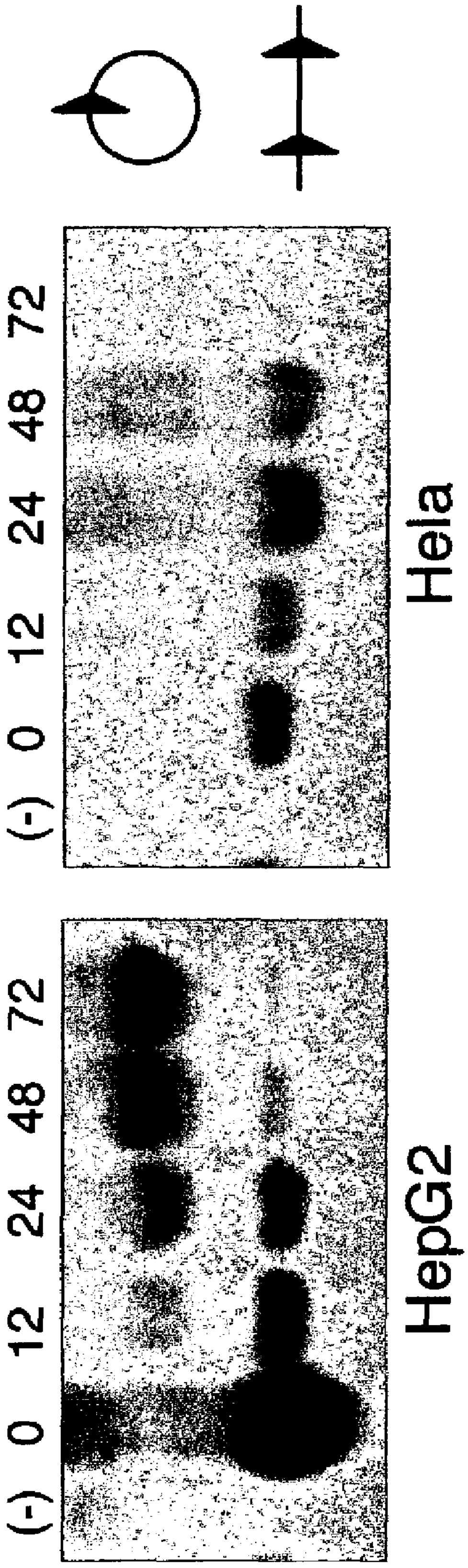
FIG. 6B shows the time course of rearrangement in HepG2 and Hela cells at an equal multiplicity of infection (moi) of 1,000 particles per cell. Cells were infected with Ad2HCRGFP/EBV viruses for 2 hours at 37° C. Hirt DNA samples were extracted from the cells. ~5 μg of Hirt DNA samples were digested with Bgl II, fractionated on a 1% agarose gel, and analyzed by Southern blot techniques using a $^{32}$P-labeled EBNA-1 fragment as the hybridization probe.

DNA analysis of chromosomal rearrangement was performed as follows. 5 μg of Hirt DNA was digested with Bgl II and analyzed by DNA blot techniques using a labeled EBNA-1 gene fragment as probe (FIG. 6). The Bgl II fragment from the non-circularized AdV is 3162 bp, generated from the 5 'end of the AdV to the first BglII site in the AdV. The circularized fragment created from the two loxP sites has a size of 4915 bp (FIG. 6A). Densitometry revealed that at 72 hours post infection, 95% or more of the input genomes had undergone circularization in HepG2 cells. In contrast, low but detectable levels of circularized fragment was visualized in Hela cells infected at the same time and at the same multiplicity of infection used for the HepG2 cells (FIG. 6B).

At the time of infection (t=0, FIG. 6B), the amount of input viral DNA detected by DNA blot was higher for HepG2 cells than for Hela cells when similar virus multiplicities were applied (moi of 1,000). This may reflect differences in AdV adsorption or infection efficiency between the two cell types, possibly as a result of the lower levels of coxsackievirus-adenovirus receptor on the Hela cells surface. To achieve similar viral genome input into HepG2 and Hela cells, Hela cells were infected with ten-fold more virus (moi of ~10,000) than HepG2 cells (moi of 1,000). Episomal DNA samples were extracted and analyzed by blotting. The results (FIG. 6C) indicated that when comparable amounts of viral genome are present in the nucleus, the cyclization rate in both cell types was similar. Because the level of subsequent GFP expression is much higher in HepG2 cells than in HeLa cells (FIG. 7A), it is likely that very small amounts of Cre recombinase suffice to promote rearrangement, and that recombinase expression is not limiting for rearrangement in either HepG2 or HeLa cells.

Figure 6C:
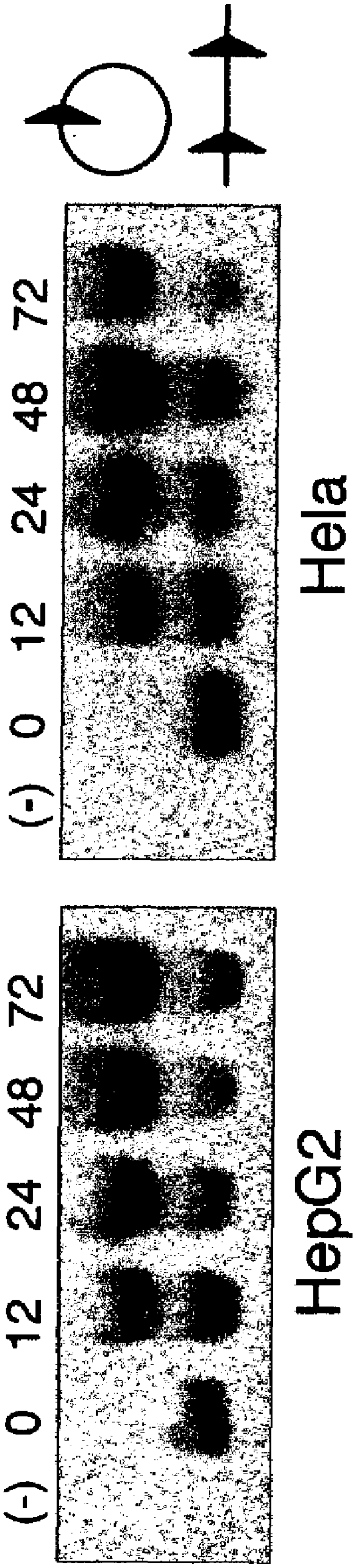
FIG. 6C shows the DNA blot results obtained from Hela cells infected at a moi of 10,000; and HepG2 at 1,000. The upper bands (4915 bp) represent the circularized DNA fragments whereas the lower bands (3162 bp) represent the non-circularized AdV.
Figure 7A:
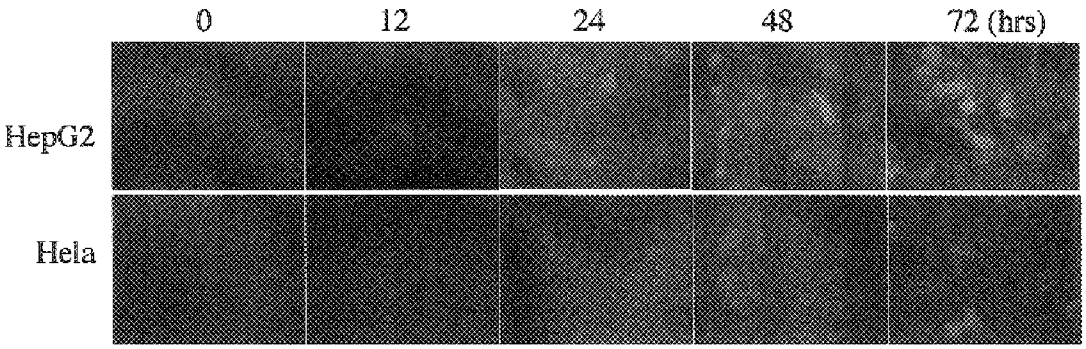
FIG. 7A shows green fluorescent protein (GFP) expression in liver and non-liver cells infected with the Ad2HCRGFP/EBV viruses. Cells were cultured in 35 mm dishes and infected with the Ad2HCRGFP/EBV virus at desired moi. HepG2 cells were infected with 1,000 particles per cell, whereas Hela cells were infected with a moi of 10,000. GFP expression was examined at the indicated time points after infection. Fluorescent cells were photographed using an Olympus SC35 mm camera mounted on an Olympus IX70 fluorescent microscope, at 200× magnification, using a filter with peak excitation and emission wavelengths of 450 nm and 510 nm, respectively.

GFP expression cannot be detected until rearrangement has taken place, so the measurement of the fraction of GFP positive cells provided a simple alternate method for assessing the degree of productive rearrangement. FIG. 7A shows that GFP expression developed quickly in transduced HepG2 cells, but that only a few GFP positive cells can be detected in Hela cells infected with a ten fold higher moi, conditions that allow circularization to a comparable extent to that seen in HepG2 cells (FIG. 6C).

Figure 7B:
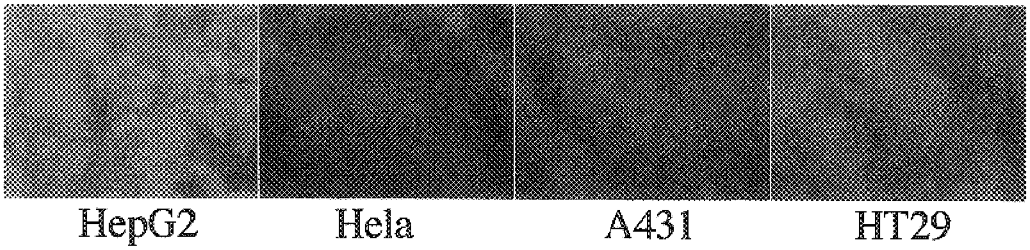
FIG. 7B shows the expression of GFP in HepG2, Hela, A431, and HT29 cells. Cells were seeded in 35 mm dishes and infected with the Ad2HCRGFP/EBV virus at a moi of 10,000 particles per cell. GFP expression was examined at 72 hours after infection.

The HCR12 promoter specificity was also tested by infecting two additional non-hepatic cell lines, A431 (human epidermoid carcinoma) and HT29 (human colon adenocarcinoma), with the Ad2HCRGFP/EBV vector. Both cell lines were obtained from ATCC and cultured using DMEM/FBS as described herein. A few cells, with weak GFP signal, were detected at 72 hours after infection in these cells (FIG. 7B). In contrast, these non-hepatic cells could be infected efficiently with a first generation AdV, Ad2CMVGFP virus (data not shown), indicating that the low GFP signal was not due to the low infectivity of these cells by AdV.

Figure 7C:
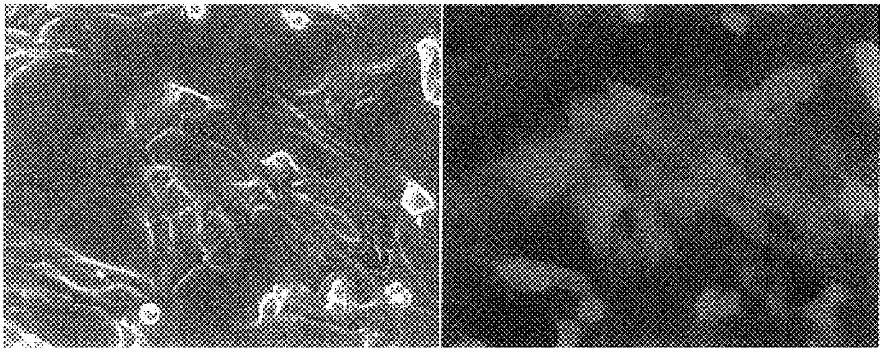
FIG. 7C shows the expression of GFP in human primary hepatocytes. These cells were photographed under bright field (left) and fluorescent conditions (right).

To further assess the utility of the AdV genome rearrangement, primary human hepatocytes were infected with the Ad2HCRGFP/EBV vector. For these experiments, primary human hepatocytes, generously provided by Dr. Albert Edge (Diacrin, Inc., Charlestown, Mass.) were isolated and cultured as described by Gunsalus et al. (Nat. Med. 3:48–53, 1997), infected with adenovirus, and GFP expression was analyzed. As shown in FIG. 7C, GFP expression was readily detected 72 hours after infection.

Diminished Viral Gene Expression in Rearranged AdV

After excision, the adenovirus major enhancer/packaging signal segregates with the episomal DNA, yielding a linear fragment containing the remainder of the AdV genome without this important cis-element (FIG. 5). To assess the impact of enhancer deletion, PCR amplification and quantitative RT-PCR measurement of late viral gene expression was performed as follows.

Four μg of total RNA was reverse transcribed into cDNA using M-MLV RT by a standard protocol (Promega). 1 μl of the cDNA from each sample was used in subsequent PCR reactions. PCR primers were designed to amplify the tripartite leader sequence of the adenovirus late genes: TPL1-5' act ctc ttc cgc atc gct gt 3' (SEQ ID NO.: 7) and TPL2-5' ctt gcg act gtg act ggt tag 3' (SEQ ID NO.:8). For detection of the AdV genome in the Hirt DNA samples, 1 μg DNA was employed in the PCR amplification using the following primers which are specific for the adenovirus DNA in the fiber gene: Fiber1-5' ccg cac cca cta tct tca ta 3' (SEQ ID NO.: 9) and Fiber2-5' ggt gtc caa agg ttc gga ga 3' (SEQ ID NO.: 10). PCR reactions were performed as 95° C. 30 seconds; 54° C. 30 seconds; 72° C. 30 seconds for 30 cycles. All amplified products were analyzed on a 2% agarose gel.

For quantitative PCR, a molecular beacon based universal amplification and detection system was used (Intergen). A common leading sequence (Z sequence, 5' act gaa cct gac cgt aca 3') was added to the TPL1 and Fiber1 primers. The TPL2 and Fiber2 primers, described above, were used in the quantitative PCR reactions. 1 μl of the cDNA and one μg of Hirt DNA from each sample were used in the assay. The PCR were carried out in a 96-well spectrofluorometric thermal cycler (Applied Biosystems Prism 7700). The number of template molecules in the PCR reaction was calculated from the standard curve using linearized plasmid as templates.

Figure 8A:
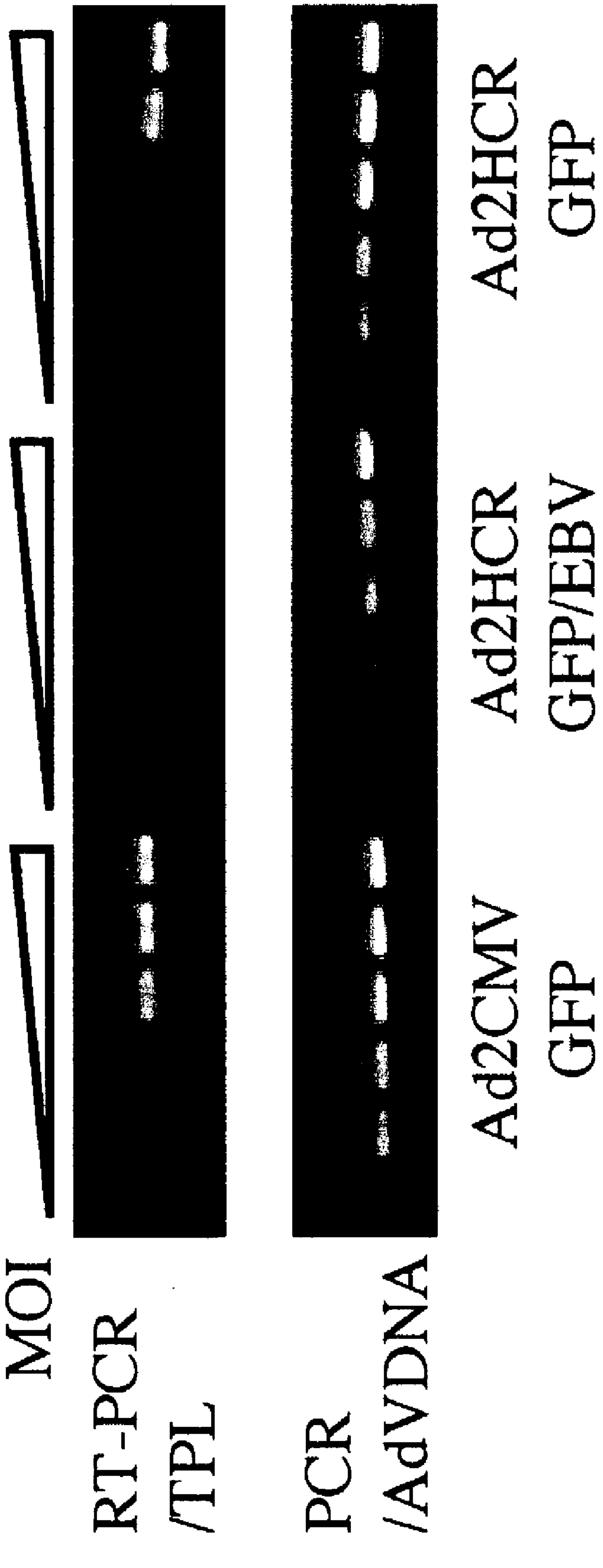
FIG. 8A shows the results of RT-PCR that was performed to detect the tripartite leader sequence (upper panel) for virus late gene expression; and PCR was performed in the DNA samples for detection of the AdV genomes. The specific target sequences are described in detail infra. PCR analyses of adenovirus late gene expression in cells infected with the first generation AdVs or the self-resolving Ad2HCRGFP/EBV was analyzed. HepG2 cells were cultured in 35 mm dishes and infected with increasing moi (0, 10, 100, 1000, 10,000, and 100,000) of adenoviral vectors. RNA and DNA were isolated in parallel from the cells at 72 hours after infection.

As most late adenoviral genes transcripts share a common ~200 bp tripartite leader sequence (TPL) (Akusjarvi and Persson, Nature 292:420–6, 1981), the TPL sequence was chosen as a marker of viral gene expression. HepG2 cells were infected with the first generation vectors Ad2CMVGFP and Ad2HCRGFP, or the self-resolving vector, Ad2HCRGFP/EBV, using increasing multiplicities of infection. Total cellular RNA and low molecular weight DNA were isolated in parallel as described by Hirt (J. Mol. Biol. 26:365–9, 1967) and total RNA was prepared using RNAzol solution (Tel -Test. Inc.). RT-PCR was performed to quantitate the amount of RNA encoding the TPL in the cDNA samples. PCR amplification of a 201 bp fiber gene fragment from the AdV genome was used to detect the amount of viral genome in the DNA samples. A representative result of three experiments is shown in FIG. 8A. TPL sequences were detected, 72 hours post-infection, with either 100 or 1000 viruses infected per cell, using both of the first generation adenoviruses (upper panel).

In contrast, no TPL signal was detected in the self-resolving Ad2HCRGFP/EBV infected cells, even at a moi of 100,000/cell. PCR amplification of the AdV fiber gene revealed comparable levels of AdV genomic DNA in cells infected at comparable moi's. (FIG. 8A, lower panel). The cDNA samples in which the TPL signals were detected were further analyzed by real-time fluorescence PCR. The corresponding genomic DNA samples were also analyzed to determine the number of AdV genomes present in each sample. The results are summarized in FIG. 8B. There were approximately $1\times10^4$ TPL per $1\times10^6$ AdV genomes detected in the Ad2HCRGFP infected cells, but no detectable TPL in the self-resolving Ad2HCRGFP/EBV infected cells. These results indicate that adenoviral gene expression was dramatically reduced by the separation of the viral enhancer sequences occasioned by the re-arrangement of the self-resolving vector.

Type A And Type B Vectors—Experimental Results

Additional experimental examples now follow that further illustrate the general approaches of the invention relating to using and constructing type A and type B vectors. For generating such adenoviral vectors, DNA sequences important for gene expression in the target tissue were placed between two loxP sites. The first loxP site was inserted between the Ad2 left-end inverted terminal repeat (ITR) and the enhancer sequence, replacing a BspLU11I and BstZ17 fragment of Ad2. A target gene expression cassette, comprising a promoter, a gene of interest, polyadenylation signals, the EBV replicon, and site specific recombinase expression unit were inserted in place of the E1 locus.

In type A adenoviral vectors, the second loxP site is placed between TetR and VP16, preserving the coding frame of both (FIG. 1A). A bidirectional promoter in which a central heptamer of tetracycline operator sites (TetO) (Gossen and Bujard, Proc. Natl. Acad. Sci. USA 89:5547–5551, 1992) was flanked by two divergently oriented basal elements, directs the expression of TetR loxP VP16 from a synthetic TATA element, whereas Cre recombinase is controlled by the same heptamer of operator upstream of the HIV LTR basal element.

In the case of type B viruses (FIG. 1B), the second loxP site was inserted in the first intron of the Ef1α gene, which contains the transcription stimulating sequences described herein. In addition, a splice acceptor sequence was added to the 5' end of the coding sequence of the gene of interest. To avoid rearrangement during plasmid construction in bacteria, the Cre recombinase coding sequence was interrupted by the addition of the human IgG1 hinge-CH2 intron (between amino acids Q78 and A79), as described herein.

Designing a Compact EBV Replicon

Figure 9A:
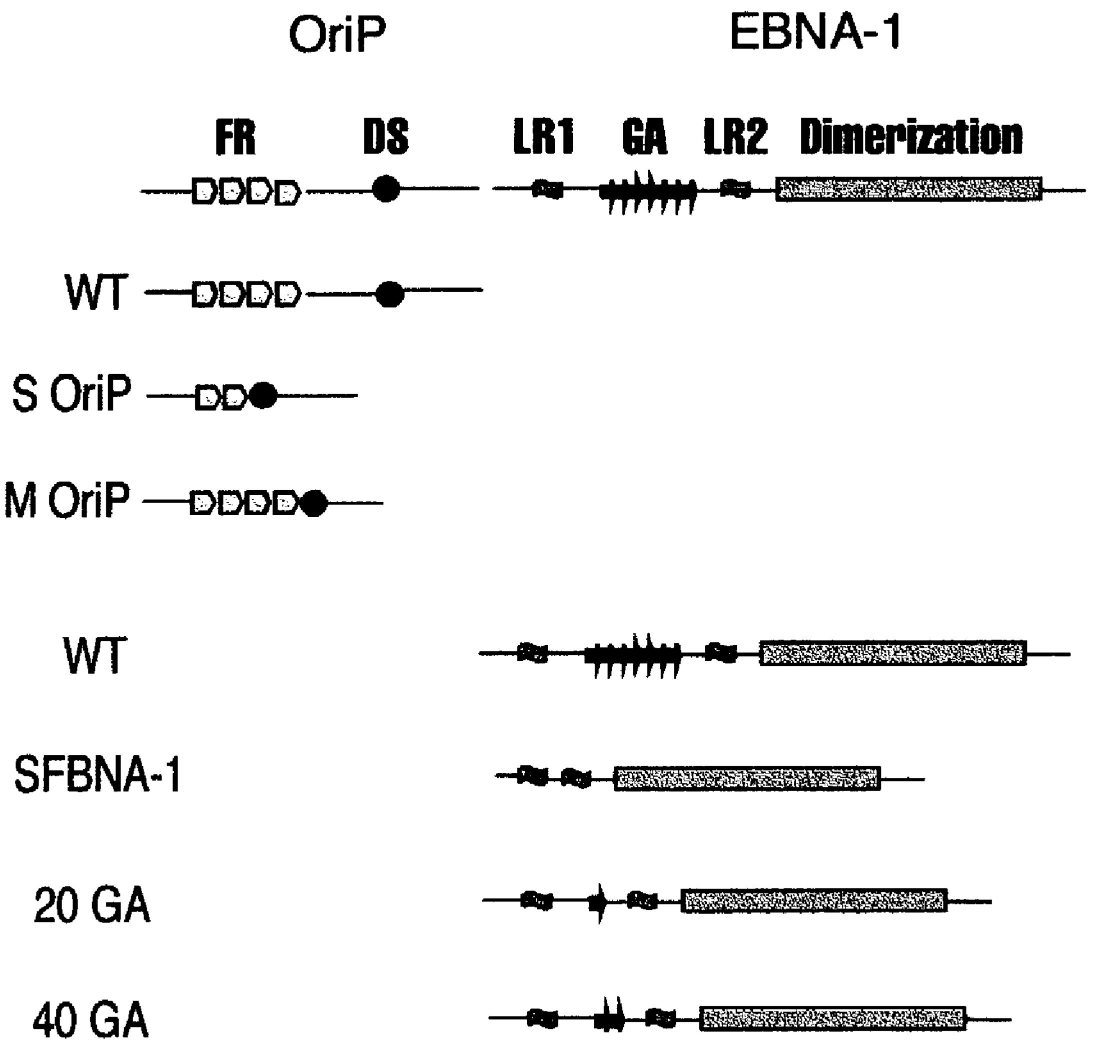
FIG. 9A is a schematic diagram depicting the deletion analysis of the OriP and EBNA-1 regions of the EBV replicon. Structures of the deletions in EBNA-1 and OriP are schematically represented. Elements considered important for episomal maintenance are indicated. "FR" refers to the family of repeats; "DS" designates the region of dyad symmetry; "LR1" refers to the so-called linker region 1; "GA" refers to gly-ala repeats; "LR2" refers to linker region 2; and "Dimerization" designates the dimerization domain.

Most plasmids employing the EBV latent origin of replication exceed 10 kb in length. To provide a means for increasing the capacity of the recombinant adenoviral type A or type B vectors to accommodate a therapeutic gene, a compact EBV replicon having episomal stability was designed. To this end, deletions were generated in both the cis-acting origin of replication, OriP, and the sequences encoding the trans-acting replication protein, Epstein Barr virus nuclear antigen-1 (EBNA-1) (FIG. 9A). Episomal persistence was assessed with a green fluorescent protein (GFP)-bearing test plasmid by determining the fraction of cells retaining green fluorescence as a function of time, assuming that the half-life of GFP, in daughter cells that have not received an episome as a result of segregation failure, is approximately 1.4 days (Fukumura et al., Cell 94:715–725, 1998).

Figure 9B:
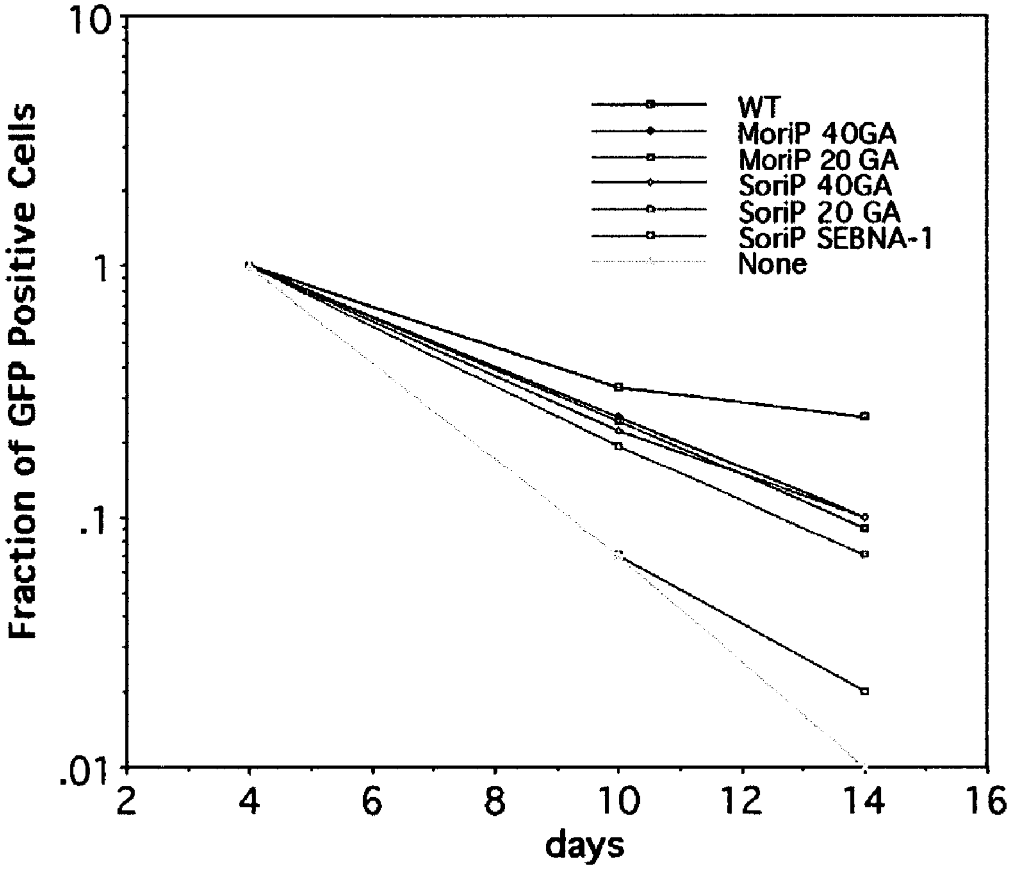
FIG. 9B is a graph depicting fractions of GFP positive cells carrying the EBV replicons represented in FIG. 9A.

EBNA-1 contains a central repeated structure that consists entirely of Gly and Ala residues, termed the GA repeats (FIG. 9A). Although deletion of this structure has been reported to have little consequence, a deletion mutant consisting of both a short OriP and a short EBNA-1 (SoriP+SEBNA1) was generated and found not to support plasmid maintenance effectively (approximately 40% loss per cell division). A version of this mutant, reconstructed with 40 GA repeats, in which the short OriP was paired with a short EBNA-1 provided significantly better plasmid stability (20% loss per cell division vs. 10% per cell division for the wild type) (FIG. 9B). Since most target tissues are relatively quiescent mitotically, this level of segregation fidelity provides reasonable stability in a compact replicon.

Producing Cell Lines that Express Cre- or FLP-Dominant Negative Mutants

As discussed herein, one obstacle to creating adenovirus carrying both recombinase and target sites has been the difficulty of controlling recombinase activity during virus propagation. Since efficient recombinase activity is needed in target cells, recombinase activity is best tempered in the production cell line.

Vector-independent methods to suppress recombinase activity during the production phase are attractive because they allow vector design objectives to be pursued with fewer constraints. In principle, dominant negative recombinase mutants provide the desired antagonism of recombinase activity. Cell lines expressing such recombinase dominant negative mutants were produced as follows.

Figure 10A:
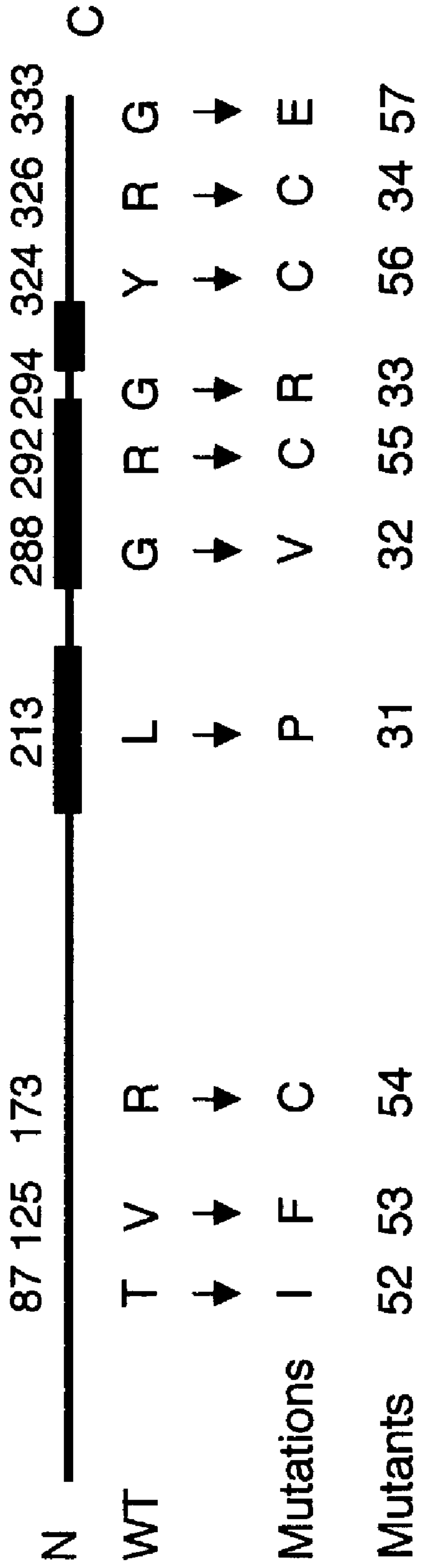
FIG. 10A shows the positions and identities of Cre mutants tested for their dominant negative Cre activities.
Figure 10B:
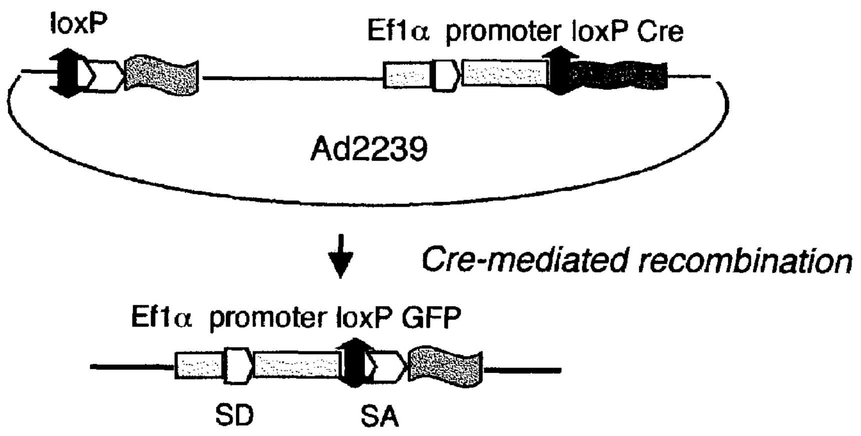
FIG. 10B is a schematic diagram of the substrate Cre plasmid (ad2239) used to test dominant negative functions of Cre mutants.
Figure 10C:
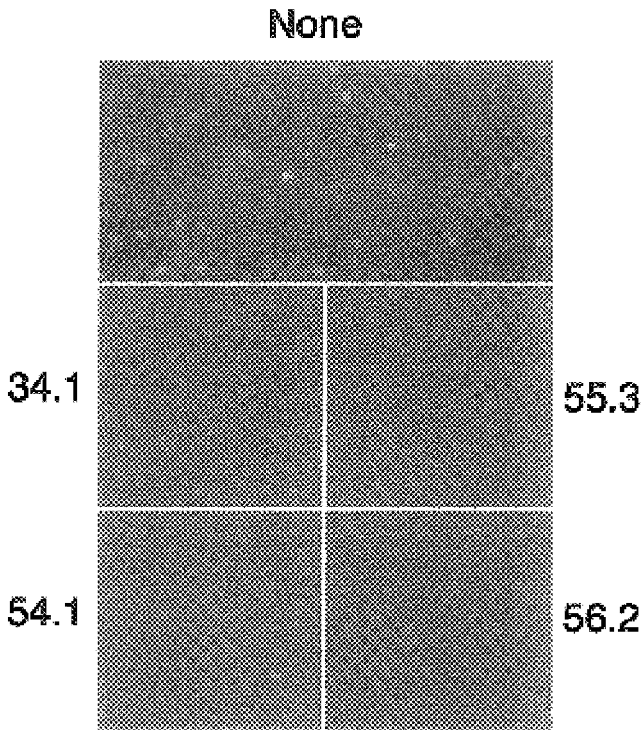
FIG. 10C shows GFP expression in cells cotransfected with the substrate Cre plasmid (ad2239) and the indicated Cre mutants.
Figure 10D:
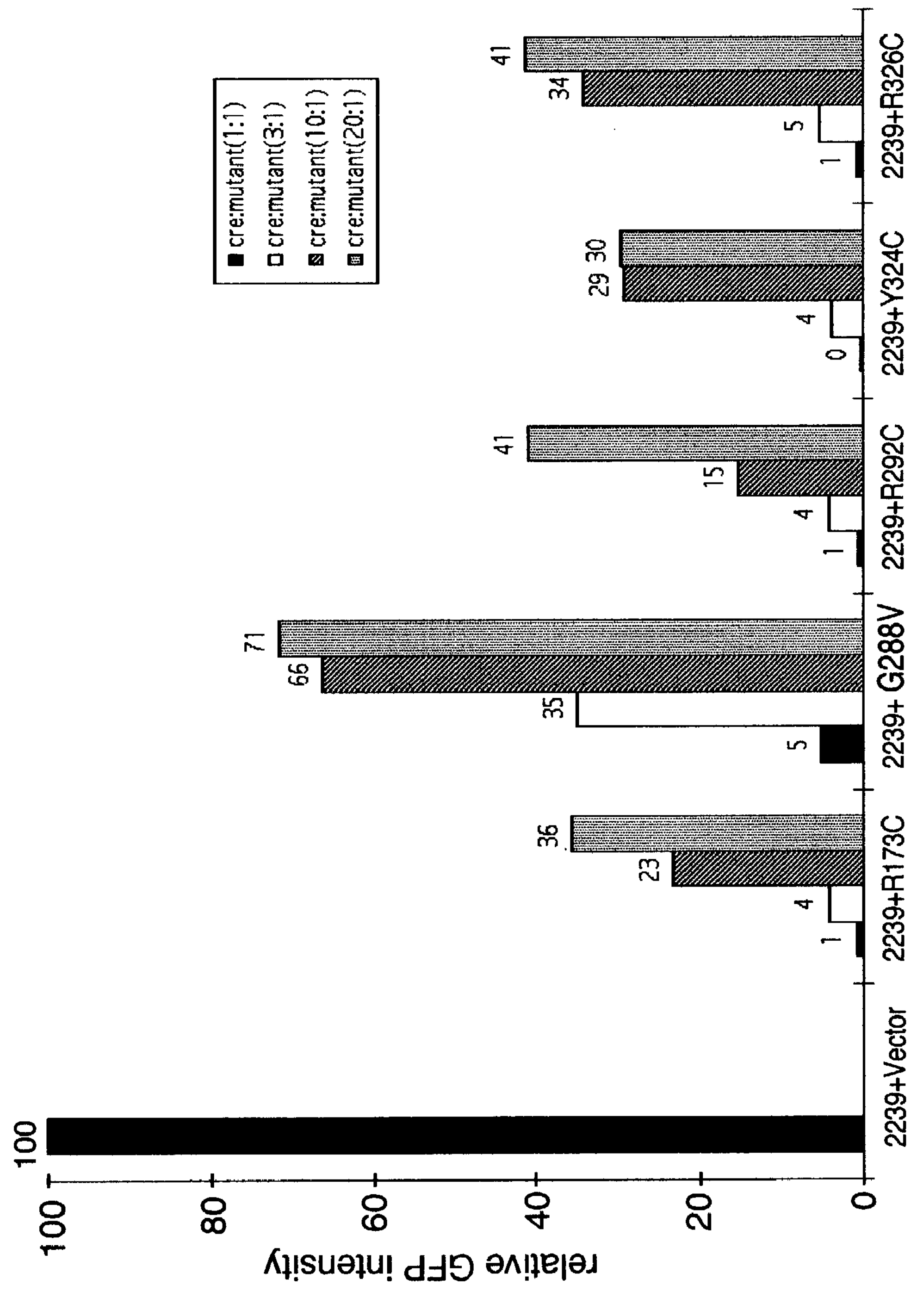
FIGS. 10D and 10E show Cre mutants tested for their ability to inhibit rearrangement. Only those showing the strongest inhibitory activities were retested in FIG. 10E. GFP intensity was normalized to that of cells in the absence of inhibition.
Figure 10E:
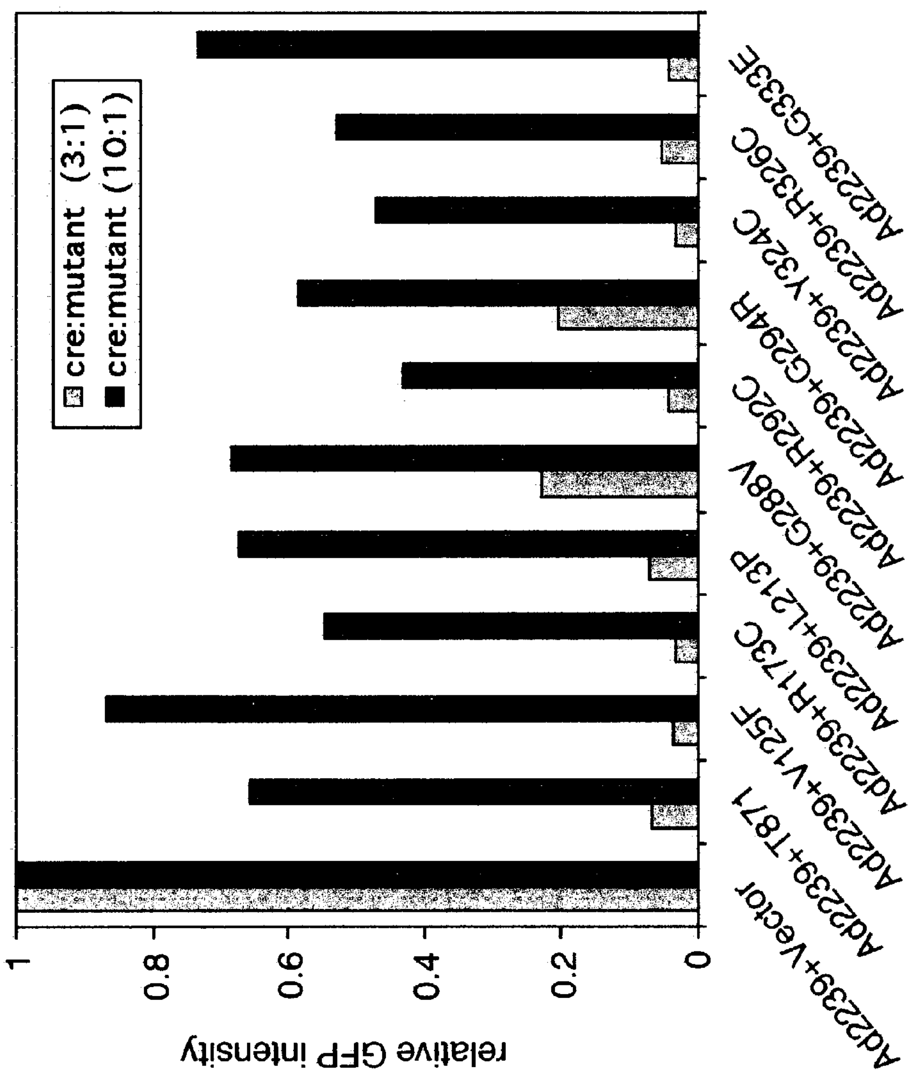

Dominant negative Cre mutants were selected from known point mutants (Wierzbicki et al., J. Mol. Biol. 195: 785–794, 1987) that are defective in recombination function but are likely to retain dimerization function FIGS. 10A–E. Several mutants were screened for their abilities to inhibit Cre activity of a type B vector construct (ad2239 in FIG. 10B) in a transient cotransfection assay. Under these conditions, Cre activity is detected by the expression of GFP that occurs upon rearrangement. FIGS. 10D and 10E show the point mutants that were assessed and their relative activities in the transient cotransfection assay. Dilution studies, in which increasing amounts of substrate/Cre plasmid were cotransfected with the mutant forms, were conducted and based on its favorable profile, one mutant recombinase, designated CreY324C, was chosen for further development (FIG. 10D).

Figure 11:
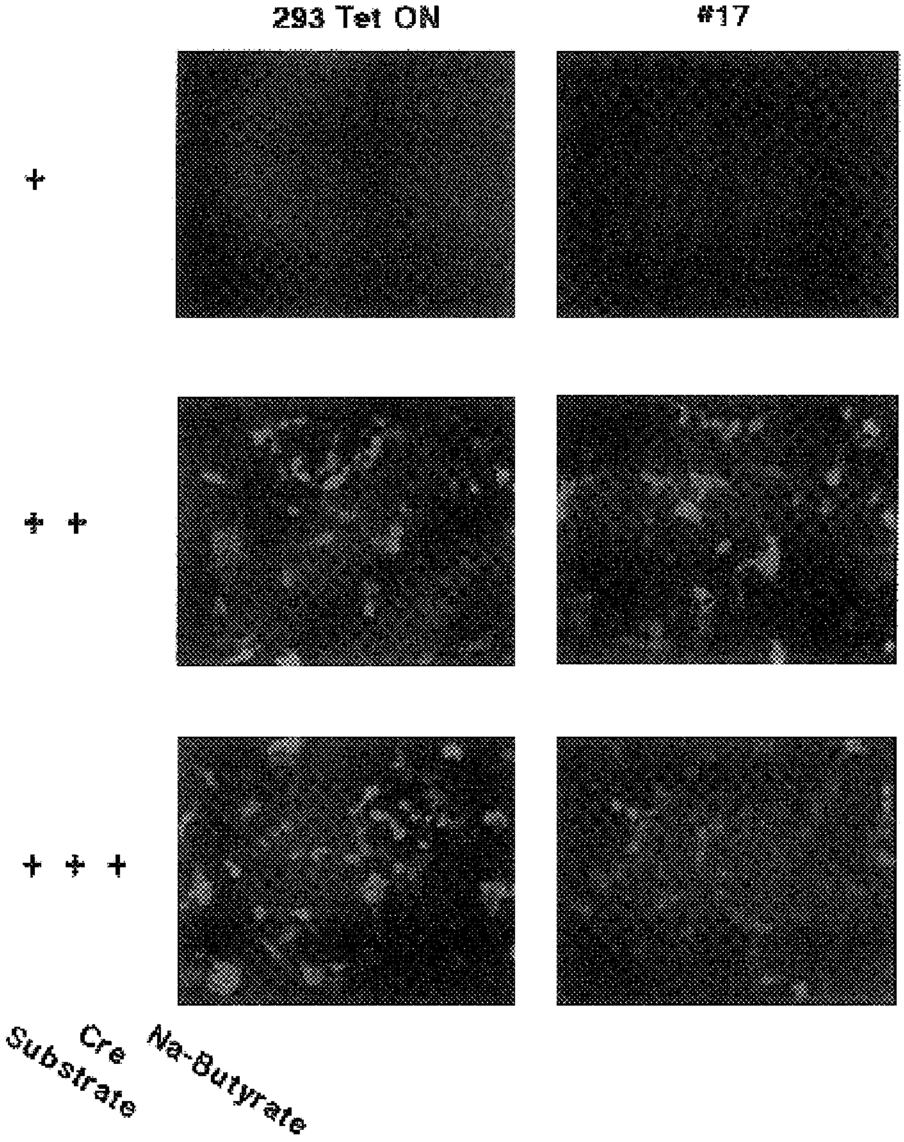
FIG. 11 shows GFP expression in 293 TetON cells and #17 cells transfected with ad2239. The ability of #17 cells to inhibit Cre activity is demonstrated by the weak GFP signal in cells treated with 2 μM doxycycline.

Strong constitutive expression of CreY324C, under control of the Ef1α promoter failed to yield stable cell lines. Stable clones were obtained when the Ef1α promoter was replaced with a tetracycline regulated promoter (Gossen et al., Science 268:1766–1769, 1995). Clones were then tested for the ability to inhibit Cre enzymatic activities, and one clone, designated cell line #17, was selected for additional experiments. When a plasmid bearing Cre and capable of undergoing Cre-directed rearrangement to create a GFP transcription unit (ad2239) was transfected into #17 cells or parental 293ON cells, GFP expression in the #17 cells in the presence of 2 μM doxycycline was significantly lower than those of controls (FIG. 11), showing that Cre enzyme activity can be inhibited in #17 cells.

In addition to dominant negative Cre mutants, dominant negative FLP mutants may also be identified. FLP belongs to the same family of site-specific recombinases as Cre recombinase. A number of FLP mutations that show defects in either cleavage or ligation of FRT sites have been identified. Mutant FLP defective in cleaving FRT site (for example, H309L, L315P, G328R, G28E, N329D, S336Y, S336F, A339D, Y343F, and H345L) are generated using standard methods. Mutants that inhibit the wild type enzyme are then identified for generating stable cell lines according to the methods described above. These and the other cell lines (described herein) are then used for producing FRT/FLP containing virus.

As mentioned above, difficulties creating stable cell lines expressing Cre dominant negative mutants were occasionally encountered. This difficulty was not limited to Cre mutants, but was also observed with the wild-type Cre enzyme. In contrast, 293 cell lines stably expressing a thermostable FLP, referred to as FLPe (Buckholz et al., Nat. Biotechnol. 16:657–662, 1998), were created, suggesting that FLPe might not be as cytostatic as Cre protein. To demonstrate this, 293 cells were transfected with plasmids expressing either Cre or FLPe, and puromycin resistant colonies were selected. To generate stable cell lines expressing Cre or FLP mutants, 293 TetON cells were transfected with linearized plasmid expressing Cre or FLP mutants and puromycin acetyltransferase and selected with 1 μg/ml of puromycin. Puromycin resistant colonies were characterized further for their ability to inhibit Cre recombinase using the cre (ad2239) or flp (ad2879) substrate plasmids. Table 1 shows that there are more puromycin resistant colonies selected from FLPe transfected cells than from Cre transfected cells. From this result, it is expected that stable cell lines expressing a reasonably high level of dominant negative FLP may be readily created.

TABLE 1

Puromycin Resistant Colonies Formed When Cre Expressing or FLPe Expressing Plasmid was Used to Transfect 293 Cells

| Expression Plasmid | Number of colonies (2 μg/ml puromycin) |
|---|---|
| Control | 236 |
| Cre | 92 |
| FLPe | 127 |

Cre or Cre dominant negative mutants were also found to inhibit FLP activity (Table 2). Accordingly, cell lines, such as cell line #17, that stably express a Cre dominant negative mutant (for example, CreY324C), are useful for producing FLP/FRT carrying adenovirus.

TABLE 2

Cre Inhibition of FLP Activity in trans

| Plasmids | Arbitrary GFP intensity |
|---|---|
| Ef1α FLP + FLP substrate + vector control | 4.9 |
| Ef1α FLP + FLP substrate + Ef1α Cre | 0.78 |
| Ef1α FLP + FLP substrate + Ef1α Cre R173C | 2.23 |

Figure 19A:
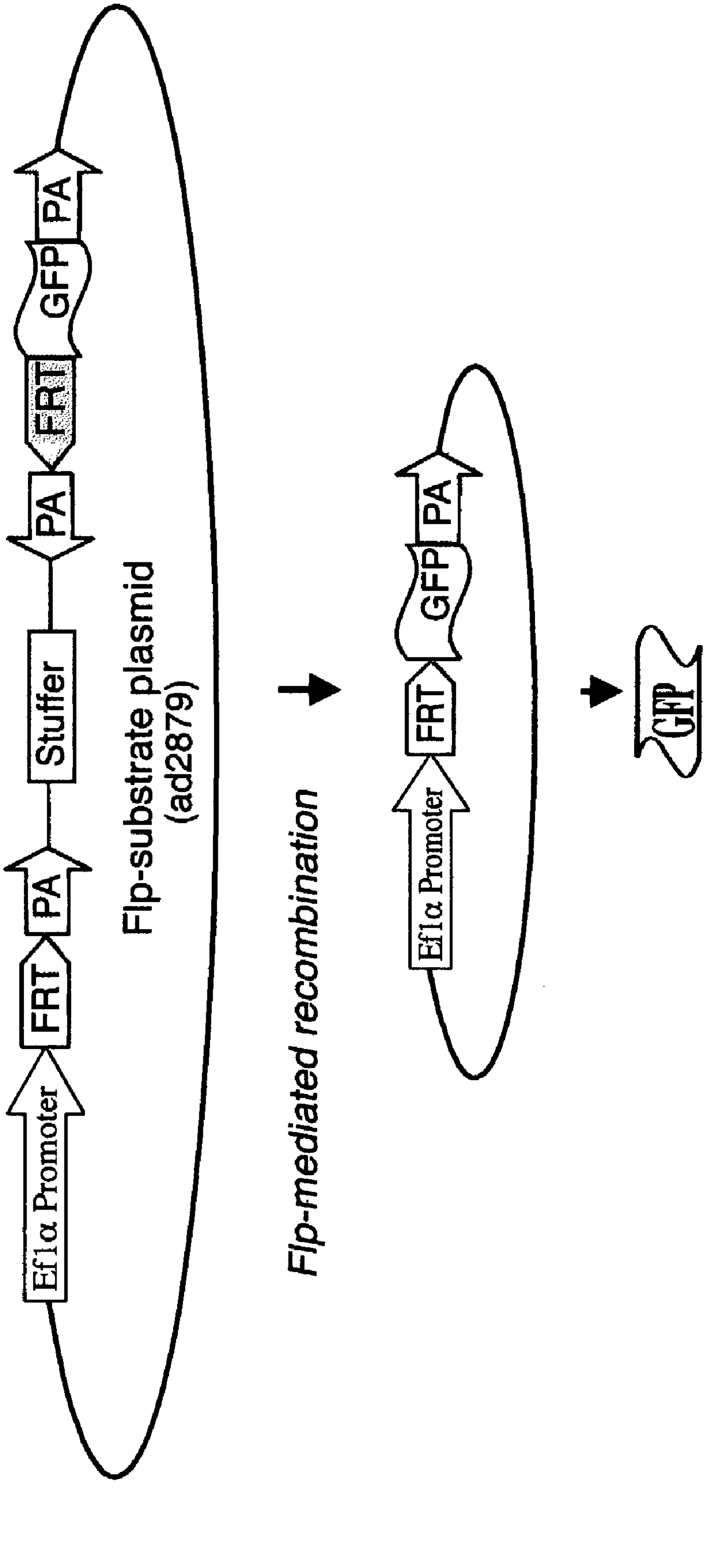
FIG. 19A shows the structure of a FLP substrate plasmid, ad2879. The promoter, Ef1α, and the gene, GFP, are interrupted by 2 FRT sites, which can be joined by the FLP-mediated recombination. "PA" stands for poly A; "BFP" for blue fluorescent protein.

FLP enzyme activity was measured by the GFP intensity by cotransfecting with a FLP substrate plasmid, ad2879 (FIG. 19A). GFP intensity was quantified using IP lab software.

Transcriptional Regulation of Cre or FLP Recombinases

Figure 12:
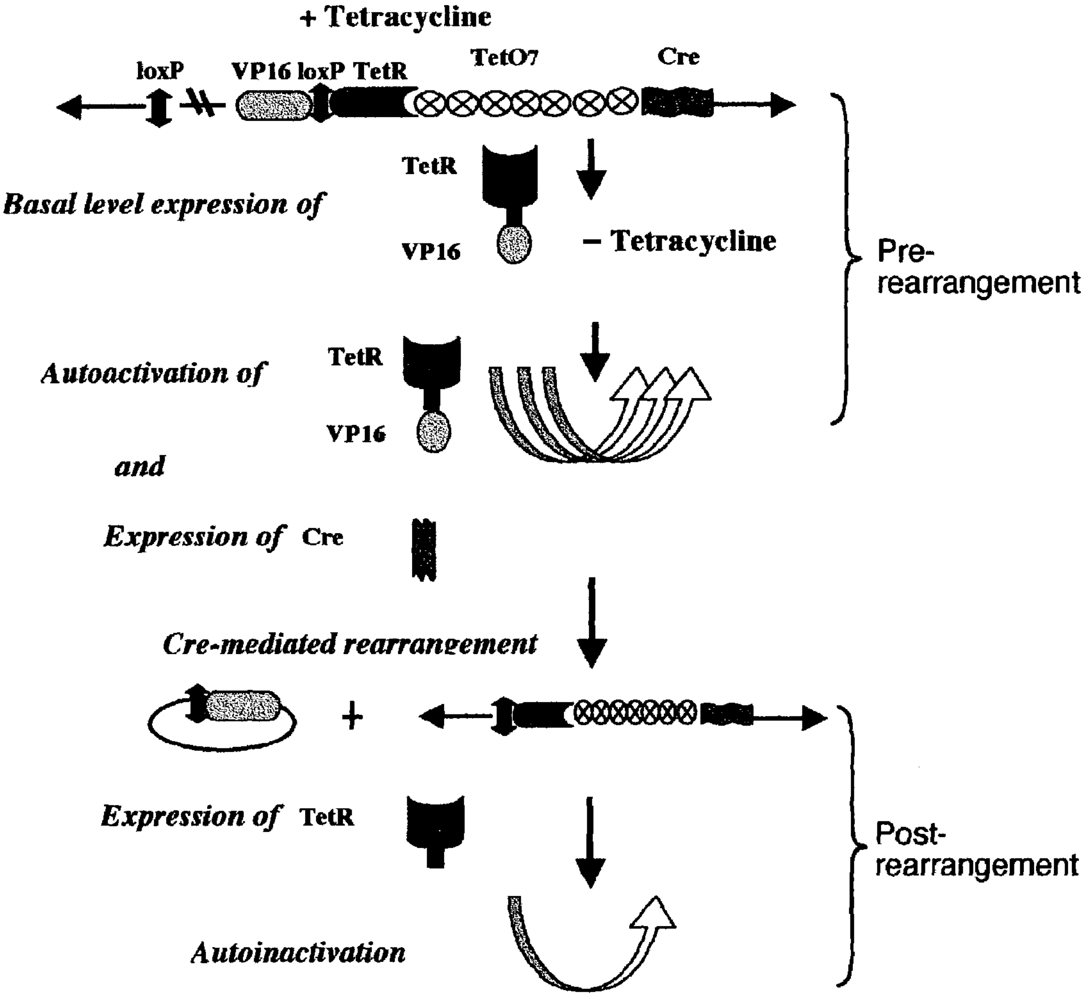
FIG. 12 is a schematic diagram depicting the tetracycline mediated auto-regulatory circuit.

It has been relatively difficult to achieve high-level promoter inducibility in a replicating adenovirus. The challenge is similar to that of achieving faithful control of transcription in a transient expression setting. One approach to increase the induction ratio in a transient setting is the use of auto-regulatory (feed-forward) circuits. One such system, based on tetracycline dependent activation, is shown in FIG. 12. A central heptamer of tetracycline promoter operator sites (TetO sites) was placed between two divergently oriented basal TATA elements. The leftward TATA controls the expression of the TetR-VP16 fusion protein, in which a loxP (or FRT) site has been placed between the TetR DNA binding domain and the VP16 transcriptional activator. The rightward TATA box directs the synthesis of recombinase, either Cre or the yeast FLP enzyme. In the presence of tetracycline, the promoter has reduced activity in both directions. Upon removal of tetracycline, the synthesis of both TetR-VP16 and recombinase are induced (FIG. 1A). The induced recombinase then disjoins the TetR DNA binding element from the transcriptional activation contributed by VP16. Any existing TetR-VP16 fusions thereafter promote transcription of TetR, which competes with TetR-VP16 for TetO, resulting in deinduction of recombinase transcription.

Figure 13A:
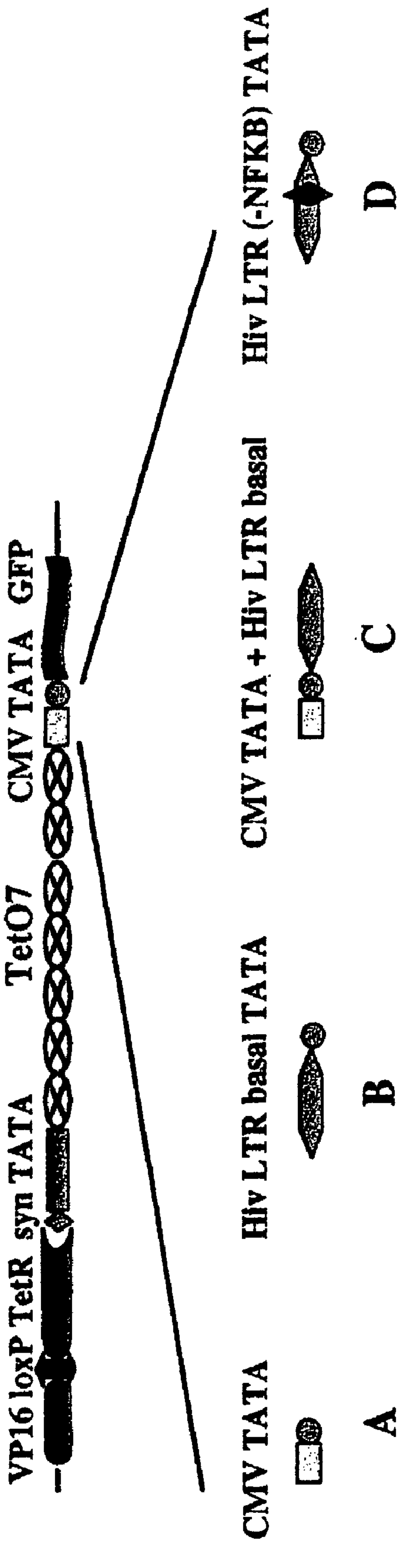
FIGS. 13A and 13B show the effects of different basal elements on synthetic TetO promoter activity.
Figure 13B:
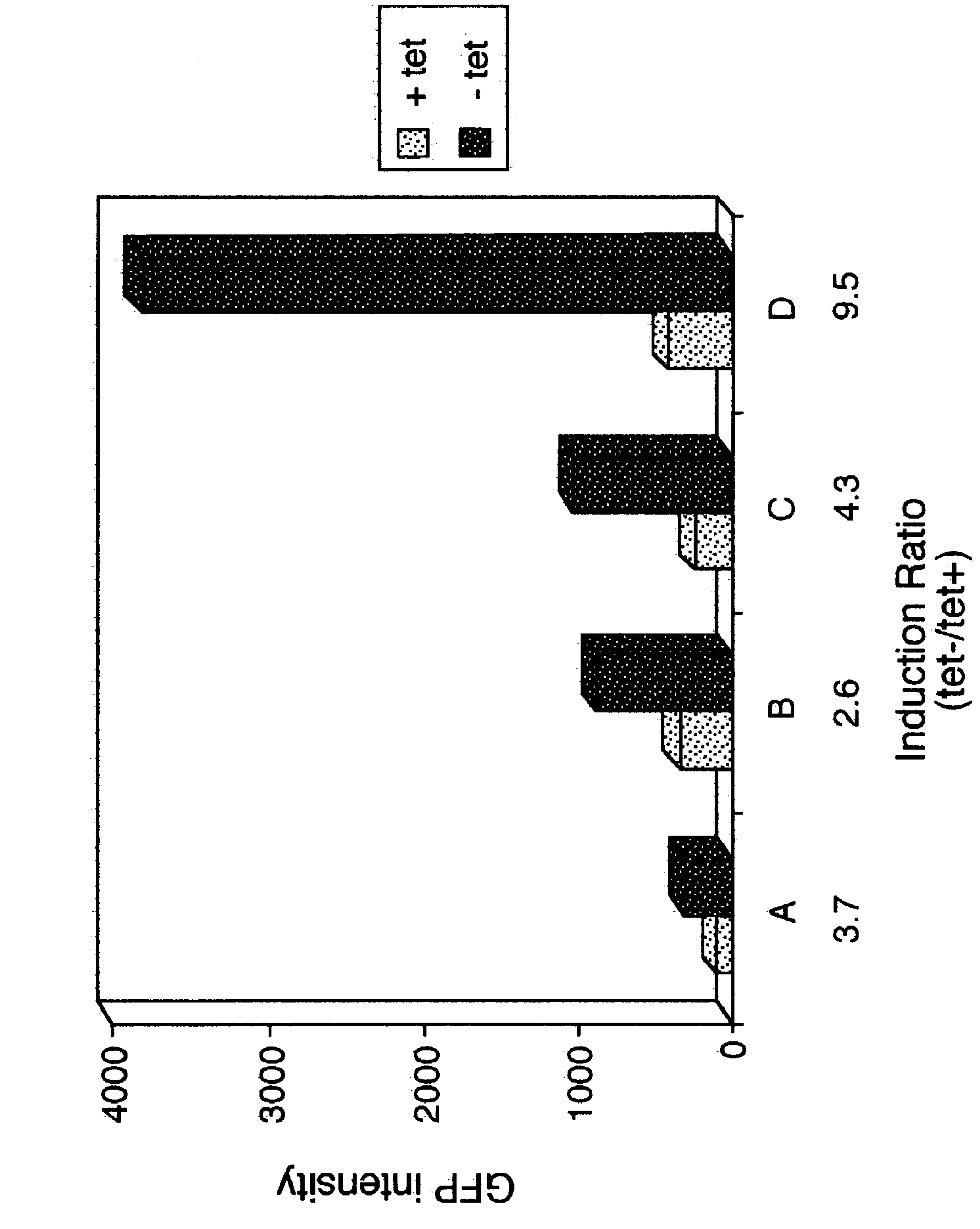

When a model target cell line, HepG2, was tested with this type of adenovirus, the efficiency of circularization was low relative to that seen in 293 cells (data not shown), indicating a cell dependence of the bidirectional TetO promoter. To correct this, the TATA element of the TetO synthetic promoter (derived from the CMV immediate early promoter) was replaced with that of the HIV LTR. Constructs bearing differing components of the HIV basal promoter were analyzed for strength and regulation in 293 and HepG2 cells (FIG. 13A). Among the constructs tested, one version bearing the HIV LTR TATA and Sp1 elements (D in FIG. 13A) showed the least basal expression in 293 cells (data not shown) and the greatest induction in HepG2 cells (FIG. 13B).

Figure 14:
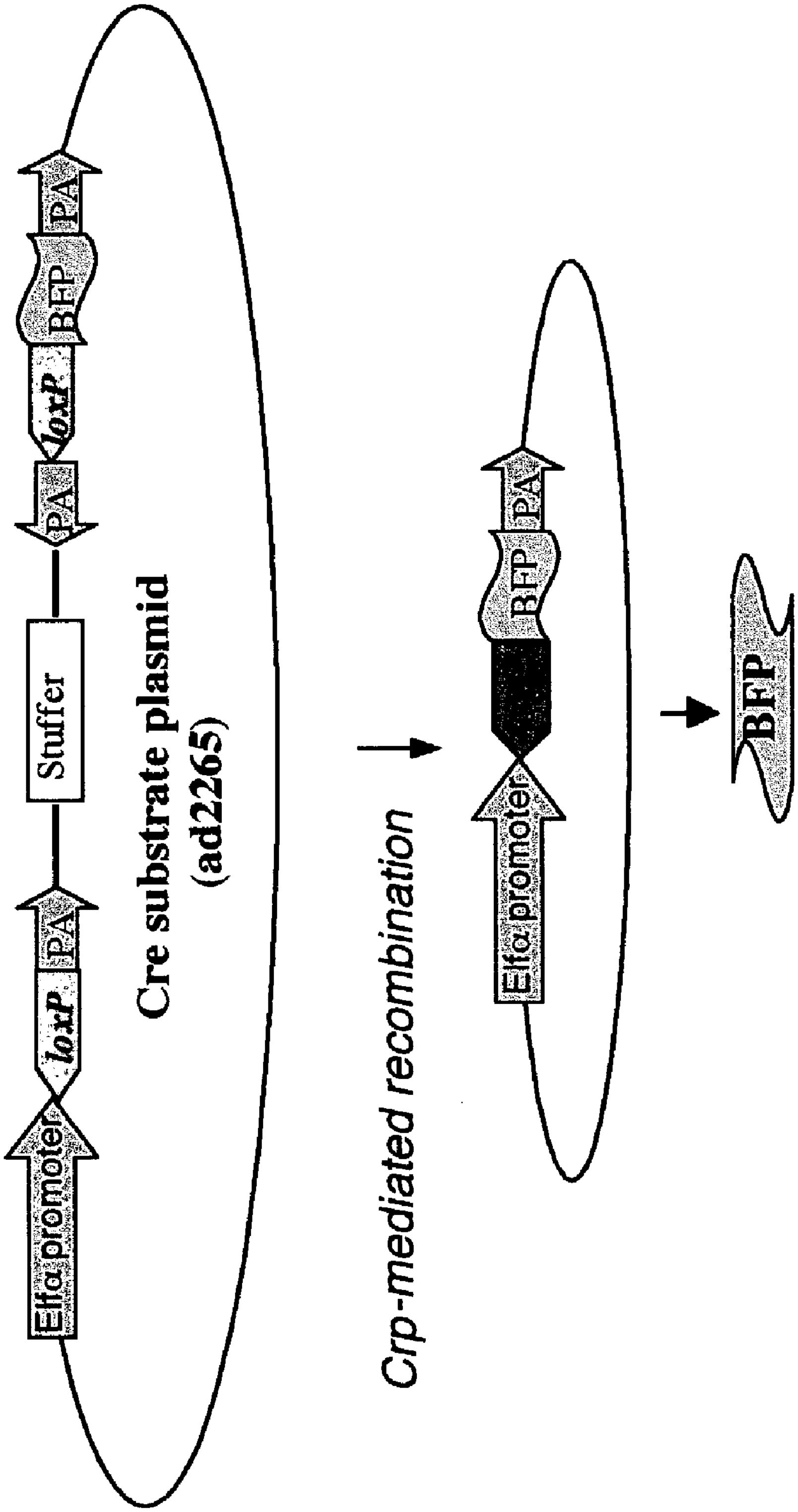
FIG. 14 shows the structure of a Cre substrate plasmid (ad2265). The promoter, Ef1α, and the gene, BFP, are interrupted by two loxP sites, which can be joined by Cre-mediated recombination. "PA" stands for poly A; "BFP" for blue fluorescent protein.

Using this promoter, a construct (ad3400) containing the auto-regulatory structure D as shown in FIG. 13A was engineered, and Cre activities in the presence and in the absence of tetracycline were assayed. Plasmid ad2265 (FIG. 14) in which a blue fluorescent protein (BFP) expression unit is interrupted by two loxP sites and transcription termination sequences was used as a substrate for Cre. Cre-mediated recombination joins BFP to the promoter resulting in BFP expression. As shown in Table 3, no difference was found in the intensity of BFP expression, either in the presence or absence of tetracycline. One possible explanation for this is that very little Cre protein is required for activity. Consistent with this idea, standard imunohistochemical techniques failed to reveal the presence of Cre enzyme in cells that were fully induced (data not shown).

TABLE 3

Cre Recombinase Activity Regulation in Type A Constructs

| Construct | Cre Form | +tet −tam | −tet −tam | +tet +tam | −tet +tam |
|---|---|---|---|---|---|
| ad3400 | Cre | 2.58 | 3.39 | 2.71 | 6.20 |
| ad4394 | Cre-LBD | 0.081 | 0.22 | 0.056 | 1.02 |
| ad4705 | LBD-Cre-LBD | ND | ND | ND | ND |

Cre enzyme activity was measured in the presence or absence of the ligands, tamoxifen, by cotransfecting with the substrate plasmid (ad2265). BFP intensity (mean intensity/area) was quantified by analyzing fluorescent images captured by a digital camera using IP lab software.
ND, refers to fluorescent intensities that were too weak to measure.
Tet, Tetracycline; tam, tamoxifen; LBD, ligand binding domain

Deletion of the PolyA Consensus Sequence from Cre or FLP Transcription Units

To reduce the expression of FLP or Cre recombinase further, the consensus polyA addition signals from the Cre or FLP transcript unit were deleted from vector constructs, leaving polyadenylation dependent on distal downstream sequences, for example, in gene IX. The activity of Crc using type B proviral constructs with or without the polyA signal was measured. As shown Table 4, the construct without polyA signals (AD229.3) showed a significant reduction of GFP intensity compared to a construct bearing the polyA signal (AD230.5). When FLPe constructs of similar structure were evaluated, similar results were found (data not shown). These data show that Cre and FLPe enzyme activity levels can be modulated by attenuating polyadenylation.

TABLE 4

Effect of Deleting polyA Addition Signal From the Cre Expression Unit on Cre Enzyme Activity Level

| | polyA | Relative GFP Intensity |
|---|---|---|
| AD229.3 | − | 0.25 |
| AD230.5 | + | 1 |

Post-Transcriptional Regulation of Cre Recombinase Activity

Post-transcriptional control mechanisms of Cre recombinase activity were also evaluated. Translational fusions between Cre and the ligand binding domain (LBD) of estrogen receptor have been reported to be regulated by estrogen (Feil et al., Proc. Natl. Acad. Sci., U.S.A 93:10887–10890, 1996; Gossen et al., Proc. Natl. Acad. Sci., U.S.A. 89:5547–5551, 1994), or, in the case of mutant estrogen receptors (Metzger et al., Proc. Natl. Acad. Sci. U.S.A. 92:6991–6995, 1995), by the partial antagonist tamoxifen.

Use of a ligand-dependent recombinase (ad4394 in Table 3), in combination with the HIV LTR-based autoregulated Tet system, allowed for a small degree of regulation by tetracycline, but not by ligand, as assayed using the ad2265 rearrangement assay (Table 3). One interpretation of this finding is that fusion of the estrogen receptor LBD to Cre provides only modest control of recombinase activity, but attenuates enzyme potency to a level so that transcriptional regulation can be measured.

To increase control of recombinase activity, the LBD was fused both to the N-terminus and C-terminus of Cre (LBD-Cre-LBD) and inserted into the coding sequence of both type A and type B vectors. When the LBD-Cre-LBD construct of type A was transfected into 293 cells, it showed no significant Cre enzyme activity even in the presence of ligand (Table 3). This result confirmed that the Cre recombinase activity is attenuated by N-terminal or C-terminal extension.

When the LBD fusion Cre enzymes were assayed in the type B vector context, only LBD-Cre-LBD fusions (pk8-ad4626) showed ligand-dependent regulation of Cre enzyme activities (Table 5). It appears that attenuated Cre activity in LBD-Cre-LBD, in the absence of ligand, is low enough to fall below the upper limit of the Cre assay.

TABLE 5

Cre Enzyme Activities of Type B Provirus

| Cre Form | Provirus | −tam | +tam |
|---|---|---|---|
| Cre | pk8-ad2239 | ND | ND |
| Cre-LBD | pk8-ad4332 | 4.1 | 6 |
| LBD-Cre-LBD | pk8-ad4626 | 0.05 | 4.2 |

Cre enzyme activity was measured in the presence or absence of the ligands, tamoxifen. GFP intensity was quantified using IP lab software. tam, tamoxifen.

Consistent with this notion, only the construct carrying two LBDs, pk8-ad4626, was able to produce virus (AD121.5) by transfection and propagate in 293 cells, while pk8-ad4332, which carried one LBD, produced virus (AD100.9) initially (following transfection of the cognate DNA), but was unable to propagate in 293 cells (Table 6). In the case of wild type Cre, no virus was produced in 293 cells by transfection.

TABLE 6

Production and Propagation of Type B Adenovirus

| Cre Form | Type B adenovirus | Viral Production in 293 cells | Viral Propagation in 293 cells | Viral Propagation in #17 cells |
|---|---|---|---|---|
| Cre | Pack8-2239 | − | − | − |
| Cre-LBD | AD100.9 (Pack8-4332) | + | − | + |
| LBD-Cre-LBD | AD121.5 (Pack8-4626) | + | + | + |

The AD100.9 virus was able to propagate in #17 cells expressing the dominant negative Cre Y324C, demonstrating that modulation of Cre activity is important for viral production. Thus, adenovirus carrying both two loxP sites and Cre in two different configurations were generated by controlling Cre activity.

Viral Rearrangement in Culture

Figure 15A:
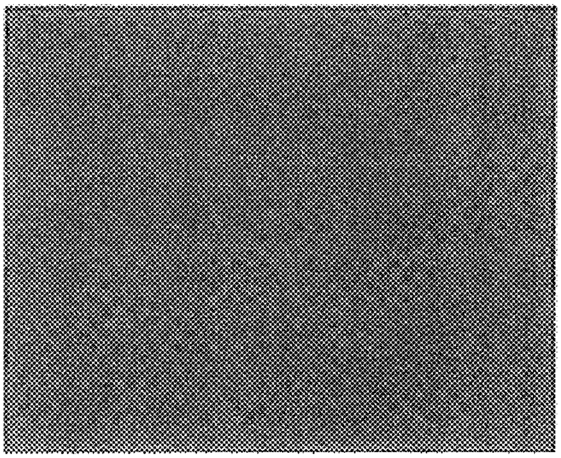
FIGS. 15A and 15B show the estrogen regulation of Cre recombinase activity. 293 cells infected with type B virus, AD121.5, in which the Cre enzyme is fused with estrogen ligand binding domain at both the N- and C-termini were cultured in the presence or absence of 1 μM estrogen. Cre-mediated rearrangement in the presence of estrogen is shown in FIG. 15A, whereas blot analysis of extrachromosomal DNA from the same cells is shown in FIG. 15B. "L" represents the position corresponding to the unrearranged adenoviral DNA; and "C" represents the position corresponding to the circular form of DNA.
Figure 15A:
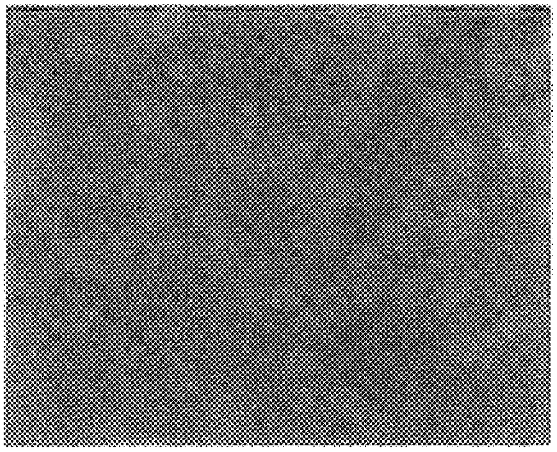
Figure 15B:
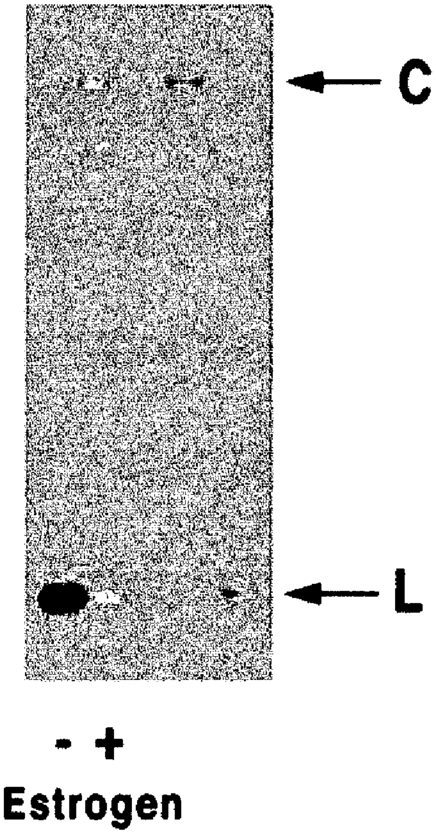

Cre/loxP mediated rearrangement of the adenovirus in tissue culture cells has also been analyzed. As shown in FIG. 15A, the AD121.5 virus showed a significant increase in GFP expression in the presence of the ligand, estrogen, suggesting a successful rearrangement of the virus by Cre recombinases. When non-chromosomal DNA (Hirt, *J. Mol. Biol.* 40:141–144, 1969) was made from the cells and analyzed by DNA blot analysis, the viral DNA from estrogen treated cells was identified mostly in circular form (C in FIG. 15B), while the DNA from cells not treated with estrogen was found mainly in linear form (L in FIG. 15B).

To evaluate the efficiency of the self-rearranging viruses in vivo, high titer stocks of AD102.7 (a type A virus carrying LBD-Cre, pk8-ad4394) in #17 cells was prepared and purified by CsCl gradient ultracentrifugation. The titer of AD102.7 (4–6×$10^{12}$/ml by OD) is comparable to or slightly exceeds that of control viruses (2–4×$10^{12}$/ml by OD), which carry neither Cre nor a loxP site. To determine the efficiency of viral rearrangement in vivo and whether such rearrangement is dependent on the presence of ligand, AD102.7 virus (4×$10^{11}$ pfu/mouse as determined by optical density) were injected via tail vein into Rag-2 mice that were pretreated with vehicle alone or 110 μg/day of tamoxifen for 7 days as follows.

Rag-2 mice were injected with either PBS (mock) or 4×$10^{11}$ adenovirus particles (as determined by $OD_{260}$) of type A virus, AD102.7, via the tail vein. At various times after injection, animals were sacrificed and the liver tissues were removed and frozen rapidly on dry ice. To visualize GFP expression in animal tissues, mice were anaesthetized and perfused with 4% paraformaldehyde containing 0.2% glutaraldehyde intracardially (Kafri et al., Natl Genet. 17:314–317, 1997), and the liver tissues were removed and fixed overnight at room temperature in the perfusion buffer containing 30% sucrose. The fixed tissues were sectioned serially and observed under confocal scanning laser microscopy. In experiments evaluating the responses of ligand-regulated recombinase, mice were injected either with vehicle (vegetable oil) alone or with 110 μg/day of tamoxifen for 7 days prior to adenoviral injection.

Figure 16:
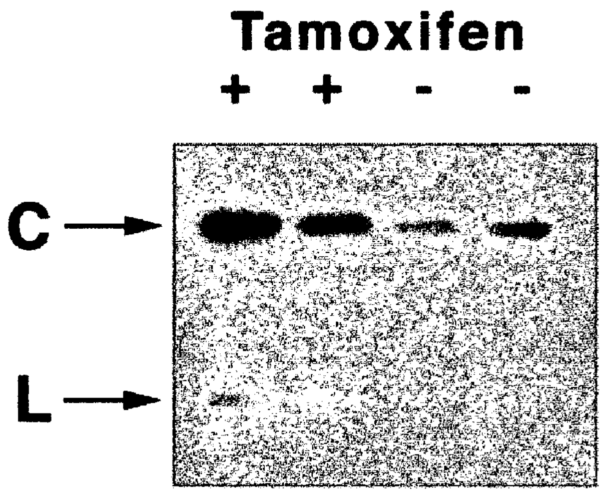
FIG. 16 shows the rearrangement of adenoviral sequences in vivo. Extrachromosomal DNA from the livers of Rag-2 mice sacrificed 2.5 hours post injection of type A adenovirus, AD102.7, was analyzed by DNA blot. "L" represents the size corresponding to linear adenoviral DNA; and "C" represents the size corresponding to rearranged circular DNA.
Figure 17:
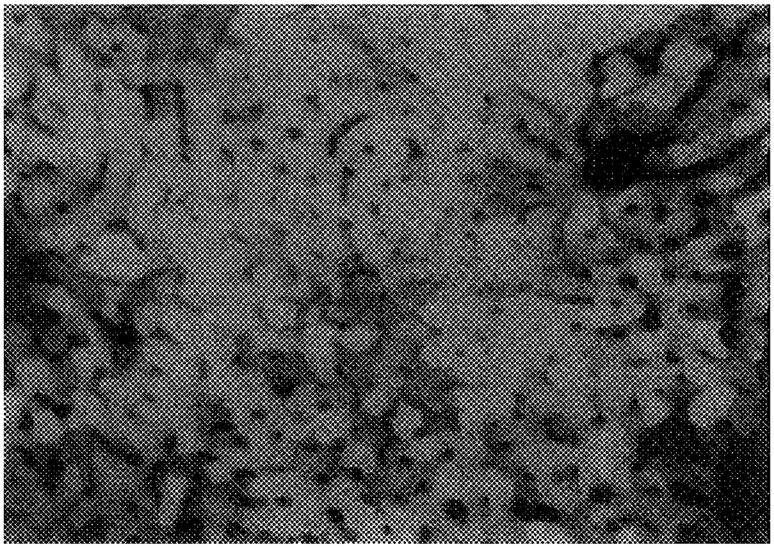
FIG. 17 is a photomicrograph depicting high level GFP expression in Rag2 mouse hepatic tissues 48 hours post type A adenovirus (AD102.7) injection.

Liver tissues from these animals were harvested at 2.5 hours post injection (the earliest time point taken after injection) and Hirt DNA from approximately 250 mg of frozen hepatic tissue was prepared and analyzed by blot analysis. As shown in FIG. 16, the majority of adenoviral DNA was found in circular form in tissues from untreated mice, as well as tamoxifen-treated mice. It can be concluded from these data that the Cre enzyme activity present in the tissue, even in the absence of ligand was sufficient for efficient self rearrangement of virus. As expected, the hepatic tissues from the Rag2 mice injected with AD102.7 showed strong expression of GFP (FIG. 17).

Demonstrating that AD102.7 virus, produced efficiently in 293 cells at high titres by the conventional means, can self rearrange efficiently in vivo provides the proof of the concept that potentially safer adenoviral gene therapy vectors can be produced.

Adenoviruses Carrying Both FRT and FLP Recombinase

Figure 18A:
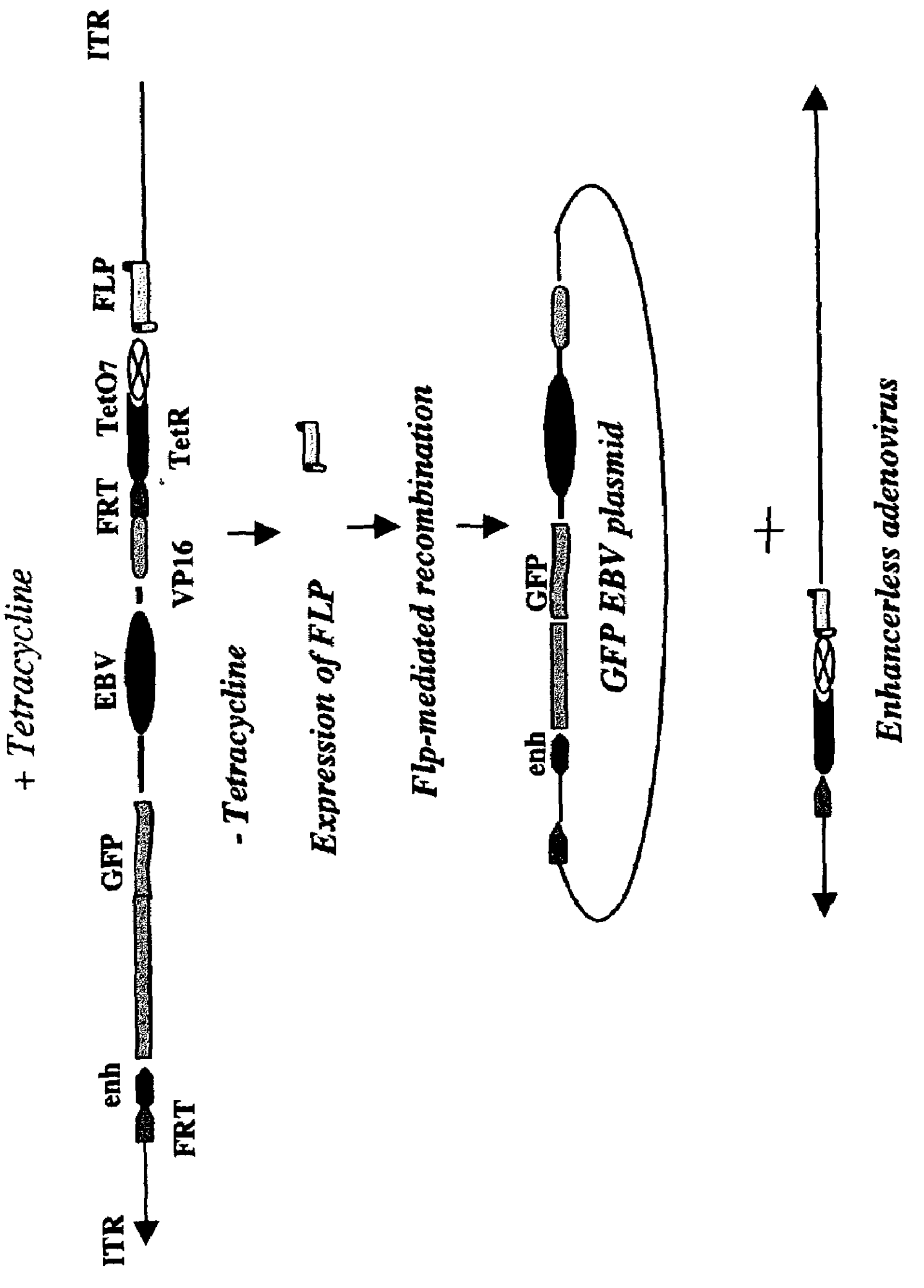
FIGS. 18A and 18B show schematic diagrams of the structures of adenoviral vectors and their fates in target cells. "enh" refers to Ad2 enhancer; "GFP" refers to green fluorescent protein; "EBV" refers to Epstein Barr Virus replicon; "$TetO_7$" refers to heptamer of Tet operator; "TetR" refers to Tet repressor; "VP16" refers to transcriptional activator domain from HSV protein 16; "SD" refers to splice donor site; and "SA" refers to splice acceptor site.
Figure 18B:
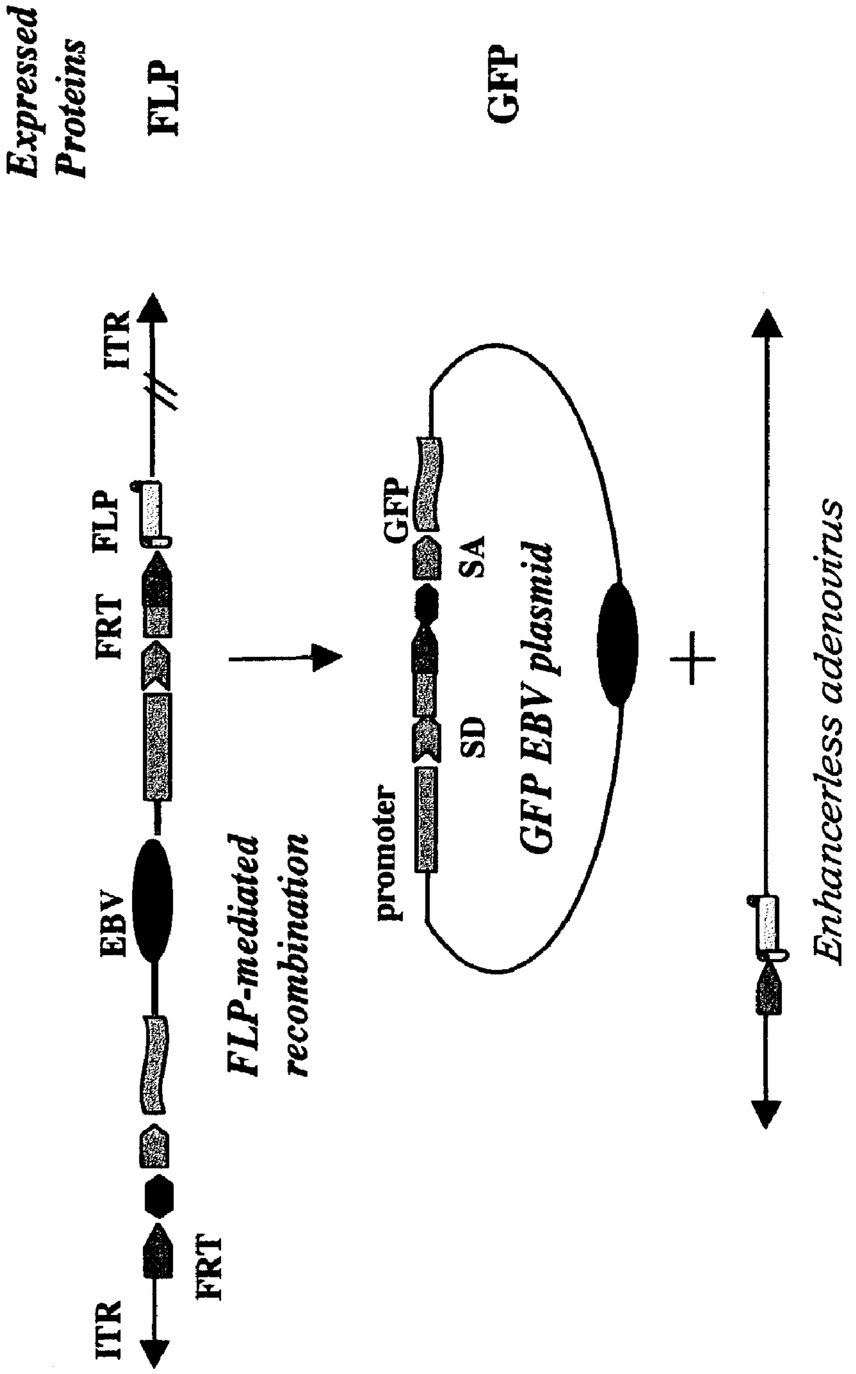

Type A and type B proviral constructs carrying both FRT (FLP recombinase recognition site) and FLP recombinase were also generated. Structures of these viruses are analogous to those of loxP/Cre carrying viruses except that loxP sites are replaced by FRT sites and Cre coding sequence is replaced by FLP coding sequence (FIGS. 18A, 18B).

Virus Production at Reduced Temperature

Temperature dependence of the Ef1α promoter using GFP expression as a marker was also examined. As shown in Table 7, Ef1α promoter activity is strongly reduced at 32° C. in comparison to 37° C. or 39° C. The temperature sensitive nature of the Ef1α promoter was used to propagate type B adenovirus carrying FLP at 32° C. following initial production of the virus by DNA transfection (pk8-ad3302) at 37° C. HepG2 cells infected with these viruses (AD41.4) showed strong GFP expression, but with an approximately 12 hour delay compared to GFP expressing viruses, suggesting that FLP recombinase activity may be impaired at 37° C. To improve the activity of FLP recombinase, viral constructs were created using a thermostable FLP (referred to as "FLPe") described by Buchholz et al. (Nat. Biotechnol. 16:657-662, 1998).

TABLE 7

Effects of Temperature on Ef1α Promoter Strength as Shown by GFP Intensities

| Tester plasmids | | Arbitrary GFP Intensities 32° C. | 37° C. | 39° C. |
|---|---|---|---|---|
| Ef1α GFP | 16 hrs | 1475 | 7886 | 11409 |
| | 41 hrs | 6472 | 36699 | 50787 |
| | 86 hrs | 16256 | 53370 | 54424 |
| Ef1α Cre + ad2204 | 16 hrs | 243 | 1141 | 2132 |
| | 41 hrs | 1094 | 9119 | 9784 |
| | 86 hrs | 695 | 3219 | 8144 |

Figure 19B:
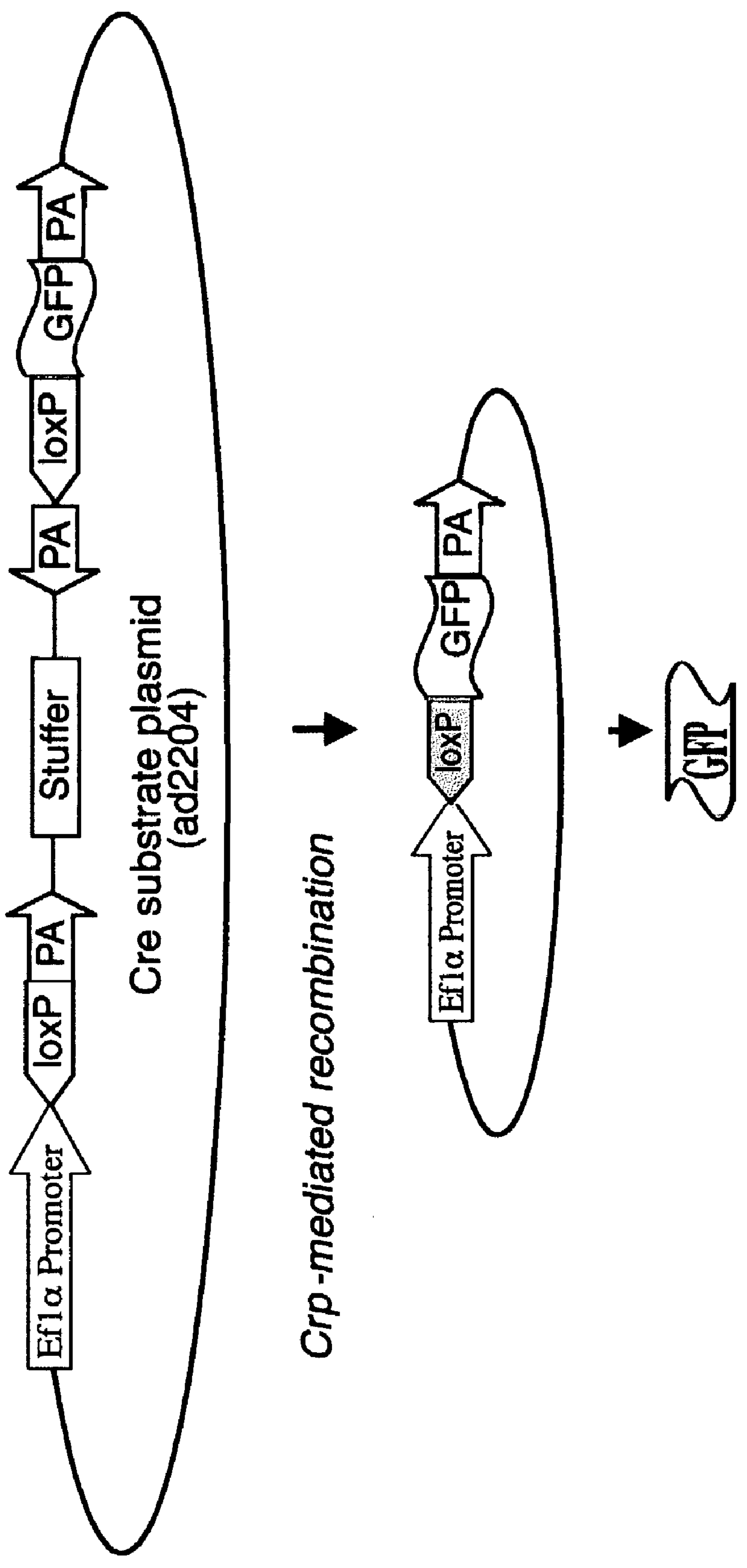
FIG. 19B shows the structure of a cre substrate plasmid, ad2204.

GFP intensities were measured using a Fluorescent reader.
ad2204 is a cre substrate plasmid (FIG. 19B).

The activities of FLP and FLPe using a FLP substrate plasmid (ad2879, FIG. 19A) in 293 cells were compared. As shown in Table 8, FLPe is significantly more active than FLP under these conditions.

TABLE 8

FLPe is Significantly More Active than FLP Recombinase

| Plasmid | | Mean GFP intensity |
|---|---|---|
| ad4821 | Ef1α FLPe | 2.39 |
| ad2949 | Ef1α FLP | 0.01 |

Plasmid coding either FLPe or FLP was cotransfected with a FLP substrate plasmid (FIG. 19A) into 293 cells. GFP intensity of each transfection was measured using IP lab program.

In addition, a tamoxifen-regulated FLPe was created by fusing the ligand-binding domain from a mutant form of estrogen receptor to the FLPe coding sequence at its C-terminus (FLPe-LBD). The FLPe-LBD was found to be regulated by the ligand, tamoxifen (Table 9). Although FLP activity was retained by C-terminal fusion (FLP-LBD), addition of a short oligopeptide tag to the N-terminus of FLP abolished its activity (data not shown).

TABLE 9

Tamoxifen Regulation of FLPe as Determined by GFP Intensities

| Plasmid | FLPe | −tam | +tam |
|---|---|---|---|
| ad4821 + ad2879 | FLPe | ++++ | ++++ |
| ad5022 + ad2879 | FLPe-LBD(tam) | + | +++ |

GFP intensity resulting from FLPe mediated recombination was measured using a fluorescent microscope.
tam, 2 μg/ml tamoxifen.

Inhibition of FLPe Activities by Anti-sense FLPe

Figure 20:
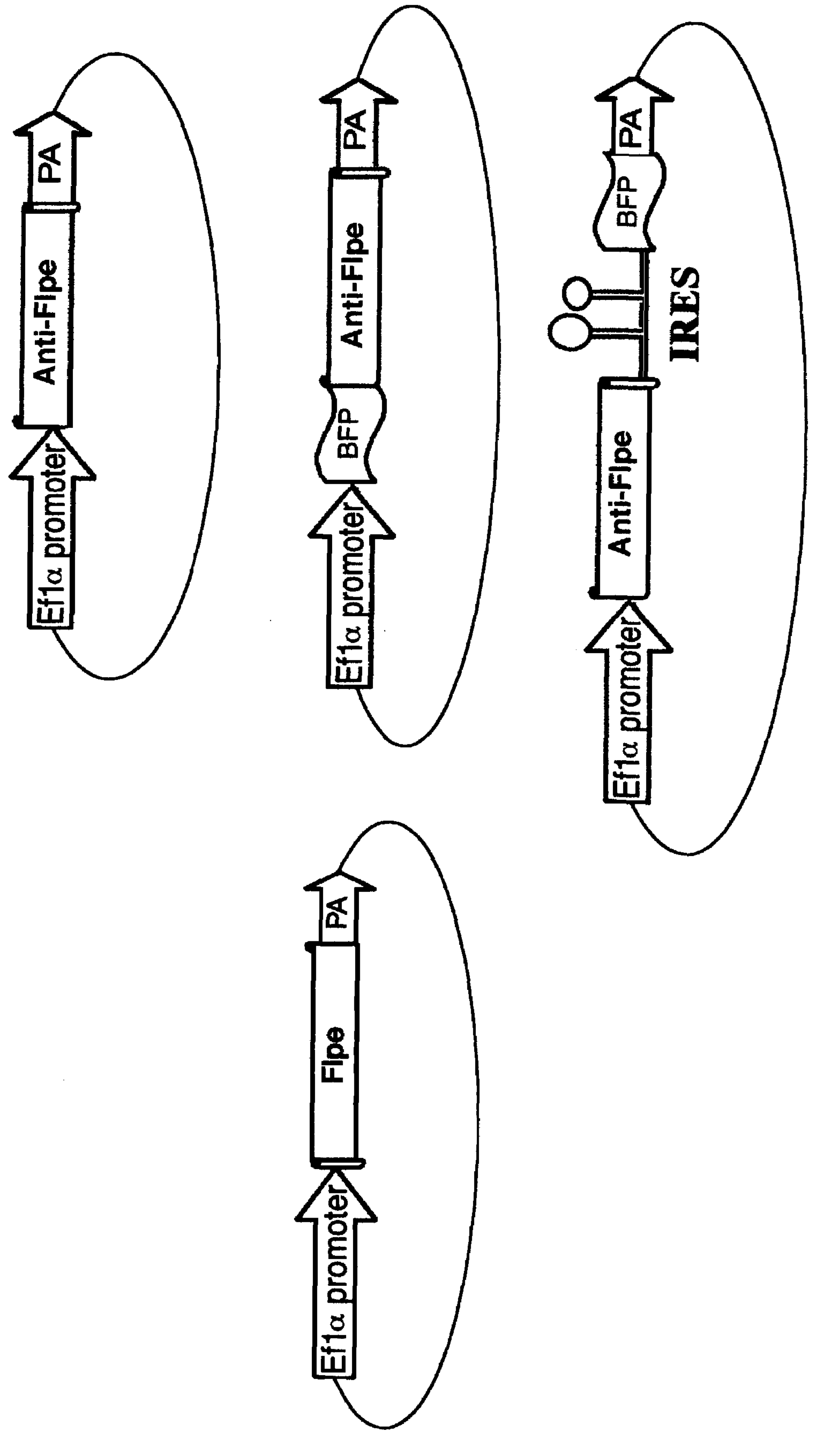
FIG. 20 shows the structures of several FLPe anti-sense plasmids.
Figure 21:
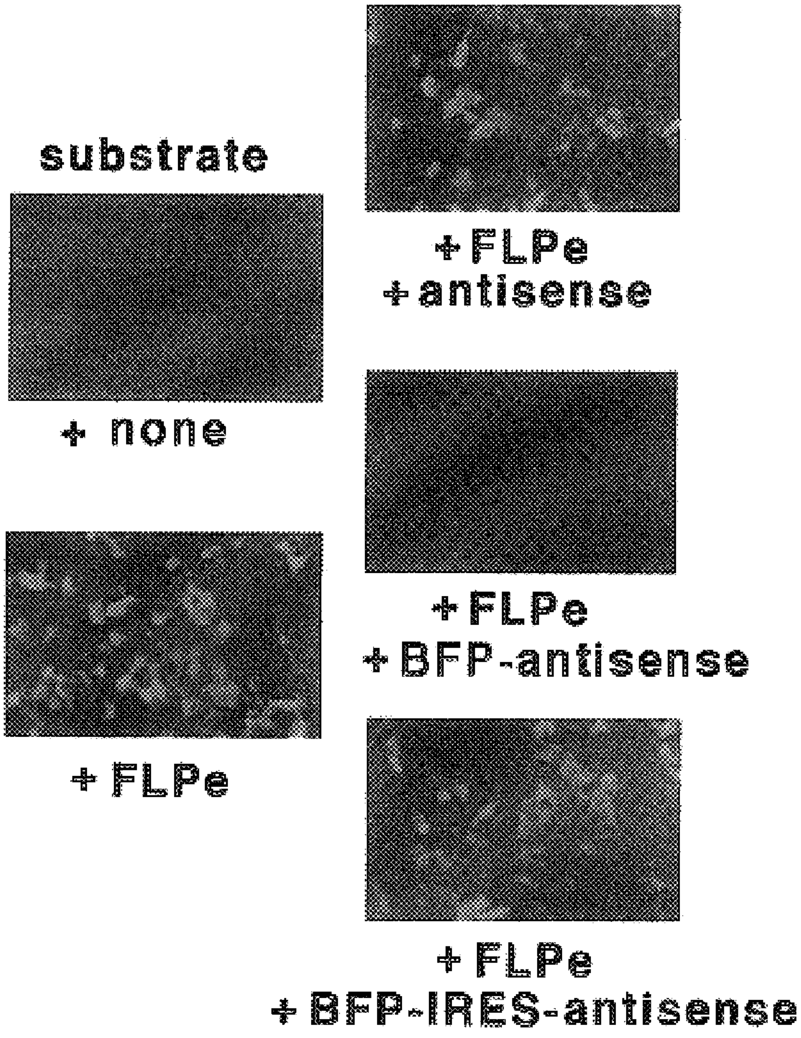
FIG. 21 is a panel of photomicrographs showing inhibition of FLP enzyme activity by anti-sense FLP. 293 cells were transfected with FLP substrate (FIG. 12) and plasmids indicated in each photo. High GFP intensity indicate the higher expression of FLP and less inhibition by the anti-sense expressed.

An anti-sense approach to inhibit FLP enzyme activity was also employed. This approach tested the notion that incorporation of an open reading frame into an antisense transcript would stabilize the transcript and potentiate anti-sense activity. Two approaches were utilized. In one approach, the BFP coding sequence was placed upstream of anti-FLPe. In the second approach, an anti-FLPe was placed upstream of an internal ribosome entry sequence (IRES) and the BFP coding sequence (FIG. 20). The ability of these constructs to inhibit FLPe was assayed using a FLP substrate plasmid, ad2879 (FIG. 19A) and the result is shown in FIG. 21. These data show that anti-sense FLPe is more effective in inhibiting FLPe function when it is fused to BFP, which can presumably be replaced with any other stable protein.

Other Self-Rearranging Adenoviruses

Mixed Infection with Adenoviruses Carrying loxP/FLP and FRT/Cre

Figure 22:
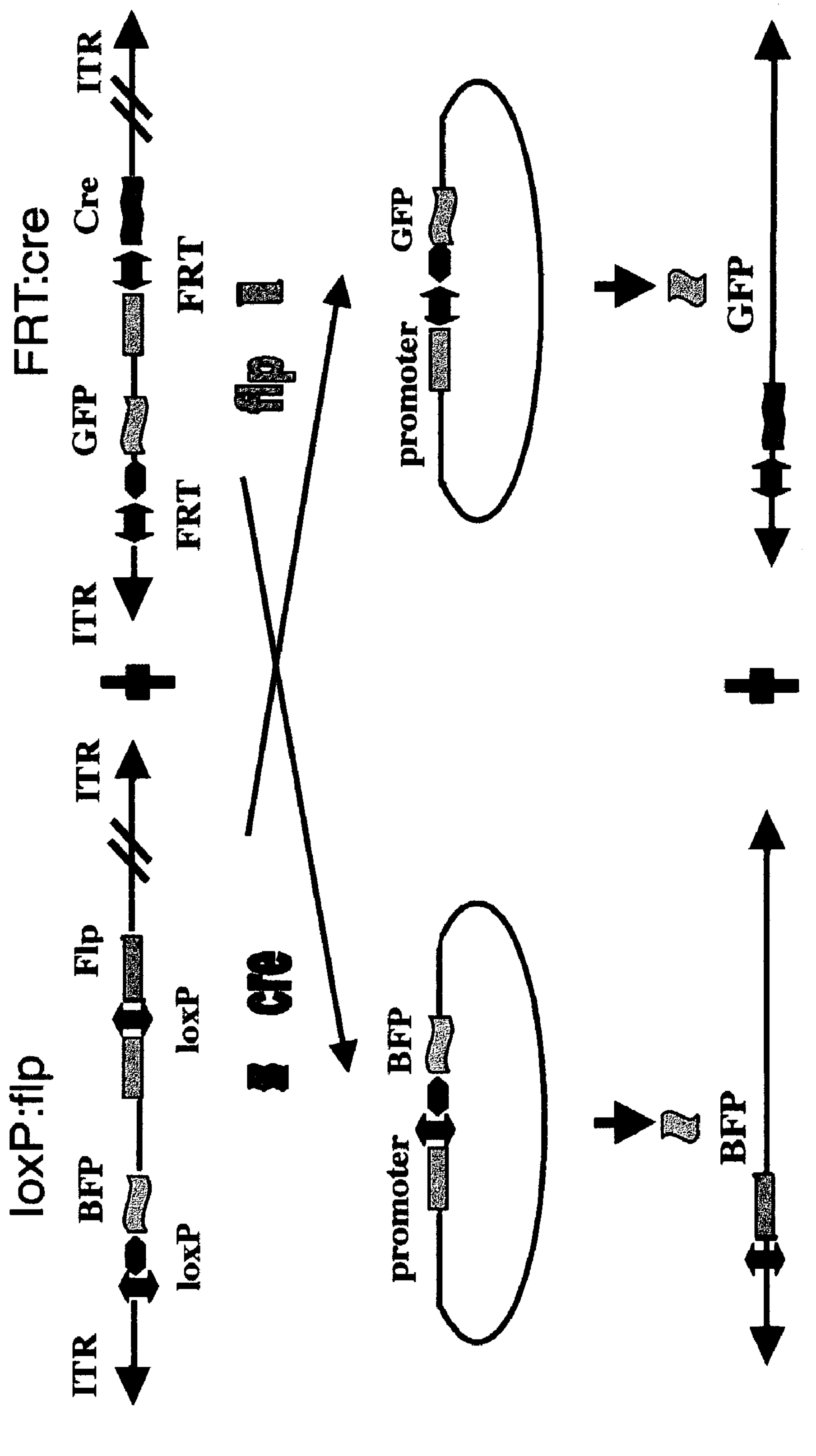
FIG. 22 shows a schematic diagram of FRT/Cre and loxP/FLP adenovirus.

One of the ways to produce adenoviruses that can be rearranged in target cells, but not producer cells, is to engineer two separate viruses, each carrying one recombinase and the target sequence for the other. To test this system, type B adenoviral constructs carrying Cre recombinase and FRT sites and FLPe recombinase and loxP sites were created (FIG. 22). In target cells infected with both viruses, Cre catalyzes recombination between the two loxP sites in the FLP virus, and FLP carries out FRT mediated recombination in the Cre virus, resulting in two circular plasmids. The loxP virus contained BFP, whereas the FRT virus contained GFP. Measurement of the fluorescent intensities of GFP and BFP, after cotransfecting the two constructs, revealed that BFP expression (mediated by Cre enzyme) was greater than GFP expression (mediated by FLP enzyme), suggesting that the Cre enzyme functions more efficiently than FLP.

Accordingly, these two recombinase activities in the target cells need to be balanced for complete circularization of both viral vectors. Exemplary methods for modulating Cre/FLP activity include the use of transcriptional regulation (such as by varying promoter strength and/or with or without poly A addition signal sequence) and translational and/or post-translational regulation (such as by changing FLP to FLPe and making LBD fusion proteins), and post viral production control (such as by changing the ratio of two viruses).

In one approach, Cre was replaced by Cre-LBD and FLP was replaced by FLPe. To improve identification of the rearrangement products, BFP was replaced with RFP as a marker for Cre recombination. As shown in Table 10, in the presence of estrogen, expression of GFP (FLPe mediated) and RFP (Cre mediated) were similar.

TABLE 10

RFP and GFP Expression of Cells Cotransfected With Type B Proviral Constructs Carrying Cre-LBD/FRT(GFP) or FLPe/loxP (RFP)

| Plasmids | Genotypes | GFP intensity | | RFP intensity | |
|---|---|---|---|---|---|
| pk8-ads120 + pk8-ads113 | Cre-LBD/FRT (GFP) + FLPe/loxP (RFP) | Estrogen | | | |
| | | − | + | − | + |
| | | 3222 | 3183 | 46 | 1954 |

To insure that both Cre and FLP carrying viruses with an optimal ratio infect each target cell, these viruses can be cross-linked prior to infection. For example, Cre carrying virus is labeled by biotin while FLP carrying virus is labeled by avidin. Mixing two types of modified viruses generates virus complexes of desired proportions as well. Biotinylation or avidinylation can be carried out using commercially available reagents such as EZ-Link TFP-PEO biotin (Pierce) and EZ-Link maleimide activated NeutrAvidin (Pierce). The extent of the biotin/virus and avidin/virus will be empirically determined to ensure the viability of the virus and to obtain an optimal ratio of two viruses in the complex. Optimal ratios will be those resulting in 1:1 Cre and FLP recombinase activities in target cells. The modifications will be done following manufacture's instructions.

This approach not only increases the effective capacity of adenoviral vector but also opens new avenue of applications involving multiple proteins, some of which cannot be coexpressed in production cell line as a result of combination toxicity.

All references mentioned herein are hereby incorporated by reference.

Other embodiments are within the claims.

What is claimed is:

1. A vector comprising, in the 5' to 3' direction, a first genetically engineered cis-acting target recognized by a recombinase or an integrase;

a gene of interest;

a bi-directional promoter, comprising a second genetically engineered cis-acting target recognized by said recombinase or said integrase; and a nucleic acid molecule encoding said recombinase or said integrase.

2. The vector of claim 1, wherein said first genetically engineered cis-acting target is recognized by a recombinase.

3. The vector of claim 2, wherein said recombinase is Cre or FLP.

4. The vector of claim 1, wherein said first genetically engineered cis-acting target is recognized by an integrase.

5. The vector of claim 1, wherein said vector comprises an origin of replication functioning in a mammalian cell.

6. The vector of claim 5, wherein said origin of replication is part of an Epstein Barr Virus replicon.

7. The vector of claim 6, wherein said Epstein Barr Virus replicon comprises an OriP and an EBNA-1 sequence.

8. The vector of claim 1, wherein said bidirectional promoter comprises TetO sequences.

9. The vector of claim 1, wherein said first genetically engineered cis-acting target is loxP or FRT.

10. The vector of claim 1, wherein said second genetically engineered cis-acting target is loxP or FRT.

11. The vector of claim 1, wherein said bidirectional promoter is operatively linked to a gene encoding a polypeptide comprising a transcriptional activator and a transcriptional repressor.

12. The vector of claim 11, wherein said transcriptional activator is VP16.

13. The vector of claim 11, wherein said transcriptional repressor is TetR.

14. The vector of claim 1, wherein said vector is an adenoviral vector.

* * * * *